US012616696B2

(12) United States Patent
DeCrescenzo et al.

(10) Patent No.: US 12,616,696 B2
(45) Date of Patent: May 5, 2026

(54) CRYSTALLINE FORMS OF (P)-3-CHLORO-4-((3,5-DIFLUOROPYRIDIN-2-YL)METHOXY)-2'-(2-(2-HYDROXYPROPAN-2-YL)PYRIMIDIN-4-YL)-5',6-DIMETHYL-2H-[1,4'-BIPYRIDIN]-2-ONE

(71) Applicant: ACLARIS THERAPEUTICS, INC., Wayne, PA (US)

(72) Inventors: Gary A. DeCrescenzo, Parkville, MO (US); John Robert Springer, Wentzville, MO (US); Susan Landis Hockerman, Kirkwood, MO (US)

(73) Assignee: Aclaris Therapeutics, Inc., Wayne, PA (US)

( * ) Notice: Subject to any disclaimer, the term of this patent is extended or adjusted under 35 U.S.C. 154(b) by 720 days.

(21) Appl. No.: 17/907,514

(22) PCT Filed: Mar. 26, 2021

(86) PCT No.: PCT/US2021/024316
§ 371 (c)(1),
(2) Date: Sep. 27, 2022

(87) PCT Pub. No.: WO2021/195475
PCT Pub. Date: Sep. 30, 2021

(65) Prior Publication Data

US 2023/0242505 A1 Aug. 3, 2023

Related U.S. Application Data

(60) Provisional application No. 63/149,230, filed on Feb. 13, 2021, provisional application No. 63/140,116, filed on Jan. 21, 2021, provisional application No. 63/138,672, filed on Jan. 18, 2021, provisional application No. 63/136,967, filed on Jan. 13, 2021, provisional application No. 63/136,080, filed on Jan. 11, 2021, provisional application No. 63/128,523, filed on Dec. 21, 2020, provisional application No. 63/126,173, filed on Dec. 16, 2020, provisional application No. 63/076,689, filed on Sep. 10, 2020,
(Continued)

(51) Int. Cl.

| | |
|---|---|
| *A61K 31/506* | (2006.01) |
| *A61K 9/00* | (2006.01) |
| *A61K 9/20* | (2006.01) |
| *A61K 45/06* | (2006.01) |
| *A61P 11/00* | (2006.01) |
| *A61P 31/14* | (2006.01) |
| *A61P 37/06* | (2006.01) |
| *C07D 239/24* | (2006.01) |
| *C07D 401/14* | (2006.01) |

(52) U.S. Cl.
CPC .......... *A61K 31/506* (2013.01); *A61K 9/0053* (2013.01); *A61K 9/20* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 45/06* (2013.01); *A61P 11/00* (2018.01); *A61P 31/14* (2018.01); *A61P 37/06* (2018.01); *C07D 401/14* (2013.01); *C07B 2200/13* (2013.01)

(58) Field of Classification Search
CPC ............................ A61K 31/506; C07D 239/24
USPC .......................................... 514/256; 544/333
See application file for complete search history.

(56) References Cited

U.S. PATENT DOCUMENTS

2011/0082155 A1 4/2011 Murugan et al.
2012/0142709 A1 6/2012 Seiness et al.
(Continued)

FOREIGN PATENT DOCUMENTS

WO 0151919 A2 7/2001
WO 2021022186 A1 2/2021

OTHER PUBLICATIONS

Grodowska et al. "Organic Solvents in the Pharmaceutical Industry" 2010, Acta Poloniae Pharmaceutica—Drug Research 67(1):3-12.
(Continued)

*Primary Examiner* — Douglas M Willis
(74) *Attorney, Agent, or Firm* — DLA Piper LLP

(57) ABSTRACT

The present disclosure provides a crystalline form of the methyl/fluoro-pyridinyl-methoxy substituted pyridinone-pyridinyl compound of the structure:

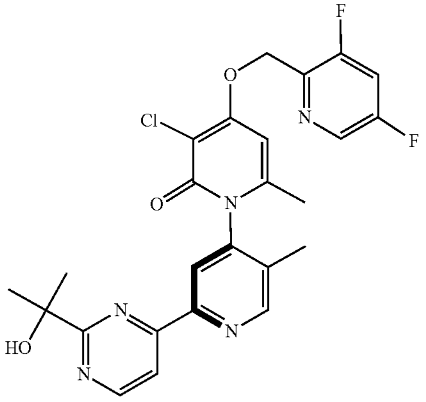

XRPD, TGA, and DSC data on the crystalline form, as well as methods preparing the crystalline form, including a multi-kilo scale preparation. Also provided are pharmaceutical compositions and methods of treating p38 mediated diseases, such as lymphoma and auto-inflammatory disease, including rheumatoid arthritis. and methods of maximizing the yield thereof comprising administering of the compound. Also provided is a method of maximizing the yield of said compound via a recycling procedure.

12 Claims, 11 Drawing Sheets

Related U.S. Application Data provisional application No. 63/053,903, filed on Jul. 20, 2020, provisional application No. 63/024,160, filed on May 13, 2020, provisional application No. 63/022,301, filed on May 8, 2020, provisional application No. 63/022,298, filed on May 8, 2020, provisional application No. 63/018,954, filed on May 1, 2020, provisional application No. 63/015,241, filed on Apr. 24, 2020, provisional application No. 63/000,746, filed on Mar. 27, 2020.

(56) References Cited

U.S. PATENT DOCUMENTS

| | | | |
|---|---|---|---|
| 2014/0364442 | A1 | 12/2014 | Hockerman et al. |
| 2015/0352092 | A1 | 12/2015 | Hockerman |

OTHER PUBLICATIONS

International Search Report and Written Opinion for PCT/US2020/044558 dated Oct. 28, 2020.

Japan Office Action for JP2016-518047 dated Mar. 20, 2018 (with English Translation) 604* Mar. 20, 2018 IS IS.

Japan Office Action and Written Opinion for JP2016-518047 dated Aug. 7, 2018 (with English Translation).

Japan Office Action and Written Opinion for JP2016-518047 dated Oct. 15, 2019 (with English Translation).

Haller et al. An updated patent review of p38 MAP kinase inhibitors (2014-2019), Apr. 20, 2020, Expert Opinion on Therapeutic Patents 30(6):453-466.

Aclaris, "Empowering Patients Through Revelationary Science" Sep. 27, 2019, Aclaris Therapeutics Research & Development Day, retrieved from the internet: URL: https://www.sec.gov/Archives/edgar/data/1557746/000155837019008709/ex-99d1. htm.

Byrn et al. "Pharmaceutical Solids: A Strategic Approach to Regulatory Considerations" 1995, Pharmaceutical Research 12(7):945-954.

International Search Report and Written Opinion for International Paten Application No. PCT/ US2021/024316, mailed Aug. 13, 2021, 11 pages.

Wang et al., "Selective inhibition of the p38alpha MAPK-MK2 axis inhibits inflammatory cues including inflammasome priming signals", Journal of Experimental Medicine. Mar. 16, 2018, pp. 1315-1325, vol. 215.

Tiny-TIM system:
A: gastric compartment
B: pyloric valve
C: intestinal content (chime)
D: small-intestinal compartment
E: salivary & gastric secretion
F: intestinal secretion
G: pre-filter
H: semi-permeable membrane unit
J: filtration (bioaccessible fraction)
K: pH electrodes
L: pressure sensor
M: level sensor

CRYSTALLINE FORMS OF (P)-3-CHLORO-4-((3,5-DIFLUOROPYRIDIN-2-YL)METHOXY)-2'-(2-(2-HYDROXYPROPAN-2-YL)PYRIMIDIN-4-YL)-5',6-DIMETHYL-2H-[1,4'-BIPYRIDIN]-2-ONE

B. CROSS-REFERENCE TO RELATED APPLICATIONS

This application claims the benefit of U.S. Provisional Patent Application Serial No. 63,000,746, filed on Mar. 27, 2020; Ser. No. 63/015,241, filed on Apr. 24, 2020; Serial No. 63,018/954, filed on May 1, 2020; Ser. No. 63/022,301, filed on May 8, 2020; Ser. No. 63/022,298, filed on May 8, 2020; Ser. No. 63/024,160, filed on May 13, 2020; Ser. No. 63/053,903, filed on Jul. 20, 2020; Ser. No. 63/076,689, filed on Sep. 10, 2020; Ser. No. 63/126,173, filed on Dec. 16, 2020; Ser. No. 63/128,523, filed on Dec. 21, 2020; Ser. No. 63/136,080, filed on Jan. 11, 2021; Ser. No. 63/136,967, filed on Jan. 13, 2021; Ser. No. 63/138,672, filed on Jan. 18, 2021; Ser. No. 63/140,116, filed on Jan. 21, 2021; and Ser. No. 63/149,230, filed on Feb. 13, 2021, each of which is hereby incorporated by reference in its entirety.

C. STATEMENT REGARDING FEDERALLY SPONSORED RESEARCH OR DEVELOPMENT

Not Applicable

D. THE NAMES OF THE PARTIES TO A JOINT RESEARCH AGREEMENT

Not Applicable

E. INCORPORATION-BY-REFERENCE OF MATERIAL SUBMITTED ON A COMPACT DISC

Not Applicable

F. BACKGROUND OF THE INVENTION

Not Applicable

1. Field of Invention

Not Applicable

2. Description of Related Art

Not Applicable

G. BRIEF SUMMARY OF THE INVENTION

The present disclosure includes embodiments directed to a compound of Formula (P)-Ia wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^3$ is selected from the group consisting of:

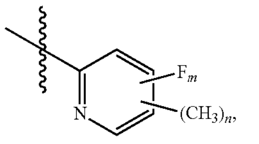

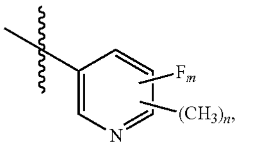

-continued

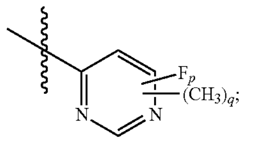

$R^4$ is selected from the group consisting of H, methyl, OH, and —$OCH_3$;

$R^5$ is H or $C_1$-$C_3$ alkyl;

m is 1 or 2;

n is 0 or 1;

p is 1; and q is 0 or 1 or a derivative thereof.

Some embodiments are directed to a pharmaceutical composition comprising a compound of Formula (P)-Ia or a derivative thereof, and a pharmaceutically-acceptable carrier.

In various embodiments, the pharmaceutical composition further comprises one or more additional pharmaceutically active compounds.

In other embodiments, there is provided a method for treating a condition comprising administering to a subject a therapeutically effective amount of a compound of the present invention, alone or in combination with other pharmaceutically active compounds. In any embodiment, suitable conditions to be treated include, but are not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, lymphoma, rheumatoid arthritis, and idiopathic pulmonary fibrosis.

The present disclosure also provides methods for maximizing the synthetic yield of a compound having the structure of Formula (P)-Ia by equilibration or interconversion of a compound having the structure of Formula (M)-Ib:

(P)-Ia

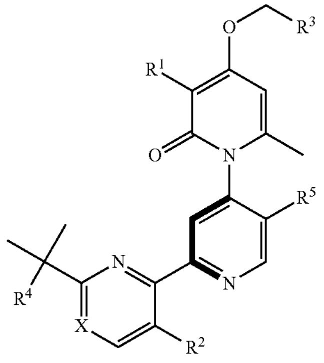

-continued (M)-Ib

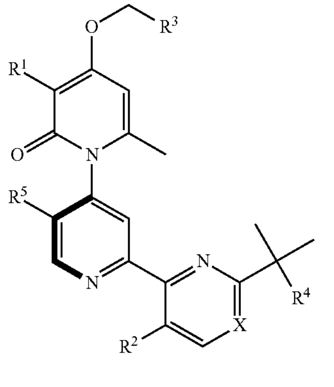

comprising heating a solution comprising the compound having the structure of Formula (M)-Ib to a temperature at which the compound equilibrates to form a mixture of atropisomers.

The present disclosure includes embodiments directed to crystalline forms of Compound 49a, of the structure:

Compound 49a

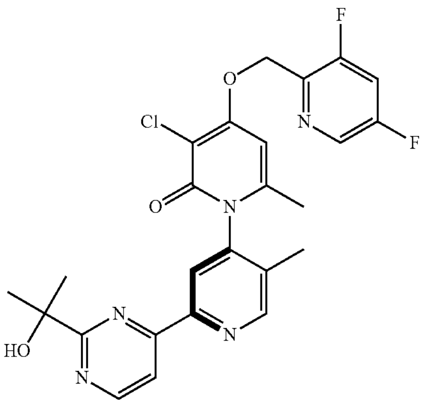

(P)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one The crystalline forms of Compound 49a can been characterized by one or more methods, including but not limited to, X-Ray powder diffraction (XRPD), differential scanning calorimetry (DSC), thermogravimetric analysis (TGA), Raman spectroscopy, infrared spectroscopy, solid-state NMR, and other analytical characterization techniques known in the art.

Pharmaceutical compositions are often formulated with a crystalline solid of the active ingredient (API). The specific crystalline form of the API can have significant effects on properties such as stability, dissolution rate and bioavailability. Instability and poor solubility characteristics can limit the ability to formulate a composition with adequate shelf life or to effectively deliver a desired amount of drug over a given dosing timeframe. One strategy used to achieve the desired physical parameters is to identify the most stable polymorphic form of the API and to define the crystallization processes that would consistently produce the stable crystalline polymorph and avoid producing alternate solid forms, mixtures of polymorphs, hydrates or solvates that can compromise the stability and performance of the composition.

Some embodiments are directed to a pharmaceutical composition comprising a crystalline form of Compound 49a and a pharmaceutically-acceptable carrier.

In various embodiments, the pharmaceutical composition further comprises one or more additional pharmaceutically active compounds.

In other embodiments, there is provided a method for treating a condition comprising administering to a subject a therapeutically effective amount of a crystalline form of Compound 49a of the present invention, alone or in combination with other pharmaceutically active compounds. In any embodiment, suitable conditions to be treated include, but are not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, lymphoma, rheumatoid arthritis, and idiopathic pulmonary fibrosis.

H. BRIEF DESCRIPTION OF THE SEVERAL VIEWS OF THE DRAWINGS

FIG. 5 shows a differential scanning calorimetry (DSC) and thermogravimetric analysis (TGA) thermogram plot of crystalline Form A of Compound 49a.

FIG. 7 shows DSC and TGA thermograms of the results of the scale-up of phase-pure of Compound 49a.

I. DETAILED DESCRIPTION OF THE INVENTION

Figure 1:
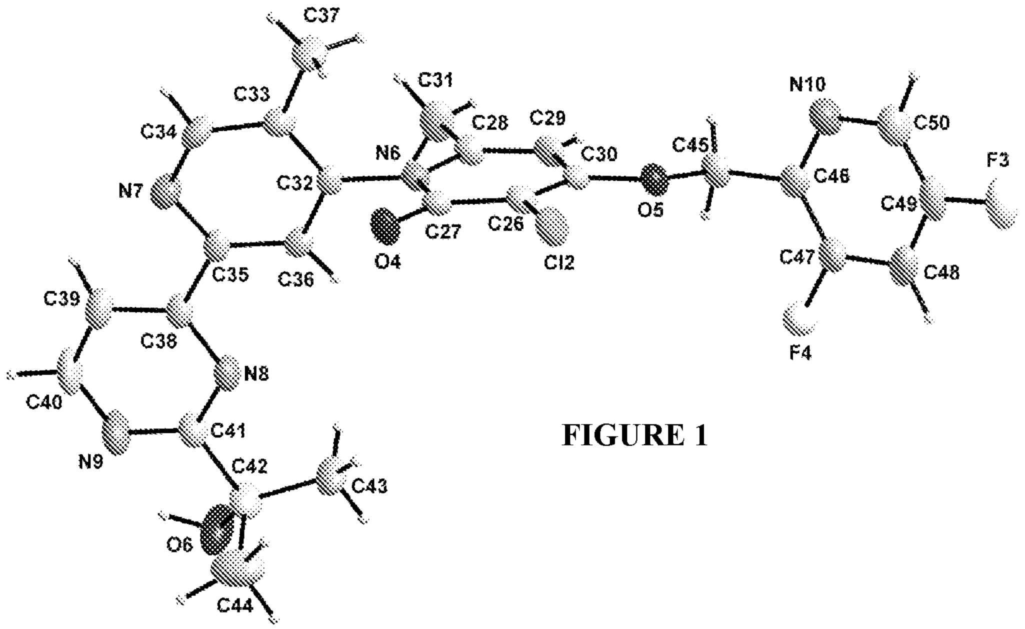
FIG. 1 illustrates the Oak Ridge Thermal-Ellipsoid Plot Program (ORTEP) diagram of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one. This isomer was determined to be (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "p38 MAP Kinase inhibitor" is a reference to one or more p38 MAP Kinase inhibitor and equivalents thereof known to those skilled in the art, and so forth.

The transitional term "comprising," which is synonymous with "including," "containing," or "characterized by," is inclusive or open-ended and does not exclude additional, unrecited elements or method steps.

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g., nutrient depletion) is the specifically recited therapeutic(s) in the particular embodiment or claim.

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

As used herein, the term "a derivative thereof" refers to a salt thereof, a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, an isotope thereof (e.g., tritium, deuterium), or a combination thereof.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

The term "inhibit" means to limit, prevent or block the action or function of a target enzyme and/or, to prevent, alleviate or eliminate the onset of one or more symptoms associated with a disease, condition or disorder, or to prevent, alleviate or eliminate a disease, condition or disorder.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $-C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein.

Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($—CH_2—$). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—).

Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a-C(O)N(RR') group with R and R' as defined herein or as defined by the specifically enumerated "R" groups designated. The term "N-amido" as used herein, alone or in combination, refers to a RC(O)N(R')-group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C6H4=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a-OC(O)NRR', group- with R and R' as defined herein.

The term "N-carbamyl" as used herein, alone or in combination, refers to a ROC(O)NR'-group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene ($—CF_2—$), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, $—CH_2—NH—OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS-group, where R is as defined herein.

The term "nitro," as used herein, alone or in combination, refers to —$NO_2$.

As used herein, an "N-oxide" is formed from the tertiary basic amines or imines present in the molecule, using a convenient oxidizing agent.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "substantially free" or as used herein, alone or in combination, and is used interchangeably with, the term "substantially pure", refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS). In embodiments, substantially free may be less than about 1.0%, less than about 0.5%, less than about 0.4%, less than about 0.3%, less than about 0.2%, less than about 0.1%, less than about 0.05%, or less than about 0.01%.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a $RS(=O)_2NR'$— group with R and R' as defined herein.

The term "S-sulfonamido" refers to a —$S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

The term "3,5-difluoropyridin-2-yl" refers to a moiety of structure:

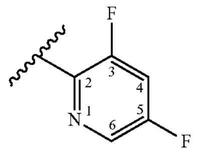 [SMILES: *c1ncc(F)cc1F]

The term "3-fluoropyridin-2-yl" refers to a moiety of structure

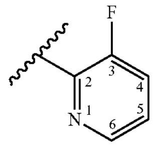

The term "5-fluoro-3-methylpyridin-2-yl" refers to a moiety of structure:

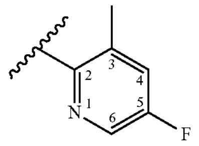 [SMILES: *c1ncc(F)cc1C]

The term "6-fluoropyridin-2-yl" refers to a moiety of structure:

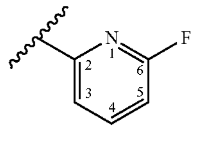 [SMILES: *c1cccc(F)n1]

The term "6-fluoro-4-methylpyridin-2-yl" refers to a moiety of structure:

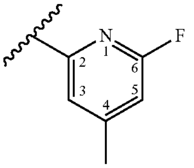 [SMILES: *c1cc(C)cc(F)n1]

The term "3-fluoro-5-methylpyridin-2-yl" refers to a moiety of structure:

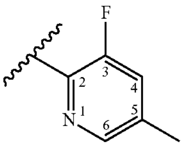 [SMILES: *c1ncc(C)cc1F]

The term "5-fluoropyridin-2-yl" refers to a moiety of structure:

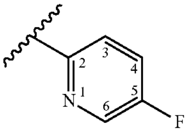 [SMILES: *c1ccc(F)cn1]

The term "4-fluoropyridin-3-yl" refers to a moiety of structure:

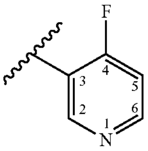 [SMILES: *c1cnccc1F]

The term "5-fluoropyrimidin-4-yl" refers to a moiety of structure:

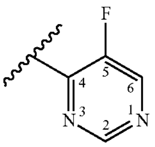 [SMILES: *c1ncncc1F]

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as $-C(O)N(R)-$ may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"p38 MAP Kinase inhibitor" is used herein to refer to a compound that exhibits an $IC_{50}$ with respect to p38 MAP Kinase activity of no more than about 100 μM and more typically not more than about 50 μM, as measured in the p38 MAP enzyme assays described generally herein. $IC_{50}$ is that concentration of inhibitor which reduces the activity of an enzyme (e.g., p38 MAP Kinase) to half-maximal level. Certain compounds disclosed herein have been discovered to exhibit inhibition against p38 MAP Kinase. In some embodiments, the compounds will exhibit an $IC_{50}$ with respect to p38 MAP Kinase of no more than about 1 nM. In some embodiments, the compounds will exhibit an $IC_{50}$ with respect to p38 MAP Kinase of no more than about 1 μM. In some embodiments, the compounds will exhibit an $IC_{50}$ with respect to p38 MAP Kinase of about 1 μM to about 50 μM. In certain embodiments, compounds will exhibit an $IC_{50}$ with respect to p38 MAP Kinase of no more than about 10 μM; in further embodiments, compounds will exhibit an $IC_{50}$ with respect to p38 MAP Kinase of no more than about 5 μM; in yet further embodiments, compounds will exhibit an $IC_{50}$ with respect to p38 MAP Kinase of not more than about 1 μM; in yet further embodiments, compounds will exhibit an $IC_{50}$ with respect to p38 MAP Kinase of not more than about 300 nM, as measured in the p38 MAP Kinase assay described herein.

The phrase "therapeutically effective" is intended to qualify the amount of active ingredients used in the treatment of a disease or disorder or on the effecting of a clinical endpoint.

As used herein, the term "therapeutic" or "therapeutic agent" or "pharmaceutically active agent" means an agent utilized to treat, combat, ameliorate, prevent or improve an unwanted condition or disease of a patient. In part, embodiments of the present invention are directed to the treatment of p38 MAP Kinase-mediated diseases.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 5 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The term "therapeutically acceptable" refers to those compounds, and a derivative thereof, which are suitable for use in contact with the tissues of patients without undue toxicity, irritation, and allergic response, are commensurate with a reasonable benefit/risk ratio, and are effective for their intended use.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound of embodiments herein, can include, but is not limited to, providing the compound into or onto the target tissue; providing the compound systemically to a patient by, e.g., intravenous injection whereby the therapeutic reaches the target tissue; providing the compound in the form of the encoding sequence thereof to the target tissue (e.g., by so-called gene-therapy techniques). "Administering" a composition may be accomplished by injection, topically, orally, or by any of these methods in combination with other known techniques.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent."

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

LIST OF ABBREVIATIONS

ACN acetonitrile
Boc tert-butyloxycarbonyl
Bu butyl
Bpy 2,2'-bipyridine
DCA dichloroacetic acid
DCI dicyclohexylcarbodiimide
DCM dichloromethane or methylenechloride
DIPEA diisopropylethylamine
DMA dimethylacetamide
DMAP 4-dimethylaminopyridine or N,N-dimethylaminopyridine
DME 1,2-dimethoxyethane
DMF N,N-dimethylformamide
DMSO dimethylsulfoxide
$CuBr_2$ copper(II)bromide
EDAC N-(3-dimethylaminopropyl)-N'-ethylcarbodiimide hydrochloride
eq. equivalents
Et ethyl
EtOAC ethyl acetate
EtOH ethanol
HPLC high pressure liquid chromatography
h hour(s)
IPA isopropyl alcohol
$K_2CO_3$ potassium carbonate
KOtBu potassium tert-butoxide
LAH lithium aluminum hydride
LC/MS liquid chromatography mass spectrometry
LC/MS/MS liquid chromatography tandem mass spectrometry
mCPBA m-chloroperbenzoic acid
Me methyl
MeCN acetonitrile
MeOH methanol
$MgSO_4$ magnesium sulfate
mL milliliter
mmol millimole NaH sodium hydride
$NaN(TMS)_2$ sodium bis(trimethylsilyl)amide
NCS n-chloro succinimide
NMR nuclear magnetic resonance
NMP N-methylpyrrolidone
Pd/C palladium on carbon
Ph phenyl
PPA polyphosphoric acid
TEA triethylamine
TFA trifluoroacetic acid
THF tetrahydrofuran
TOSMIC toluenesulfonylmethyl isocyanide
TSA p-toluenesulfonic acid.

Compounds and Crystalline Form Compounds

Embodiments herein are directed to compounds, crystalline forms of a compounds, and pharmaceutical compositions, certain of which have been found to inhibit p38 MAP Kinase, together with methods of synthesizing and using the compounds. Some embodiments include methods for the treatment of diseases in a patient by administering the compounds, crystalline forms of a compounds, and pharmaceutical compositions there as described herein.

Certain compounds and crystalline forms of compounds disclosed herein may possess useful p38 MAP Kinase inhibiting activity, and may be used in the treatment or prophylaxis of a disease or condition in which p38 MAP Kinase plays an active role. Thus, embodiments also provide pharmaceutical compositions comprising one or more compounds disclosed herein together with a pharmaceutically acceptable carrier, as well as methods of making and using the compounds and compositions. Certain embodiments provide methods for inhibiting p38 MAP kinase using compounds of embodiments herein. Other embodiments provide methods for treating a p38 MAP Kinase-mediated disorder in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of p38 MAP Kinase.

Also provided are embodiments wherein any embodiment herein may be combined with any one or more of the other embodiments, unless otherwise stated and provided the combination is not mutually exclusive.

Also provided is a compound chosen from the Examples disclosed herein. The compounds of embodiments herein may also refer to a derivative thereof, or a combination of the foregoing of the compounds of embodiments herein.

Conventional techniques for the preparation/isolation of individual enantiomers include chiral synthesis from a suitable enantioenriched or optically pure precursors or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of embodiments herein (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g., "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of its corresponding atropisomer) and stereoisomer-enriched mixtures, i.e. mixtures of atropisomers.

Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

The term "atropisomerism" refers to a type of isomerism resulting from hindered rotation around a single bond due to steric strain of the substituents. This phenomenon creates stereoisomers which display axial chirality.

The following scheme illustrates "atropisomerism" with reference to specific pyridinone-pyridine compounds of the invention:

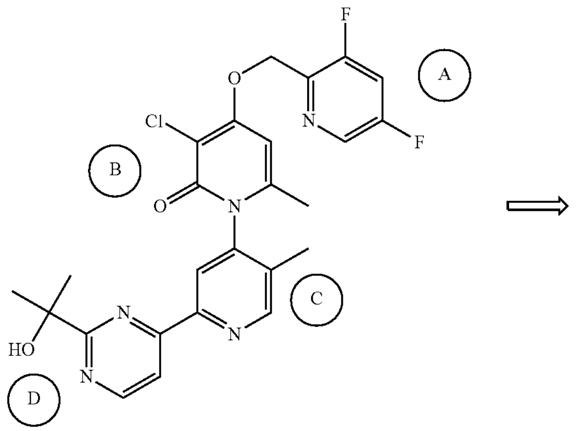

-continued

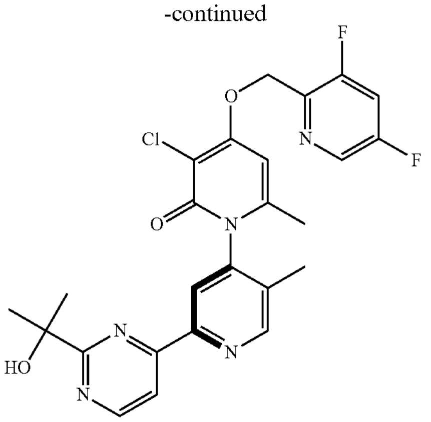

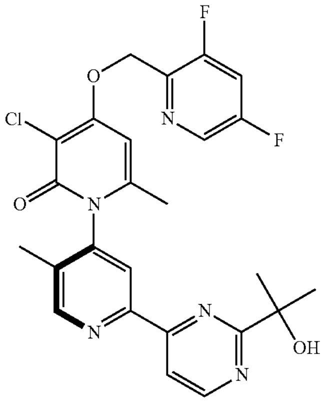

The bond between the B and C rings of the title compounds is hindered and does not allow for facile rotation. The steric strain barrier to rotation is sufficiently high such that individual conformers can be isolated. The compounds of the invention may also exist as atropisomers, i.e., chiral rotational isomers. The invention encompasses racemates, resolved atropisomers, and mixtures thereof. Atropisomers may be separated via supercritical fluid chromatography using a mobile phase of carbon dioxide and ethanol/methanol.

Atropisomers are generally stable but can often be equilibrated thermally. Atropisomers will have the same but opposite optical rotation. Each atropisomers may have different properties when bound to an enzyme or receptor with one isomer often being more potent than the other. Atropisomers are frequently used as pharmaceutical agents. Known examples include Vancomycin and derivatives.

The configuration of atropisomers can be described using the nomenclature (M)- and (P)- to describe the relative position of substituents as described in Bringmann, G. et. al., Angew. Chem. Int. Ed. 2005, 44, 5384 and references cited therein. Structures are designated as drawn but it is understood that either (P)- or (M)-isomers may be desirable and the methods described would be useful for the interconversion of either (P)- or (M)-stereoisomers.

The term "interconversion" or "conformational interconversion" refers to any change between the atropisomers of this disclosure, including but not limited to equilibration.

The term "equilibration" refers to a chemical reaction in which the forward and reverse ratio rates cancel out. Equilibration can be dynamic or static. A reaction in equilibrium need not contain equal parts reactant and product.

Suitable pharmaceutically acceptable acid addition salts of the compounds of embodiments herein may be prepared from an inorganic acid or an organic acid. All of these salts may be prepared by conventional means from the corresponding compound of embodiments herein by treating, for example, the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X−) is associated with the positive charge of the N atom. X− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X− is preferably an anion selected from chloride, bromide, iodide, sulphate, nitrate, acetate, maleate, oxalate, succinate or trifluoroacetate. More preferably X− is chloride, bromide, trifluoroacetate or methanesulphonate.

As used herein, an N-oxide is formed from the tertiary basic amines or imines present in the molecule, using a convenient oxidizing agent.

The compounds of embodiments herein may exist in both unsolvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethylsulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

Furthermore, it is specifically contemplated that in embodiments herein, more than one solvent molecule may be associated with one molecule of the compounds of embodiments herein, such as a dihydrate. Additionally, it is specifically contemplated that in embodiments herein less than one solvent molecule may be associated with one molecule of the compounds of embodiments herein, such as a hemihydrate. Furthermore, solvates of embodiments herein are contemplated as solvates of compounds of embodiments herein that retain the biological effectiveness of the non-solvate form of the compounds.

Embodiments herein also includes isotopically-labeled compounds of embodiments herein, wherein one or more atoms is replaced by an atom having the same atomic number, but an atomic mass or mass number different from the atomic mass or mass number usually found in nature. Examples of isotopes suitable for inclusion in the compounds of embodiments herein include isotopes of hydrogen, such as $^{2}H$ and $^{3}H$, carbon, such as $^{11}C$, $^{13}C$ and $^{14}C$, chlorine, such as $^{31}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of embodiments herein, for example, those incorporating a radioactive isotope, are useful in drug and/or substrate tissue distribution studies. The radioactive isotopes tritium, $^{3}H$, and carbon-14, $^{14}C$, are particularly useful for this purpose in view of their ease of incorporation and ready means of detection. Substitution with heavier isotopes such as deuterium, 2H, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of embodiments herein can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of embodiments herein. As used herein, the term deuterated derivative embraces compounds of embodiments herein where in a particular position at least one hydrogen atom is replaced by deuterium. Deuterium (D or $^{2}H$) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of embodiments herein has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In some embodiments, the isotopic enrichment factor is at least 5000 (75% deuterium). In some embodiments, the isotopic enrichment factor is at least 6333.3 (95% deuterium incorporation). In some embodiments, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known to one of ordinary skilled in the art, including mass spectrometry (MS) and nuclear magnetic resonance (NMR).

Prodrugs of the compounds described herein are also within the scope of embodiments herein. Thus, certain derivatives of the compounds of embodiments herein, which derivatives may have little or no pharmacological activity themselves, when administered into or onto the body may be converted into compounds of embodiments herein having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with embodiments herein can, for example, be produced by replacing appropriate functionalities present in the compounds of embodiments herein with certain moieties known to those skilled in the art as 'pro-moieties' as described, for example, in Design of Prodrugs by H. Bundgaard (Elsevier, 1985).

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present disclosure provides a compound having the structure of Formula (P)-Ia:

(P)-Ia

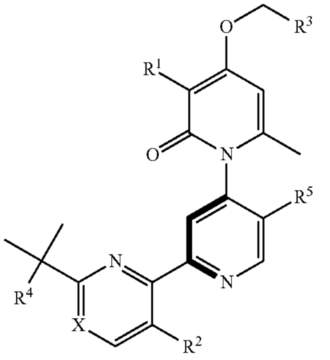

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^3$ is selected from the group consisting of

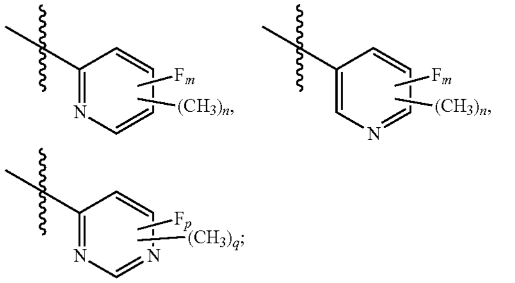

$R^4$ is selected from the group consisting of H, methyl, OH, and —$OCH_3$;

$R^5$ is H or $C_1$-$C_3$ alkyl;

m is 1 or 2;

n is 0 or 1;

p is 1;

q is 0 or 1; or a derivative thereof.

In certain embodiments, $R^3$ selected from the group consisting of 3,5-difluoropyridin-2-yl, 3-fluoropyridin-2-yl, 5-fluoro-3-methylpyridin-2-yl, 6-fluoropyridin-2-yl, 6-fluoro-4-methylpyridin-2-yl, 3-fluoro-5-methylpyridin-2-yl, and 5-fluoropyridin-2-yl.

Some embodiments are directed to a compound having the structure of Formula (P)-IIa:

(P)-IIa

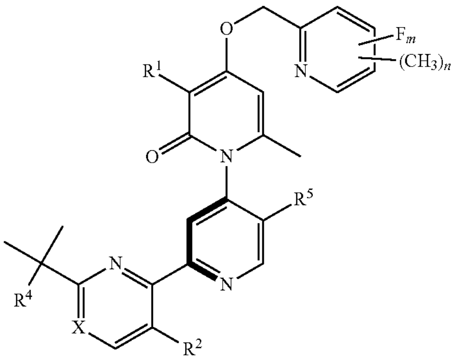

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^4$ is selected from the group consisting of H, methyl, OH, and —$OCH_3$;

$R^5$ is H or $C_1$-$C_3$ alkyl;

m is 1 or 2;

n is 0 or 1; or a derivative thereof.

Non-limiting examples of Formula (P)-IIa compounds include the following compounds, or a derivative thereof:

| No. | Structure | Compound Name |
|---|---|---|
| 1a | 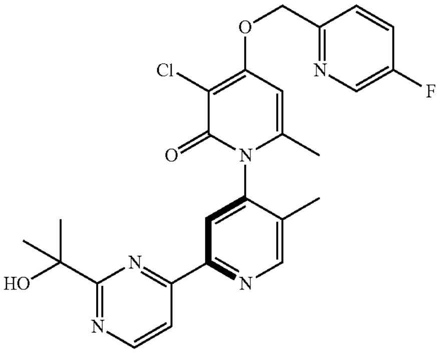 | (P)-3-chloro-4-((5-fluoropyridin-2-yl)methoxy)-2'-(2-(2-hydroxypropan-2-yl)pyrimidin-4-yl)-5',6-dimethyl-2H-[1,4'-bipyridin]-2-one |

-continued

| No. | Structure | Compound Name |
|---|---|---|
| 2a | 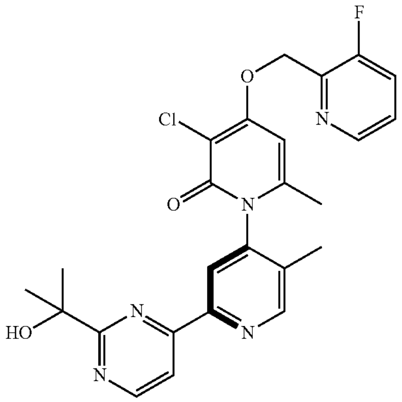 | (P)-3-chloro-4-((3-fluoropyridin-2-yl)methoxy)-2'-(2-(2-hydroxypropan-2-yl)pyrimidin-4-yl)-5',6-dimethyl-2H-[1,4'-bipyridin]-2-one |
| 3a | 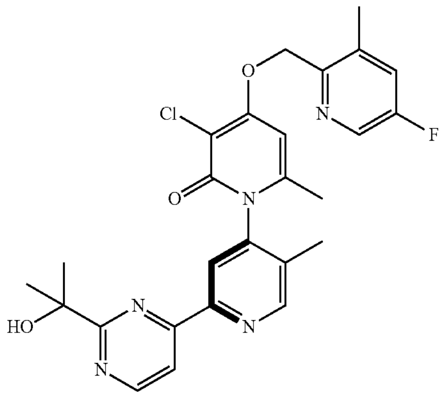 | (P)-3-chloro-4-((5-fluoro-3-methylpyridin-2-yl)methoxy)-2'-(2-(2-hydroxypropan-2-yl)pyrimidin-4-yl)-5',6-dimethyl-2H-[1,4 -bipyridin]-2-one |
| 4a | 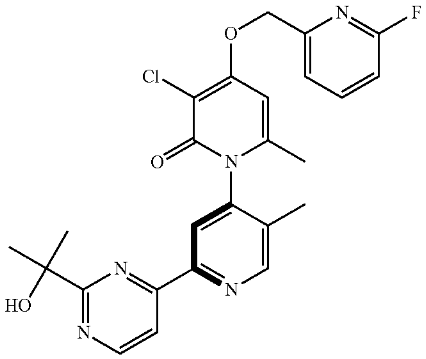 | (P)-3-chloro-4-((6-fluoropyridin-2-yl)methoxy)-2'-(2-(2-hydroxypropan-2-yl)pyrimidin-4-yl)-5',6-dimethyl-2H-[1,4'-bipyridin]-2-one |
| 5a | 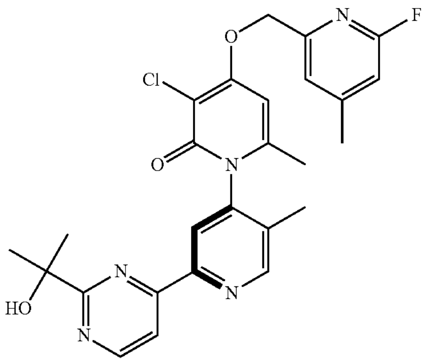 | (P)-3-chloro-4-((6-fluoro-4-methylpyridin-2-yl)methoxy)-2'-(2-(2-hydroxypropan-2-yl)pyrimidin-4-yl)-5',6-dimethyl-2H-[1,4'-bipyridin]-2-one |

-continued

| No. | Structure | Compound Name |
|---|---|---|
| 6a | 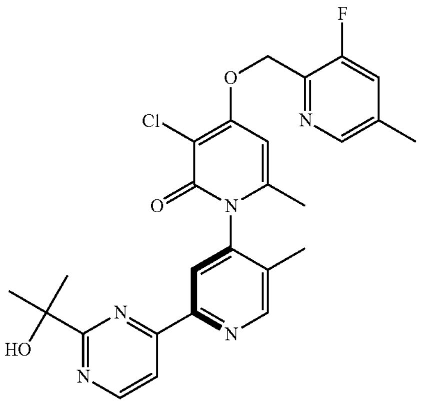 | (P)-3-chloro-4-((3-fluoro-5-methylpyridin-2-yl)methoxy)-2'-(2-(2-hydroxypropan-2-yl)pyrimidin-4-yl)-5',6-dimethyl-2H-[1,4'-bipyridin]-2-one |
| 7a | 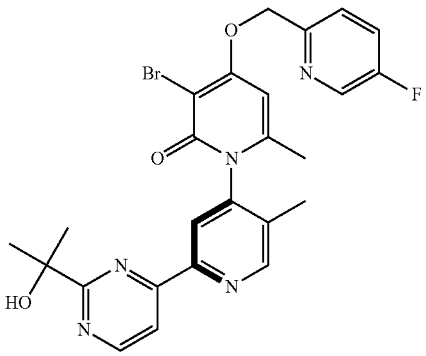 | (P)-3-bromo-4-((5-fluoropyridin-2-yl)methoxy)-2'-(2-(2-hydroxypropan-2-yl)pyrimidin-4-yl)-5',6-dimethyl-2H-[1,4'-bipyridin]-2-one |
| 8a | 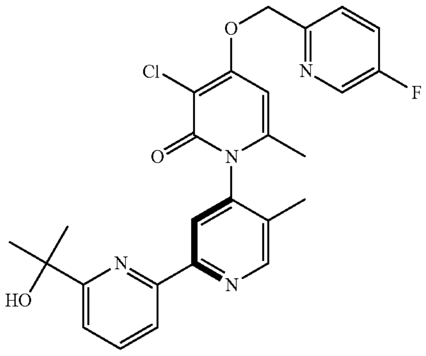 | (P)-3-chloro-4-((5-fluoropyridin-2-yl)methoxy)-6''-(2-hydroxypropan-2-yl)-5',6-dimethyl-2H-[1,4':2',2''-terpyridin]-2-one |
| 9a | 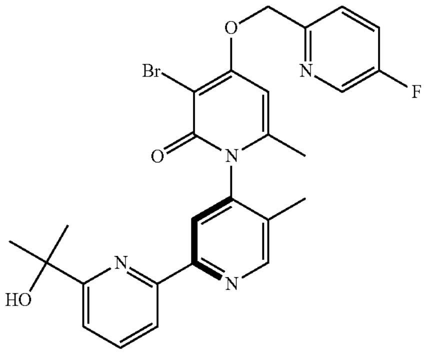 | (P)-3-bromo-4-((5-fluoropyridin-2-yl)methoxy)-6''-(2-hydroxypropan-2-yl)-5',6-dimethyl-2H-[1,4':2',2''-terpyridin]-2-one |

-continued

| No. | Structure | Compound Name |
|---|---|---|
| 10a | 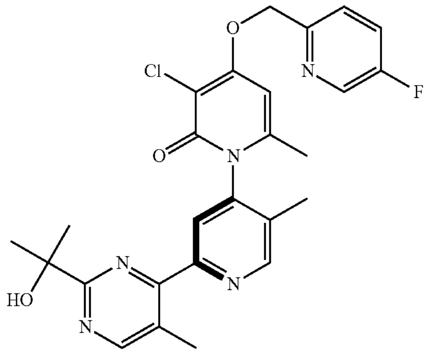 | (P)-3-chloro-4-((5-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 11a | 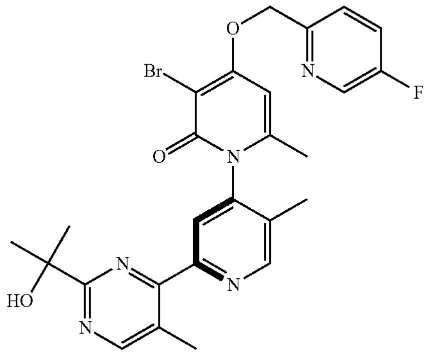 | (P)-3-bromo-4-((5-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 12a | 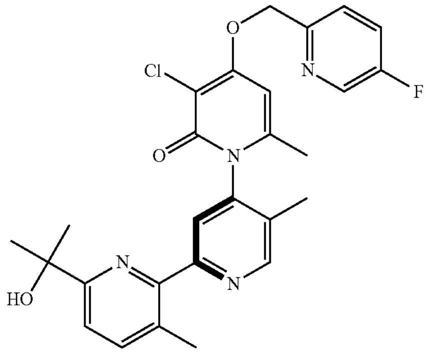 | (P)-3-chloro-4-((5-fluoropyridin-2-yl)methoxy)-6''-(2-hydroxypropan-2-yl)-3'',5',6-trimethyl-2H-[1,4':2',2''-terpyridin]-2-one |
| 13a | 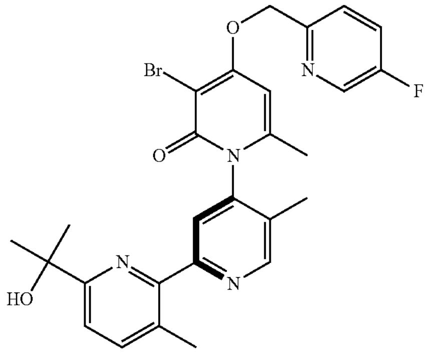 | (P)-3-bromo-4-((5-fluoropyridin-2-yl)methoxy)-6''-(2-hydroxypropan-2-yl)-3'',5',6-trimethyl-2H-[1,4':2',2''-terpyridin]-2-one |

-continued
| No. | Structure | Compound Name |
| --- | --- | --- |
| 14a | 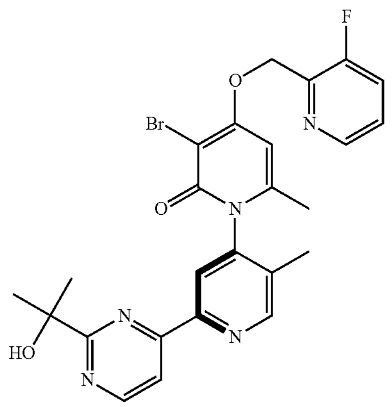 | (P)-3-bromo-4-((3-fluoropyridin-2-yl)methoxy)-2'-(2-(2-hydroxypropan-2-yl)pyrimidin-4-yl)-5',6-dimethyl-2H-[1,4'-bipyridin]-2-one |
| 15a | 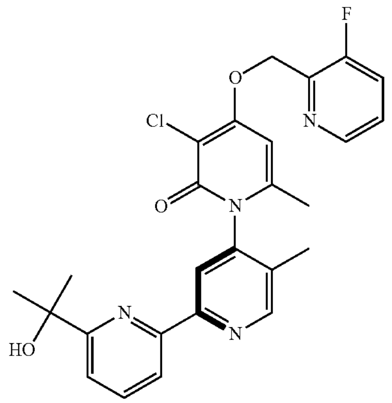 | (P)-3-chloro-4-((3-fluoropyridin-2-yl)methoxy)-6''-(2-hydroxypropan-2-yl)-5',6-dimethyl-2H-[1,4':2',2''-terpyridin]-2-one |
| 16a | 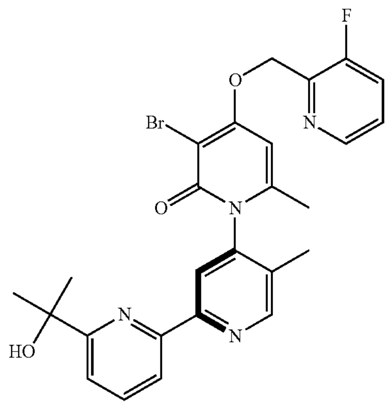 | (P)-3-bromo-4-((3-fluoropyridin-2-yl)methoxy)-6''-(2-hydroxypropan-2-yl)-5',6-dimethyl-2H-[1,4':2',2''-terpyridin]-2-one |

-continued
| No. | Structure | Compound Name |
| --- | --- | --- |
| 17a | 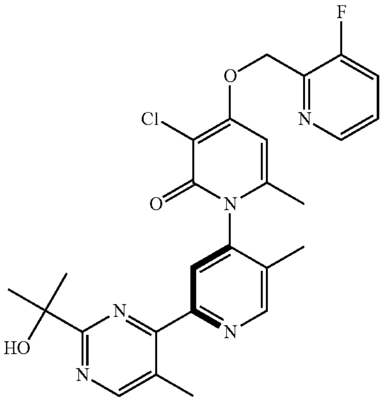 | (P)-3-chloro-4-((3-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 18a | 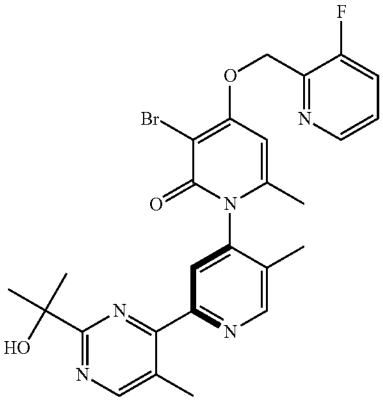 | (P)-3-bromo-4-((3-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 19a | 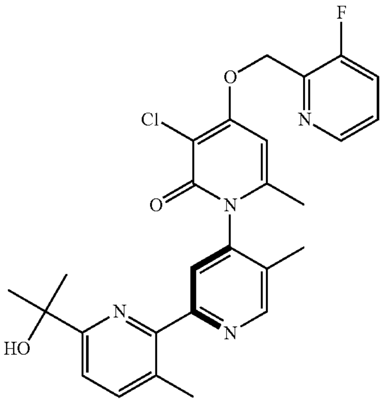 | (P)-3-chloro-4-((3-fluoropyridin-2-yl)methoxy)-6''-(2-hydroxypropan-2-yl)-3'',5',6-trimethyl-2H-[1,4':2',2''-terpyridin]-2-one |

-continued
| No. | Structure | Compound Name |
| --- | --- | --- |
| 20a | 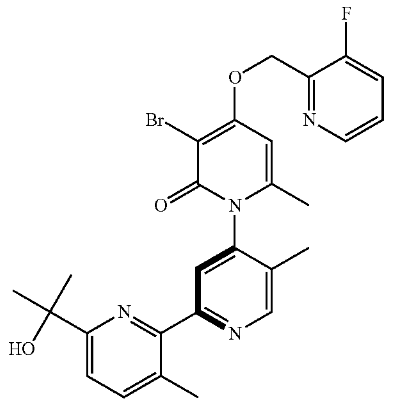 | (P)-3-bromo-4-((3-fluoropyridin-2-yl)methoxy)-6''-(2-hydroxypropan-2-yl)-3'',5',6-trimethyl-2H-[1,4':2',2''-terpyridin]-2-one |
| 21a | 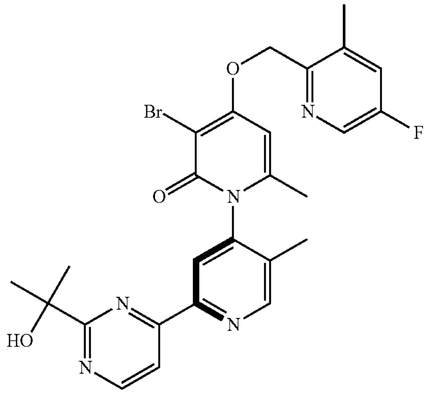 | (P)-3-bromo-4-((5-fluoro-3-methylpyridin-2-yl)methoxy)-2'-(2-(2-hydroxypropan-2-yl)pyrimidin-4-yl)-5',6-dimethyl-2H-[1,4'-bipyridin]-2-one |
| 22a | 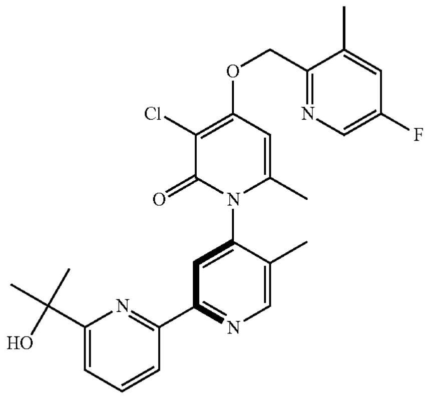 | (P)-3-chloro-4-((5-fluoro-3-methylpyridin-2-yl)methoxy)-6''-(2-hydroxypropan-2-yl)-5',6-dimethyl-2H-[1,4':2',2''-terpyridin]-2-one |

-continued
| No. | Structure | Compound Name |
| --- | --- | --- |
| 23a | 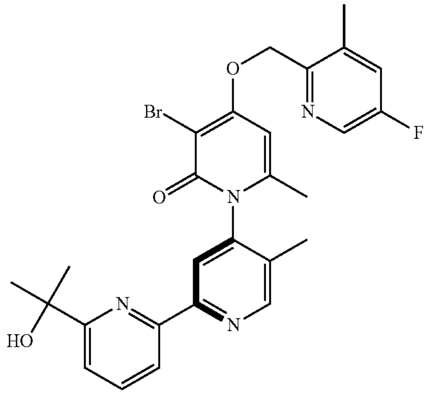 | (P)-3-bromo-4-((5-fluoro-3-methylpyridin-2-yl)methoxy)-6''-(2-hydroxypropan-2-yl)-5',6-dimethyl-2H-[1,4':2',2''-terpyridin]-2-one |
| 24a | 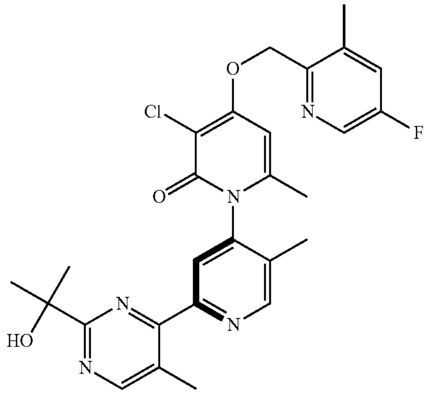 | (P)-3-chloro-4-((5-fluoro-3-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 25a | 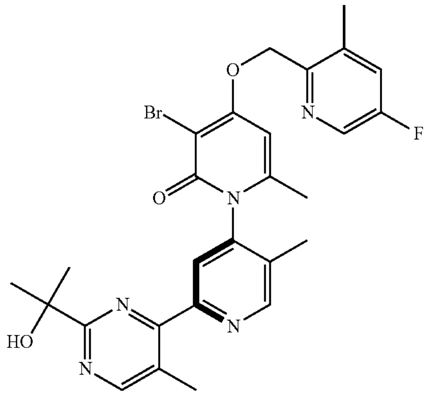 | (P)-3-bromo-4-((5-fluoro-3-methylpyridin-2-yl)methoxy)-2'-(2-(2-hydroxypropan-2-yl)-5-methylpyrimidin-4-yl)-5',6-dimethyl-2H-[1,4'-bipyridin]-2-one |

-continued

| No. | Structure | Compound Name |
|---|---|---|
| 26a | 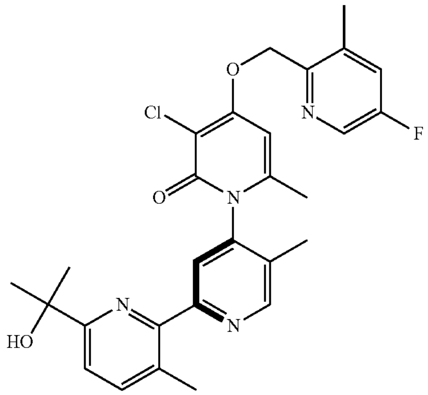 | (P)-3-chloro-4-((5-fluoro-3-methylpyridin-2-yl)methoxy)-6''-(2-hydroxypropan-2-yl)-3'',5',6-trimethyl-2H-[1,4':2',2''-terpyridin]-2-one |
| 27a | 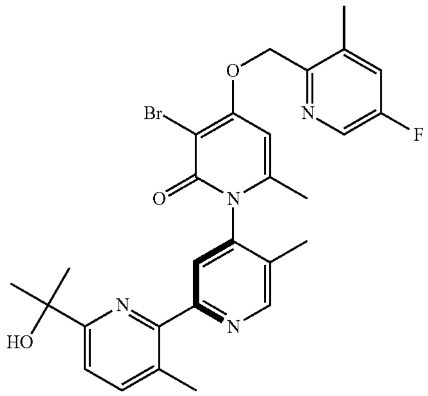 | (P)-3-bromo-4-((5-fluoro-3-methylpyridin-2-yl)methoxy)-6''-(2-hydroxypropan-2-yl)-3'',5',6-trimethyl-2H-[1,4':2',2''-terpyridin]-2-one |
| 28a | 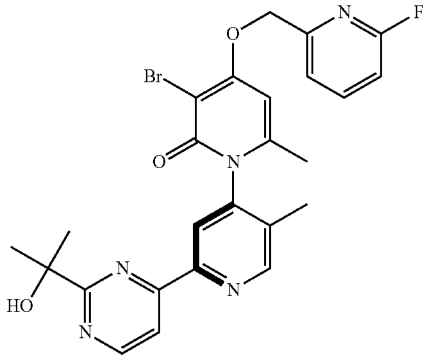 | (P)-3-bromo-4-((6-fluoropyridin-2-yl)methoxy)-2'-(2-(2-hydroxypropan-2-yl)pyrimidin-4-yl)-5',6-dimethyl-2H-[1,4'-bipyridin]-2-one |
| 29a | 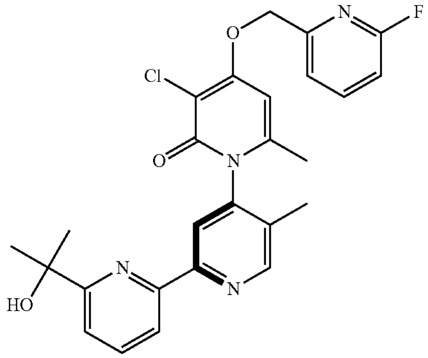 | (P)-3-chloro-4-((6-fluoropyridin-2-yl)methoxy)-6''-(2-hydroxypropan-2-yl)-5',6-dimethyl-2H-[1,4':2',2''-terpyridin]-2-one |

-continued

| No. | Structure | Compound Name |
| --- | --- | --- |
| 30a | 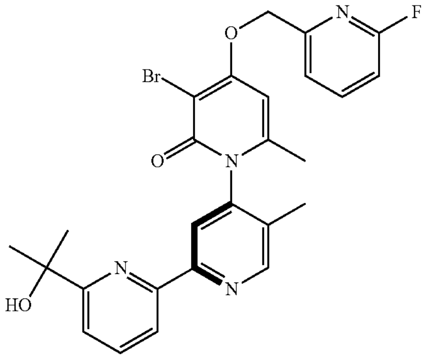 | (P)-3-bromo-4-((6-fluoropyridin-2-yl)methoxy)-6''-(2-hydroxypropan-2-yl)-5',6-dimethyl-2H-[1,4':2',2''-terpyridin]-2-one |
| 31a | 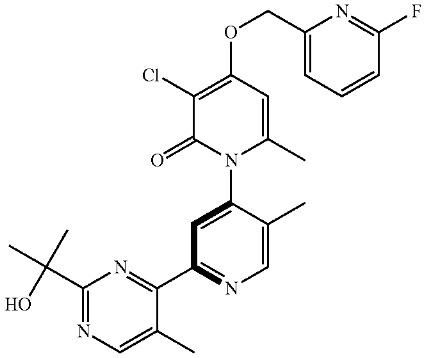 | (P)-3-chloro-4-((6-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 32a | 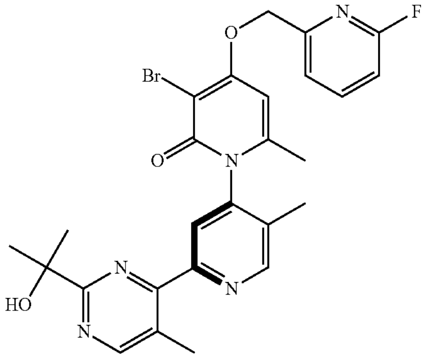 | (P)-3-bromo-4-((6-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 33a | 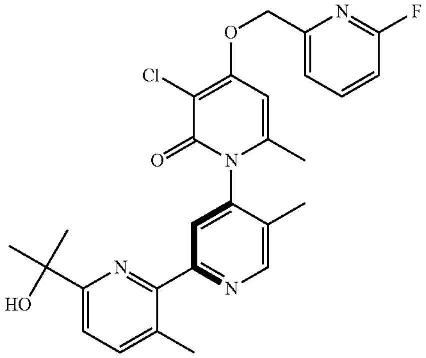 | (P)-3-chloro-4-((6-fluoropyridin-2-yl)methoxy)-6''-(2-hydroxypropan-2-yl)-3'',5',6-trimethyl-2H-[1,4':2',2''-terpyridin]-2-one |

-continued

| No. | Structure | Compound Name |
| --- | --- | --- |
| 34a | 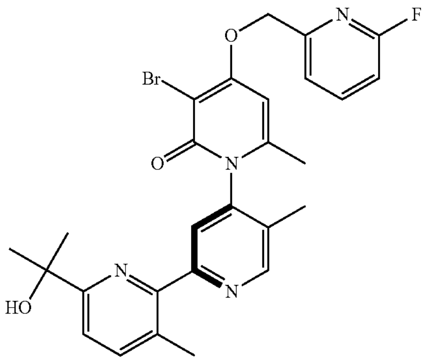 | (P)-3-bromo-4-((6-fluoropyridin-2-yl)methoxy)-6''-(2-hydroxypropan-2-yl)-3'',5',6-trimethyl-2H-[1,4':2',2''-terpyridin]-2-one |
| 35a | 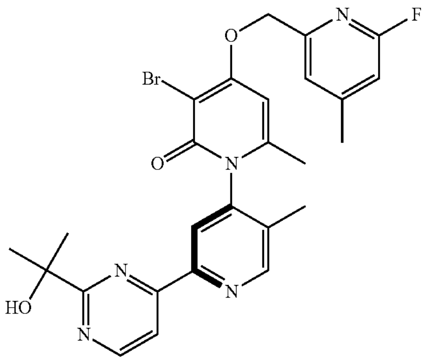 | (P)-3-bromo-4-((6-fluoro-4-methylpyridin-2-yl)methoxy)-2'-(2-(2-hydroxypropan-2-yl)pyrimidin-4-yl)-5',6-dimethyl-2H-[1,4'-bipyridin]-2-one |
| 36a | 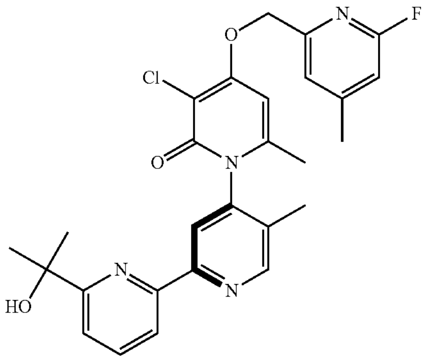 | (P)-3-chloro-4-((6-fluoro-4-methylpyridin-2-yl)methoxy)-6''-(2-hydroxypropan-2-yl)-5',6-dimethyl-2H-[1,4':2',2''-terpyridin]-2-one |
| 37a | 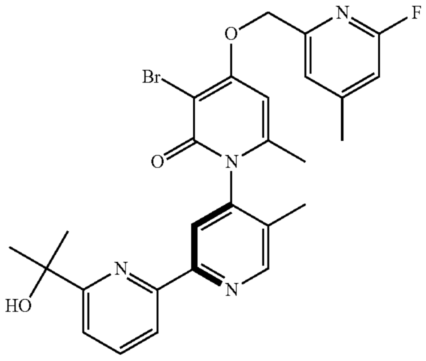 | (P)-3-bromo-4-((6-fluoro-4-methylpyridin-2-yl)methoxy)-6''-(2-hydroxypropan-2-yl)-5',6-dimethyl-2H-[1,4':2',2''-terpyridin]-2-one |

-continued

| No. | Structure | Compound Name |
|---|---|---|
| 38a | 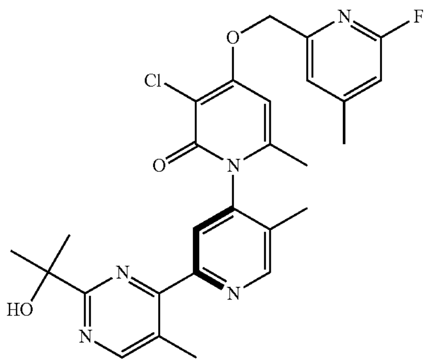 | (P)-3-chloro-4-((6-fluoro-4-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 39a | 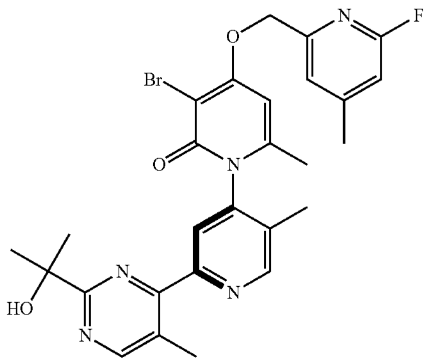 | (P)-3-bromo-4-((6-fluoro-4-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 40a | 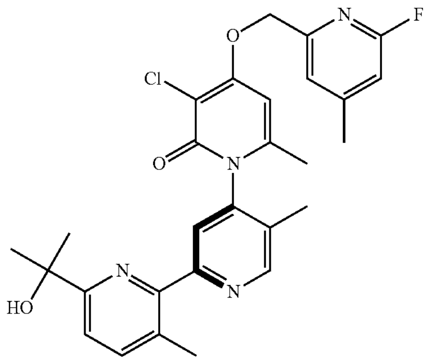 | (P)-3-chloro-4-((6-fluoro-4-methylpyridin-2-yl)methoxy)-6'-(2-hydroxypropan-2-yl)-3'',5',6-trimethyl-2H-[1,4':2',2''-terpyridin]-2-one |
| 41a | 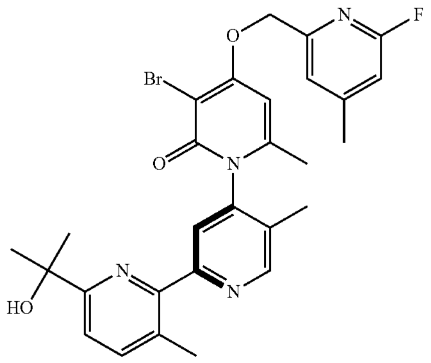 | (P)-3-bromo-4-((6-fluoro-4-methylpyridin-2-yl)methoxy)-6''-(2-hydroxypropan-2-yl)-3'',5',6-trimethyl-2H-[1,4':2',2''-terpyridin]-2-one |

-continued
| No. | Structure | Compound Name |
|---|---|---|
| 42a | 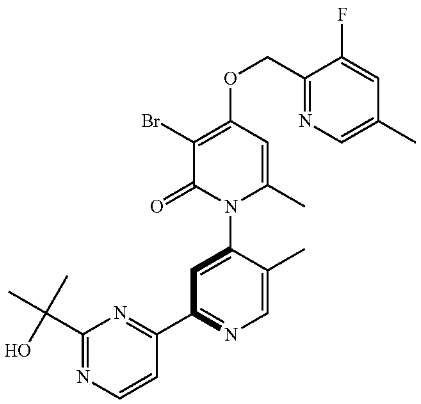 | (P)-3-bromo-4-((3-fluoro-5-methylpyridin-2-yl)methoxy)-2'-(2-(2-hydroxypropan-2-yl)pyrimidin-4-yl)-5',6-dimethyl-2H-[1,4'-bipyridin]-2-one |
| 43a | 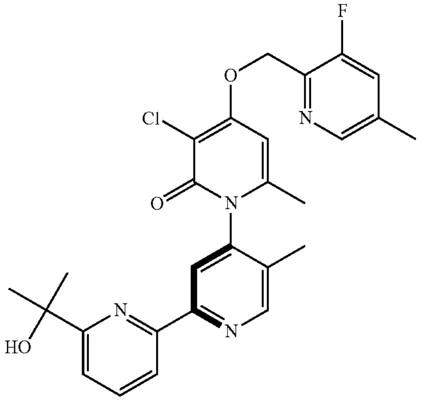 | (P)-3-chloro-4-((3-fluoro-5-methylpyridin-2-yl)methoxy)-6''-(2-hydroxypropan-2-yl)-5',6-dimethyl-2H-[1,4':2',2''-terpyridin]-2-one |
| 44a | 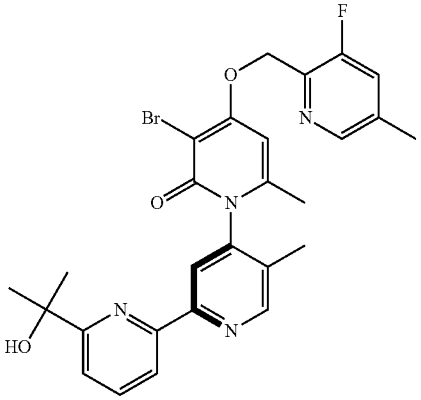 | (P)-3-bromo-4-((3-fluoro-5-methylpyridin-2-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 45a | 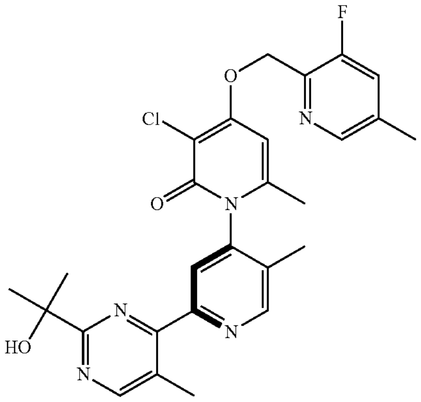 | (P)-3-chloro-4-((3-fluoro-5-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 46a | 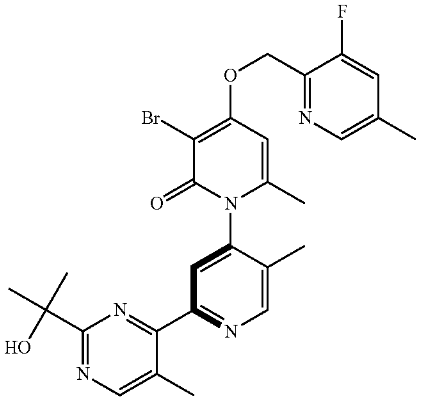 | (P)-3-bromo-4-((3-fluoro-5-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 47a | 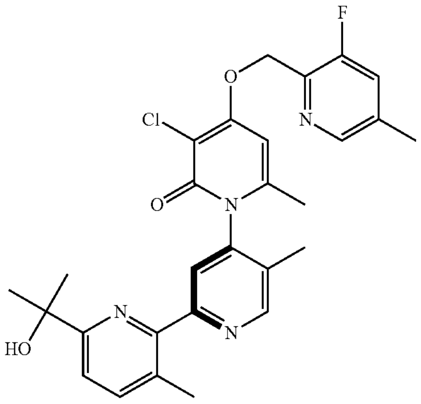 | (P)-3-chloro-4-((3-fluoro-5-methylpyridin-2-yl)methoxy)-6''-(2-hydroxypropan-2-yl)-3'',5',6-trimethyl-2H-[1,4':2',2''-terpyridin]-2-one |

-continued

| No. | Structure | Compound Name |
|---|---|---|
| 48a | 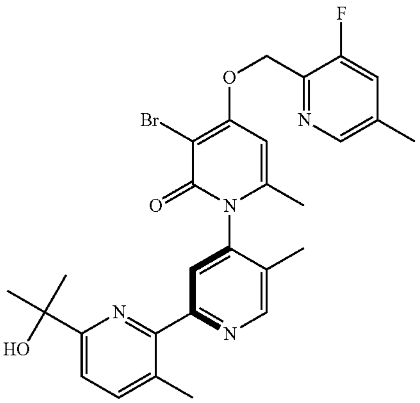 | (P)-3-bromo-4-((3-fluoro-5-methylpyridin-2-yl)methoxy)-6''-(2-hydroxypropan-2-yl)-3'',5',6-trimethyl-2H-[1,4':2',2''-terpyridin]-2-one |

Some embodiments are directed to a compound having the structure of Formula (P)-IIIa:

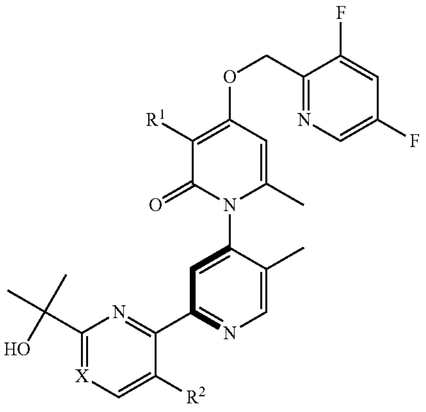

(P)-IIIa wherein:

X is CH or N;

$R^1$ is chloro or bromo;

$R^2$ is H or methyl; and a derivative thereof.

Non-limiting examples of Formula (P)-IIIa compounds include the following compounds, or a derivative thereof:

| No. | Structure | Compound Name |
|---|---|---|
| 49a | 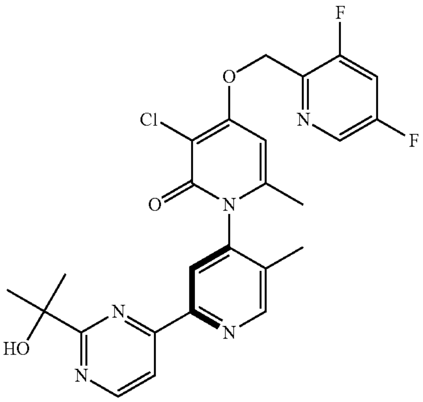 | (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one |

-continued
| No. | Structure | Compound Name |
| --- | --- | --- |
| 50a | 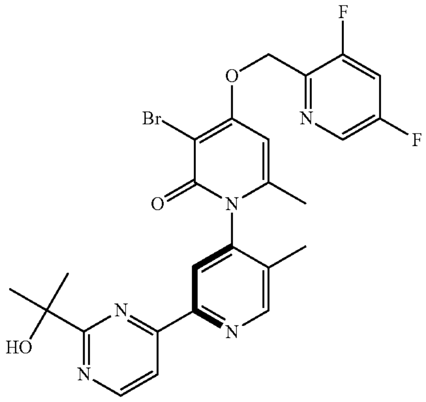 | (P)-3-bromo-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one |
| 51a | 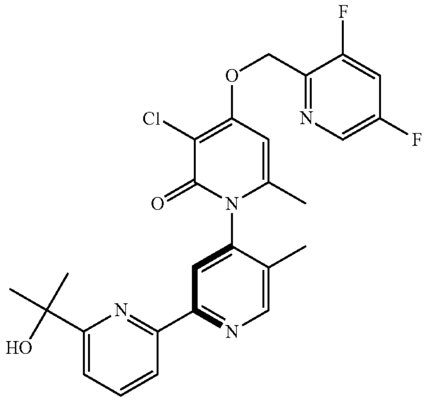 | (P)-3-chloro-4-((3,5-difluoropyridin-2-yl)methoxy)-6''-(2-hydroxypropan-2-yl)-5',6-dimethyl-2H-[1,4':2',2''-terpyridin]-2-one |
| 52a | 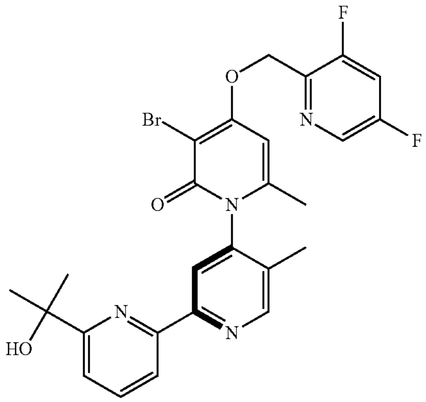 | (P)-3-bromo-4-((3,5-difluoropyridin-2-yl)methoxy)-6''-(2-hydroxypropan-2-yl)-5',6-dimethyl-2H-[1,4':2',2''-terpyridin]-2-one |

-continued
| No. | Structure | Compound Name |
| --- | --- | --- |
| 53a | 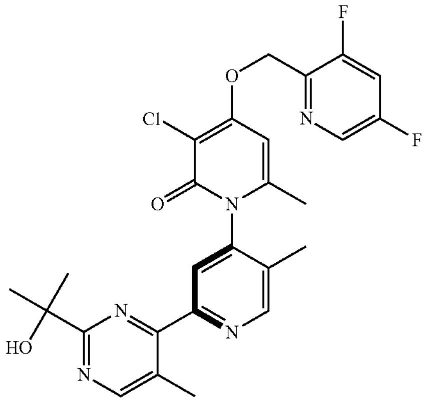 | (P)-3-chloro-4-((3,5-difluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 54a | 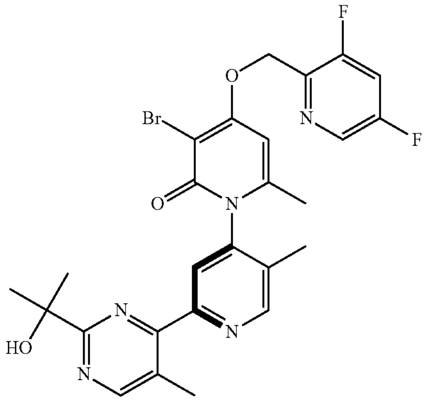 | (P)-3-bromo-4-((3,5-difluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 55a | 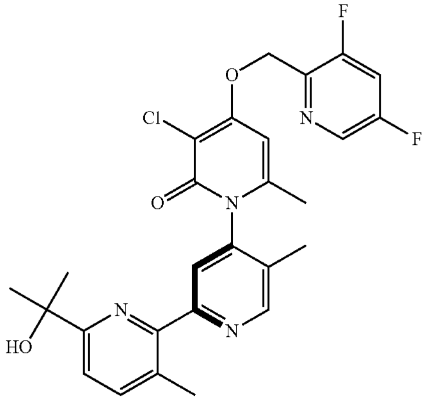 | (P)-3-chloro-4-((3,5-difluoropyridin-2-yl)methoxy)-6''-(2-hydroxypropan-2-yl)-3'',5',6-trimethyl-2H-[1,4':2',2''-terpyridin]-2-one |

-continued

| No. | Structure | Compound Name |
|---|---|---|
| 56a | 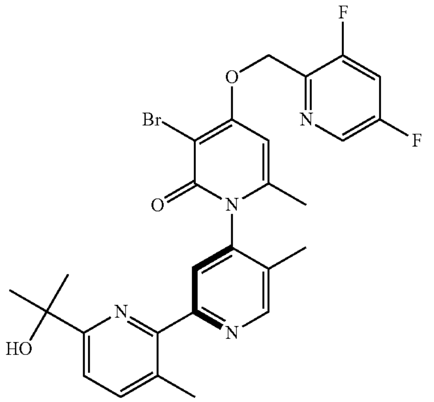 | (P)-3-bromo-4-((3,5-difluoropyridin-2-yl)methoxy)-6''-(2-hydroxypropan-2-yl)-3'',5',6-trimethyl-2H-[1,4':2',2''-terpyridin]-2-one |

Some embodiments are directed to a compound having the structure of Formula (P)-IVa:

(P)-IVa

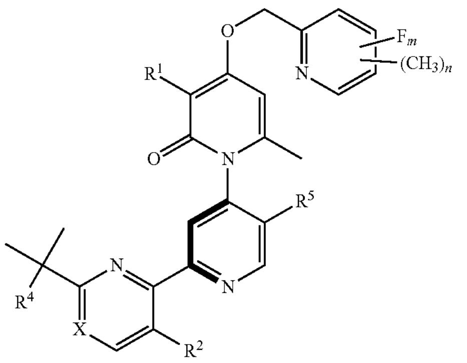

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^4$ is selected from the group consisting of H, methyl, OH, and —$OCH_3$;

$R^5$ is H or $C_1$-$C_3$ alkyl;

m is 1 or 2;

n is 0 or 1; or a derivative thereof.

Some embodiments are directed to a a compound having the structure of Formula (P)-Va:

(P)-Va

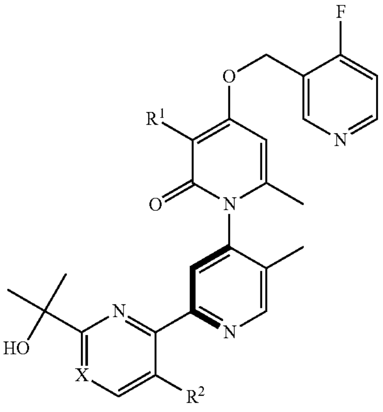

wherein:

X is CH or N;

$R^1$ is chloro or bromo;

$R^2$ is H or methyl; or a derivative thereof.

Non-limiting examples of Formula (P)-Va compounds include the following compounds, or a derivative thereof.

| No. | Structure | Compound Name |
|---|---|---|
| 57a | 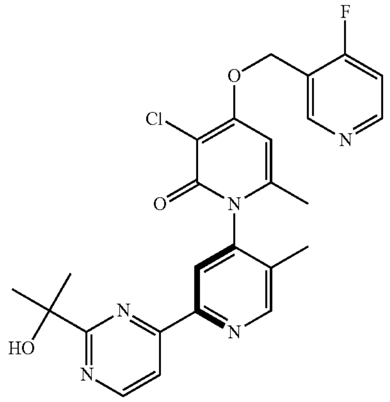 | (P)-3-chloro-4-((4-fluoropyridin-3-yl)methoxy)-2'-(2-(2-hydroxypropan-2-yl)pyrimidin-4-yl)-5',6-dimethyl-2H-[1,4'-bipyridin]-2-one |
| 58a | 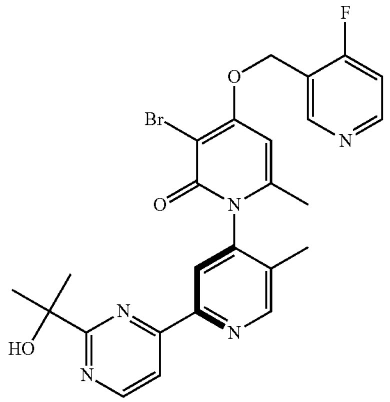 | (P)-3-bromo-4-((4-fluoropyridin-3-yl)methoxy)-2'-(2-(2-hydroxypropan-2-yl)pyrimidin-4-yl)-5',6-dimethyl-2H-[1,4'-bipyridin]-2-one |
| 59a | 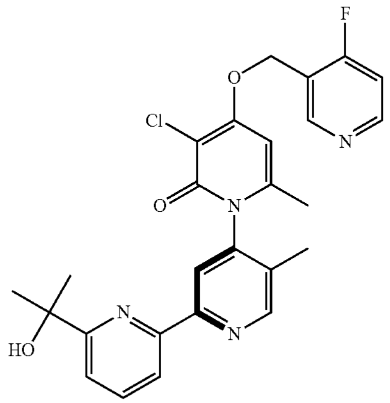 | (P)-3-chloro-4-((4-fluoropyridin-3-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 60a | 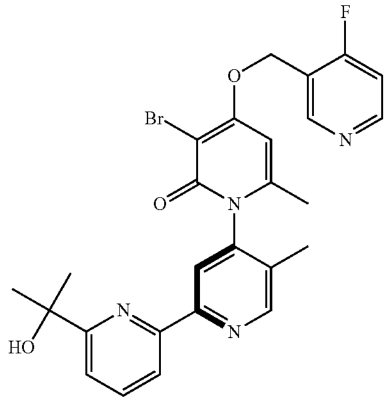 | (P)-3-bromo-4-((4-fluoropyridin-3-yl)methoxy)-6"-(2-hydroxypropan-2-yl)-5',6-dimethyl-2H-[1,4':2',2"-terpyridin]-2-one |
| 61a | 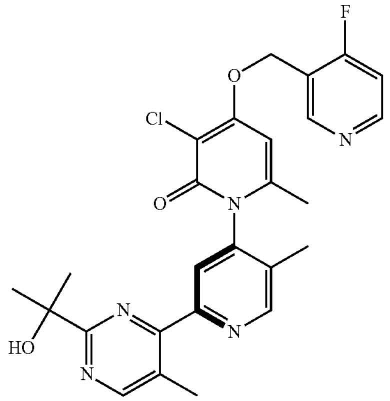 | (P)-3-chloro-4-((4-fluoropyridin-3-yl)methoxy)-2'-(2-(2-hydroxypropan-2-yl)-5-methylpyrimidin-4-yl)-5',6-dimethyl-2H-[1,4'-bipyridin]-2-one |
| 62a | 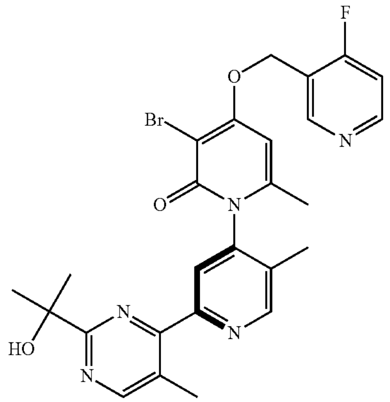 | (P)-3-bromo-4-((4-fluoropyridin-3-yl)methoxy)-2'-(2-(2-hydroxypropan-2-yl)-5-methylpyrimidin-4-yl)-5',6-dimethyl-2H-[1,4'-bipyridin]-2-one |

-continued

| No. | Structure | Compound Name |
|---|---|---|
| 63a | 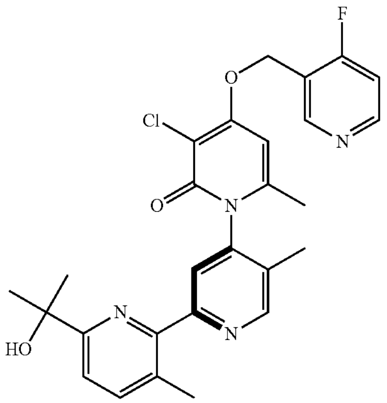 | (P)-3-chloro-4-((4-fluoropyridin-3-yl)methoxy)-6''-(2-hydroxypropan-2-yl)-3'',5',6-trimethyl-2H-[1,4':2',2''-terpyridin]-2-one |
| 64a | 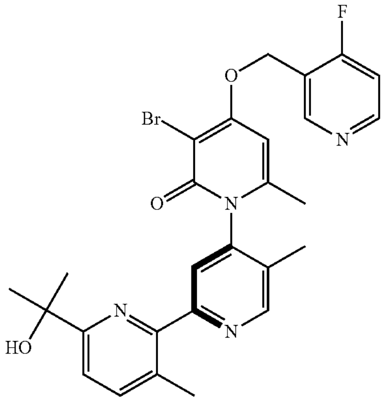 | (P)-3-bromo-4-((4-fluoropyridin-3-yl)methoxy)-6''-(2-hydroxypropan-2-yl)-3'',5',6-trimethyl-2H-[1,4':2',2''-terpyridin]-2-one |

Some embodiments are directed to a compound having the structure of Formula (P)-VIa:

(P)-VIa

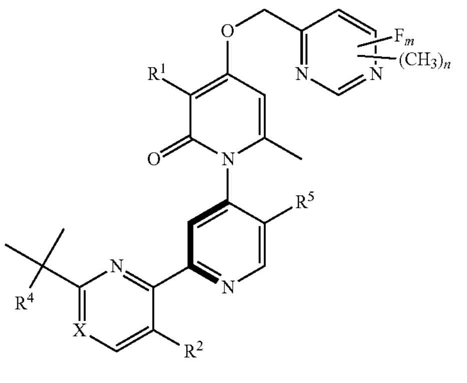

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^4$ is selected from the group consisting of H, methyl, OH, and —$OCH_3$;

$R^5$ is H or $C_1$-$C_3$ alkyl;

p is 1;

q is 0 or 1; or a derivative thereof.

Some embodiments are directed to a compound having the structure of Formula (P)-VIIa:

(P)-VIIa

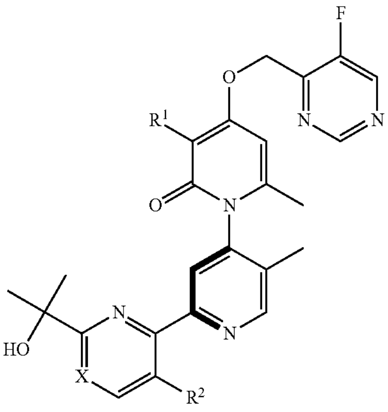

wherein:

X is CH or N;

$R^1$ is chloro or bromo;

$R^2$ is —H or methyl; or a derivative thereof.

Non-limiting examples of Formula (P)-VIIa compounds include the following compounds, or a derivative thereof.

| No. | Structure | Compound Name |
|---|---|---|
| 65a | 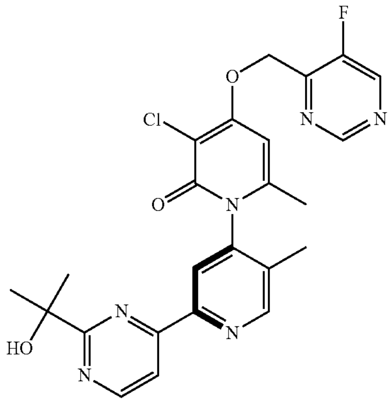 | (P)-3-chloro-4-((5-fluoropyrimidin-4-yl)methoxy)-2'-(2-(2-hydroxypropan-2-yl)pyrimidin-4-yl)-5',6-dimethyl-2H-[1,4'-bipyridin]-2-one |
| 66a | 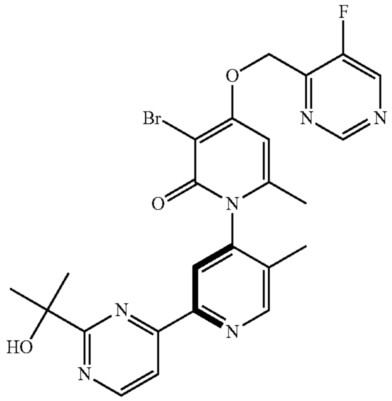 | (P)-3-bromo-4-((5-fluoropyrimidin-4-yl)methoxy)-2'-(2-(2-hydroxypropan-2-yl)pyrimidin-4-yl)-5',6-dimethyl-2H-[1,4'-bipyridin]-2-one |
| 67a | 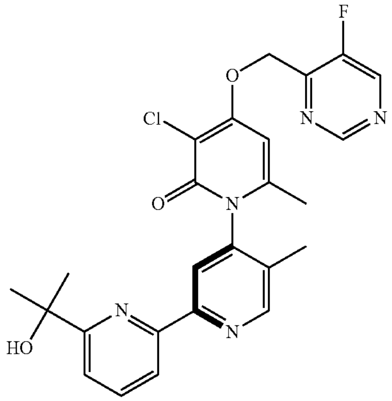 | (P)-3-chloro-4-((5-fluoropyrimidin-4-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 68a | 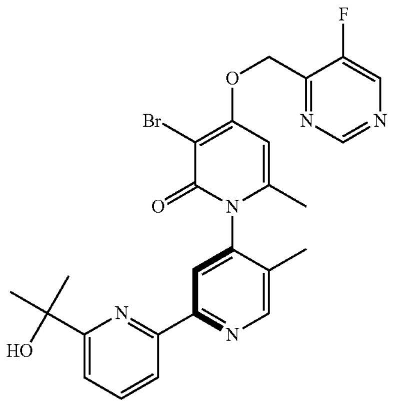 | (P)-3-bromo-4-((5-fluoropyrimidin-4-yl)methoxy)-6''-(2-hydroxypropan-2-yl)-5',6-dimethyl-2H-[1,4':2',2''-terpyridin]-2-one |
| 69a | 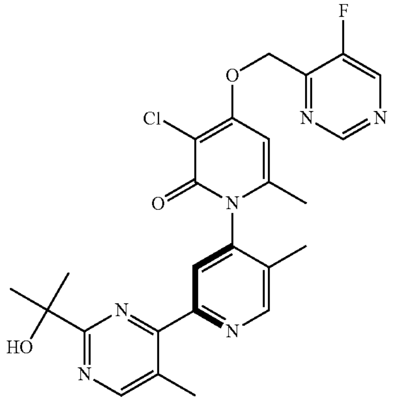 | (P)-3-chloro-4-((5-fluoropyrimidin-4-yl)methoxy)-2'-(2-(2-hydroxypropan-2-yl)-5-methylpyrimidin-4-yl)-5',6-dimethyl-2H-[1,4'-bipyridin]-2-one |
| 70a | 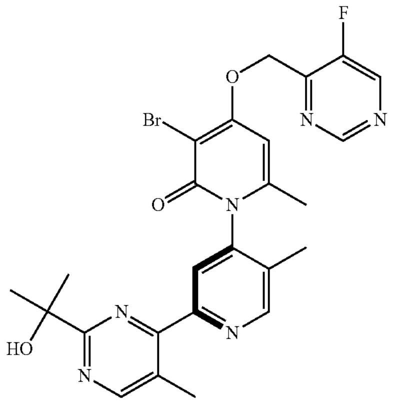 | (P)-3-bromo-4-((5-fluoropyrimidin-4-yl)methoxy)-2'-(2-(2-hydroxypropan-2-yl)-5-methylpyrimidin-4-yl)-5',6-dimethyl-2H-[1,4'-bipyridin]-2-one |

-continued

| No. | Structure | Compound Name |
|---|---|---|
| 71a | 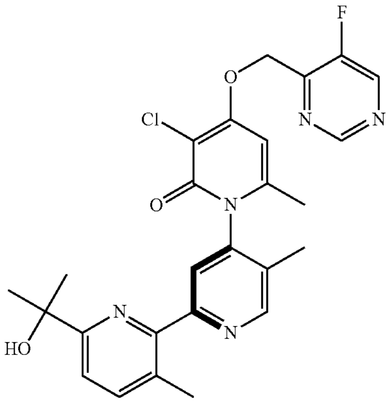 | (P)-3-chloro-4-((5-fluoropyrimidin-4-yl)methoxy)-6''-(2-hydroxypropan-2-yl)-3'',5',6-trimethyl-2H-[1,4':2',2''-terpyridin]-2-one |
| 72a | 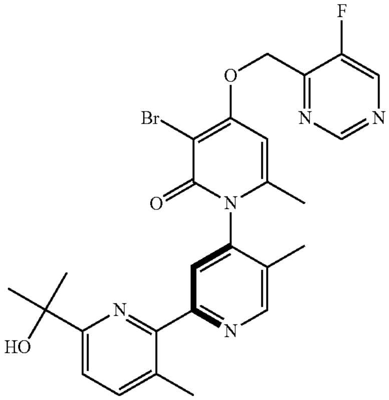 | (P)-3-bromo-4-((5-fluoropyrimidin-4-yl)methoxy)-6''-(2-hydroxypropan-2-yl)-3'',5',6-trimethyl-2H-[1,4':2',2''-terpyridin]-2-one |

In certain embodiments each of the compounds of Formula (P)-Ia, Formula (P)-IIa, Formula (P)-IIIa, Formula (P)-IVa, Formula (P)-Va, Formula (P)-VIa, and Formula (P)-VIIa, are substantially free of their corresponding M isomer.

In some embodiments, the chemical purity of any one of the compounds of Formula (P)-Ia, Formula (P)-IIa, Formula (P)-IIIa, Formula (P)-IVa, Formula (P)-Va, Formula (P)-VIa, or Formula (P)-VIIa, is about 95% or greater, is about 96% or greater, is about 97% or greater, is about 98% or greater, is about 98.5% or greater, is about 99% or greater, is about 99.5% or greater, is about 99.8% or greater, is about 99.9% or greater, is about 99.91% or greater, is about 99.92% or greater, is about 99.93% or greater, is about 99.94% or greater, is about 99.95% or greater, is about 99.96% or greater, is about 99.97% or greater, is about 99.98% or greater, or is about 99.99% or greater.

The present disclosure includes embodiments directed to a crystalline form of Compound 49a, or a pharmaceutically acceptable salt thereof, or a freebase thereof:

Compound 49a

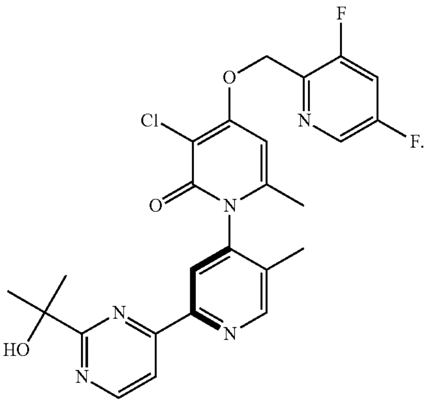

(P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one In some embodiments, Compound 49a is a freebase.

In some embodiments, Compound 49a is a pharmaceutically acceptable sale

In some embodiments, the pharmaceutically acceptable salt is a HCl salt.

In some embodiments, the crystalline form of Compound 49a is Form A.

In some embodiments, crystalline Form A of Compound 49a is anhydrous.

In some embodiments, crystalline Form A of Compound 49a is characterized by an XRPD pattern having a peak expressed in degrees 2θ (±0.2) at about 9.78. In some embodiments, Form A is characterized by an XRPD pattern having peaks expressed in degrees 2θ (±0.2) at about 9.78, and about 15.51. In some embodiments, crystalline Form A is characterized by an XRPD pattern having peaks expressed in degrees 2θ (±0.2) at about 9.78, about 15.51, about 19.6, and about 25.92. In some embodiments, crystalline Form A is characterized by an XRPD pattern having peaks expressed in degrees 2θ (±0.2) at about 9.78, about 15.34, about 15.51, about 19.6, about 20.57, about 21.01, about 25.92, about 29.05, and about 29.48. In some embodiments, crystalline Form A of Compound 49a is characterized by an XRPD pattern of FIG. 4.

Figure 5:
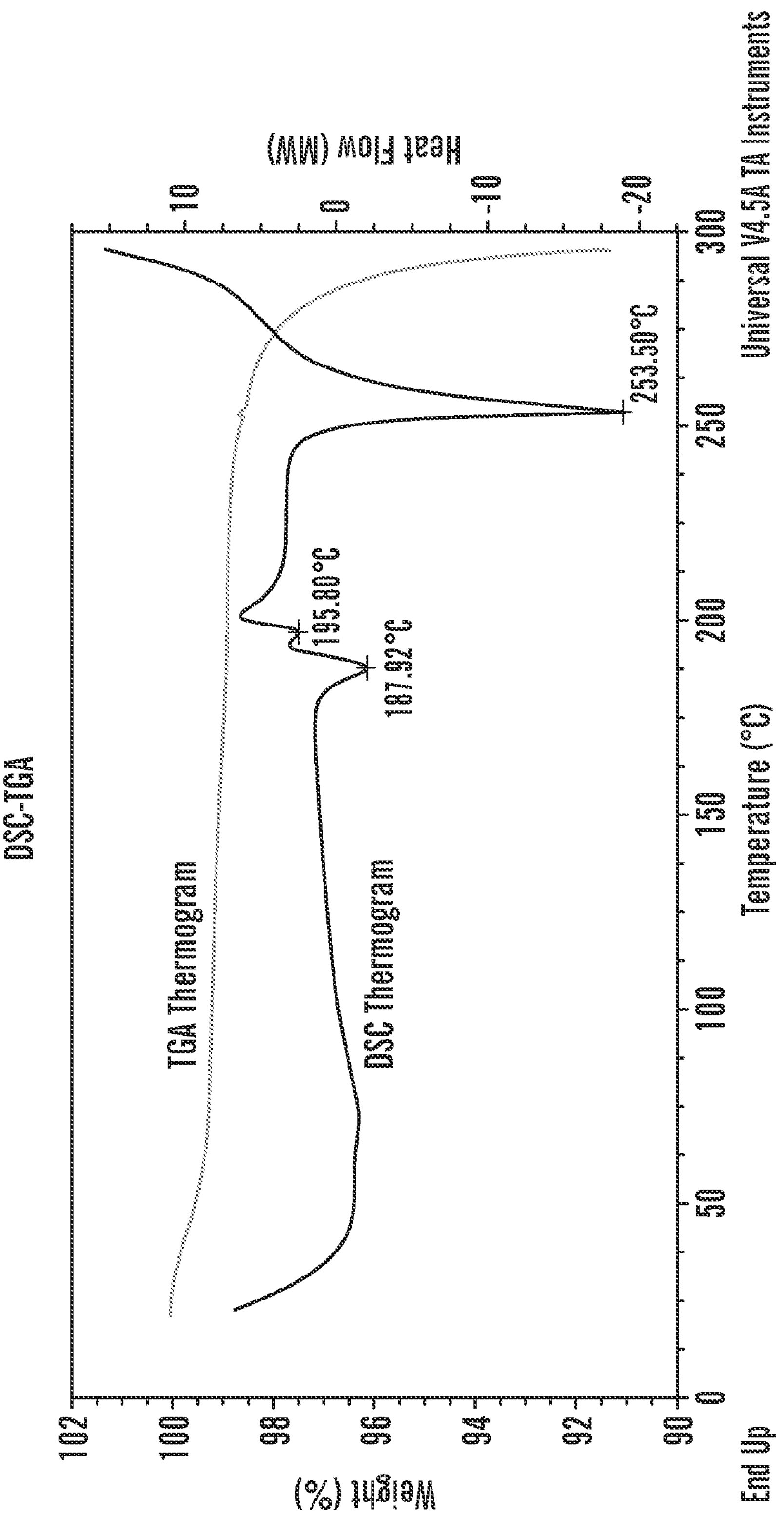

In one embodiment, provided herein is crystalline Form A of Compound 49a having a TGA thermograph corresponding substantially to the representative TGA thermogram as depicted in FIG. 5. In some embodiments, negligible weight loss is observed. Weight loss (0.7%) is observed between 25-256° C. by TGA for crystalline Form A of Compound 49a.

In one embodiment, provided herein is crystalline Form A of Compound 49a having a DSC thermogram corresponding substantially as depicted in FIG. 5. In certain embodiments, crystalline Form A of Compound 49a is characterized by a DSC plot comprising an initial endothermic melting event with an onset temperature of about 188° C., followed by an exothermic recrystallization event at about 196° C., with a final sharp endothermic melting event at about 254° C.

In some embodiments, the crystalline form of Compound 49a, or a pharmaceutically acceptable salt thereof, or a freebase thereof, contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of Compound 49a's corresponding M isomer, or a pharmaceutically acceptable salt thereof, or a freebase thereof. In some embodiments, the crystalline form of Compound 49a, or a pharmaceutically acceptable salt thereof, or a freebase thereof, contains not more than about 0.25 mol % of Compound 49a's corresponding M isomer, or a pharmaceutically acceptable salt thereof, or a freebase thereof. In some embodiments, the crystalline form of Compound 49a, or a pharmaceutically acceptable salt thereof, or a freebase thereof, is substantially free of Compound 49a's corresponding M isomer, or a pharmaceutically acceptable salt thereof, or a freebase thereof.

In some embodiments, Compound 49a has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, Compound 49a is substantially pure.

In some embodiments, crystalline Form A of Compound 49a contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, crystalline Form A of Compound 49a is substantially free of other solid forms.

Pharmaceutical Compositions

Some embodiments herein are directed to a pharmaceutical composition comprising a compound or a crystalline form of a compound of embodiments herein and a pharmaceutically acceptable excipient. In some embodiments each of the compositions comprise a compound selected from Formula (P)-Ia, Formula (P)-IIa, Formula (P)-IIIa, Formula (P)-IVa, Formula (P)-Va, Formula (P)-VIa, and Formula (P)-VIIa. In some embodiments, the pharmaceutical composition is substantially free of any corresponding M isomer.

The present disclosure includes embodiments directed to a pharmaceutical composition comprising a crystalline form of Compound 49a, or a pharmaceutically acceptable salt thereof, or a freebase thereof.

Compound 49a

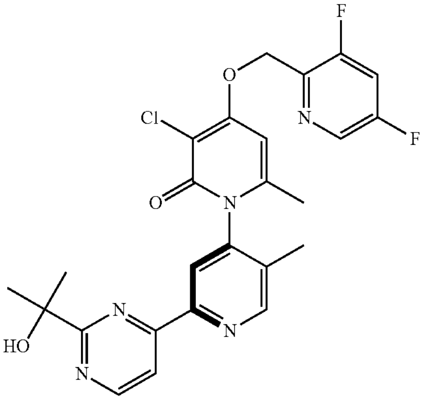

(P)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one and a pharmaceutically acceptable excipient.

The present disclosure also includes a pharmaceutical composition comprising Compound 49a, or a pharmaceutically acceptable salt thereof, or a freebase thereof, and Compound 49b, or a pharmaceutically acceptable salt thereof, or a freebase thereof:

Compound 49a

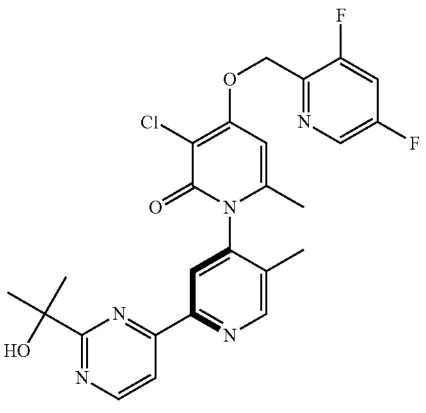

(P)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one Compound 49b

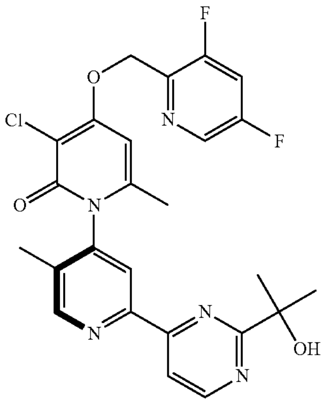

(M)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one wherein the molar ratio of Compound 49a, a pharmaceutically acceptable salt thereof, or a freebase thereof, to Compound 49b, a pharmaceutically acceptable salt thereof, or a freebase thereof, is about 4:1;

and a pharmaceutically acceptable excipient.

In some embodiments the pharmaceutical compositions disclosed herein comprise a pharmaceutically acceptable salt of Compound 49a, wherein the pharmaceutically acceptable salt is a HCl salt.

In some embodiments the pharmaceutical compositions disclosed herein, comprise Compound 49a as a freebase. In some embodiments the pharmaceutical compositions disclosed herein comprise Compound 49b as a freebase.

In some embodiments the pharmaceutical compositions disclosed herein comprise the crystalline form of Compound 49a. In some embodiments, the crystalline form of Compound 49a is Form A.

In some embodiments of pharmaceutical compositions disclosed herein comprises a crystalline Form A of Compound 49a is anhydrous.

In some embodiments the pharmaceutical compositions disclosed herein comprise crystalline Form A of Compound 49a that is characterized by an XRPD pattern having a peak expressed in degrees 2θ (+0.2) at about 9.78. In some embodiments of the pharmaceutical compositions disclosed herein, Form A is characterized by an XRPD pattern having peaks expressed in degrees 2θ (+0.2) at about 9.78, and about 15.51. In some embodiments of the pharmaceutical compositions disclosed herein, crystalline Form A is characterized by an XRPD pattern having peaks expressed in degrees 2θ (+0.2) at about 9.78, about 15.51, about 19.6, and about 25.92. In some embodiments of the pharmaceutical compositions disclosed herein, crystalline Form A is characterized by an XRPD pattern having peaks expressed in degrees 2θ (+0.2) at about 9.78, about 15.34, about 15.51, about 19.6, about 20.57, about 21.01, about 25.92, about 29.05, and about 29.48.

Figure 4:
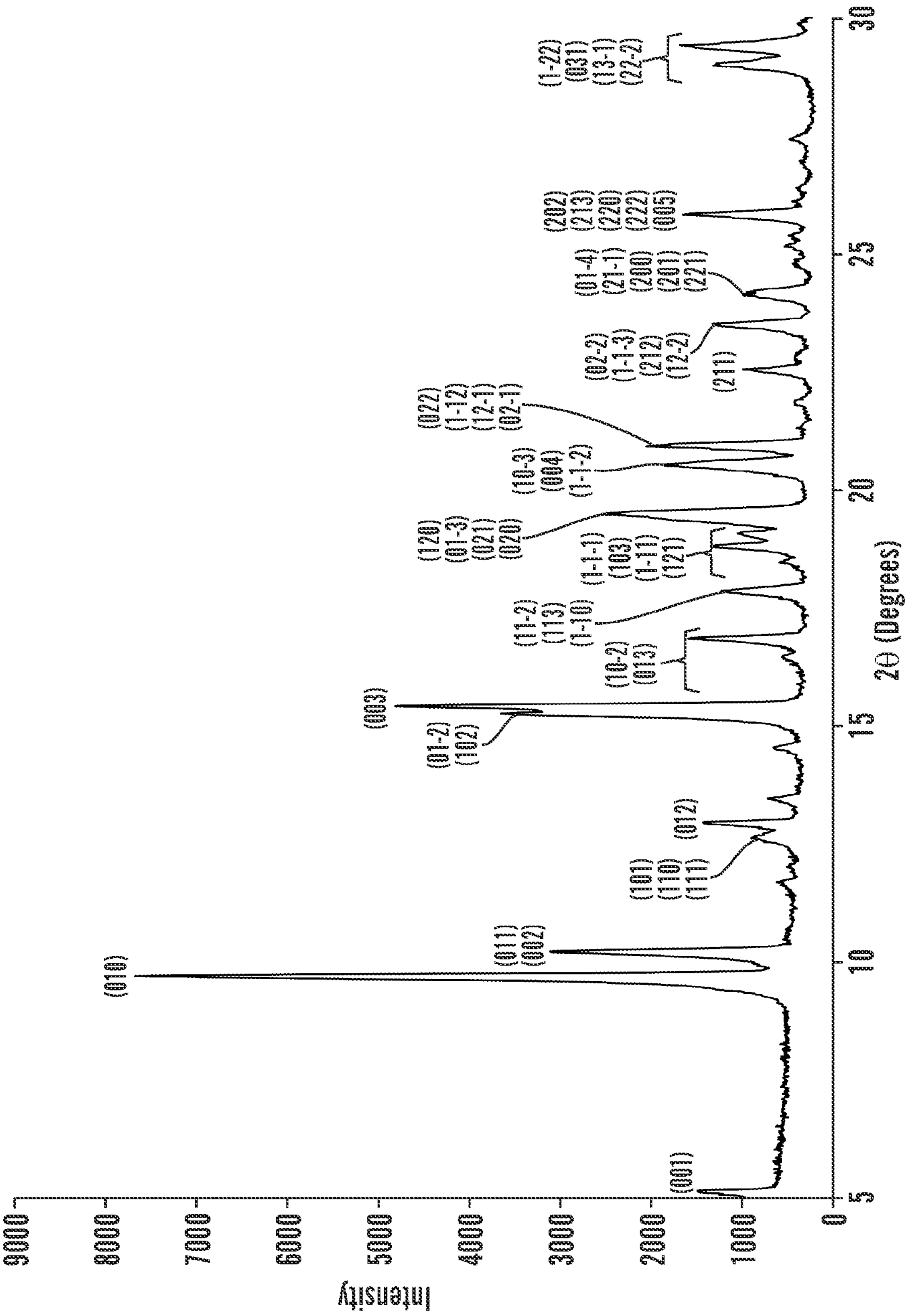
FIG. 4 shows an X-ray powder diffractogram plot of crystalline Form A of Compound 49a showing the location of significant Bragg reflections, their 2-theta positions and intensity values.

In some embodiments the pharmaceutical compositions disclosed herein comprise a crystalline Form A of Compound 49a that is characterized by an XRPD pattern of FIG. 4.

In one embodiment, crystalline Form A of Compound 49a of the pharmaceutical composition has a TGA thermograph corresponding substantially to the representative TGA thermogram as depicted in FIG. 5. In some embodiments of the pharmaceutical compositions disclosed herein, negligible weight loss is observed weight loss (0.7%) is observed between 25-256° C. by TGA for crystalline Form A of Compound 49a.

In one embodiment, crystalline Form A of Compound 49a of the pharmaceutical composition has a DSC thermogram corresponding substantially as depicted in FIG. 5. In certain embodiments, crystalline Form A of Compound 49a is characterized by a DSC plot comprising an initial endothermic melting event with an onset temperature of about 188° C., followed by an exothermic recrystallization event at about 196° C., with a final sharp endothermic melting event at about 254° C.

In some embodiments the pharmaceutical compositions disclosed herein comprise the crystalline form of Compound 49a, or a pharmaceutically acceptable salt thereof, or a freebase thereof, and contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of Compound 49a's corresponding M isomer, or a pharmaceutically acceptable salt thereof, or a freebase thereof. In some embodiments the pharmaceutical compositions disclosed herein comprise the crystalline form of Compound 49a, or a pharmaceutically acceptable salt thereof, or a freebase thereof, and contains not more than about 0.25 mol % of Compound 49a's corresponding M isomer, or a pharmaceutically acceptable salt thereof, or a freebase thereof. In some embodiments of pharmaceutical compositions disclosed herein comprise the crystalline form of Compound 49a, or a pharmaceutically acceptable salt thereof, or a freebase thereof, and is substantially free of Compound 49a's corresponding M isomer, or a pharmaceutically acceptable salt thereof, or a freebase thereof.

In some embodiments, the pharmaceutical compositions disclosed herein comprise Compound 49a having a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, the pharmaceutical compositions disclosed herein comprise Compound 49a in a substantially pure form.

In some embodiments, the pharmaceutical compositions disclosed herein comprise crystalline Form A of Compound 49a that contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, the pharmaceutical compositions disclosed herein comprise crystalline Form A of Compound 49a substantially free of other solid forms.

In some embodiments, the pharmaceutical compositions disclosed herein comprise the crystalline form of Compound 49a, or a pharmaceutically acceptable salt thereof, or a freebase thereof, is in a therapeutically effective amount. In some embodiments, the pharmaceutical compositions disclosed herein comprise Compound 49a, or a pharmaceutically acceptable salt thereof, or a freebase thereof, and Compound 49b, or a pharmaceutically acceptable salt thereof, or a freebase thereof, combined in a therapeutically effective amount.

In some embodiments of the pharmaceutical compositions disclosed herein, the therapeutically effective amount is about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 5 mg to about 300 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 240 mg, about 200 mg, about 175 mg, about 160 mg, about 150 mg, about 125 mg, about 120 mg, about 110 mg, about 100 mg, about 90 mg, about 80 mg, about 70 mg, about 60 mg, about 50 mg, about 40 mg, about 30 mg, about 20 mg, about 10 mg, or any value between the ranges disclosed above. In some embodiments of the pharmaceutical compositions disclosed herein, the therapeutically effective amount is about 5 mg to about 300 mg. In some embodiments of the pharmaceutical compositions disclosed herein, the therapeutically effective amount is about 240 mg. In some embodiments of the pharmaceutical compositions disclosed herein, the therapeutically effective amount is about 200 mg. In some embodiments of the pharmaceutical compositions disclosed herein, the therapeutically effective amount is about 160 mg. In some embodiments of the pharmaceutical compositions disclosed herein, the therapeutically effective amount is about 120 mg. In some embodiments of the pharmaceutical compositions disclosed herein, the therapeutically effective amount is about 100 mg. In some embodiments of the pharmaceutical compositions disclosed herein, the therapeutically effective amount is about 80 mg. In some embodiments of the pharmaceutical compositions disclosed herein, the therapeutically effective amount is about 60 mg. In some embodiments of the pharmaceutical compositions disclosed herein, the therapeutically effective amount is about 50 mg. In some embodiments of the pharmaceutical compositions disclosed herein, the therapeutically effective amount is about 40 mg. In some embodiments of the pharmaceutical compositions disclosed herein, the therapeutically effective amount is about 10 mg.

In some embodiments of the pharmaceutical compositions disclosed herein, the molar ratio of Compound 49a, or a pharmaceutically acceptable salt thereof, or a freebase thereof, to Compound 49b, or a pharmaceutically acceptable salt thereof, or a freebase thereof, is about 4.3:1, about 4.6:1, about 4.9:1, about 5.25:1, about 5.7:1, about 6.1:1, about 6.7:1, about 7.3:1, about 8.1:1, about 9:1, about 10:1, about 11.5:1, about 13.3:1, about 15.7:1, about 19:1, about 24:1, about 32.3:1, about 49:1, about 91:1, about 110.1:1, about 124:1, about 141.9:1, about 165.7:1, about 199:1, about 249:1, about 332.3:1, about 399:1, about 499:1, and about 999:1.

In some embodiments, the pharmaceutical compositions disclosed herein is an oral pharmaceutical composition.

In some embodiment, the oral pharmaceutical composition is in the form of a tablet.

While it may be possible for the compounds described herein to be administered as the raw chemical, it is also possible to present them as a pharmaceutical composition. Accordingly, provided herein are pharmaceutical compositions which comprise one or more of certain compounds disclosed herein together with one or more pharmaceutically acceptable excipients thereof and optionally one or more other therapeutic ingredients. The excipient(s) must be "acceptable" in the sense of being compatible with the other ingredients of the formulation and not deleterious to the recipient thereof. Proper formulation of the pharmaceutical composition is dependent upon the route of administration chosen. Any of the well-known techniques and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In some embodiments, the pharmaceutical compositions for use in accordance with embodiments herein can be formulated in conventional manner using one or more physiologically acceptable excipients.

The compositions include those suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration although the most suitable route may depend upon for example the condition and disorder of the recipient.

The composition could include those suitable for administration by depot injections or by implants. The composition could include those suitable for administration by inhalation, such as, for example, a gas, vapor, or powder. The composition could include those suitable for administration, e.g., as an aerosol via a nebulizer, humidifier, inhaler and vaporizer or the like. The compositions may conveniently be presented in unit dosage form and may be prepared by any of the methods well known in the art of pharmacy. Typically, these methods include the step of bringing into association a compound disclosed herein ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

Compositions of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Compositions for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the composition isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the pharmaceutical compositions described previously, the compounds may also be formulated as a depot preparation. Such long acting compositions may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the pharmaceutical compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose. In contrast, systemic administration refers to oral, intravenous, intraperitoneal and intramuscular administration.

In some embodiments, pharmaceutical compositions suitable for topical administration include liquid or semi-liquid preparations suitable for penetration through the skin to the site of inflammation such as a solution, powder, fluid emulsion, fluid suspension, semi-solid, ointment, paste, cream, gel, jelly, foam, liniment, lotion, and drops suitable for administration to the eye, ear or nose. The active ingredient for topical administration may comprise, for example, from 0.001% to 10% w/w (by weight) of the composition. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the composition.

Gels for topical or transdermal administration may comprise, generally, a mixture of volatile solvents, nonvolatile solvents, and water. In certain embodiments, the volatile solvent component of the buffered solvent system may include lower ($C_1$-$C_6$) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid pharmaceutical compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The pharmaceutical composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Pharmaceutical compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage pharmaceutical compositions are those containing a therapeutically effective amount, as herein below recited, or an appropriate fraction thereof, of the active ingredient.

It should be understood that in addition to the ingredients particularly mentioned above, the pharmaceutical compositions described above may include other agents conventional in the art having regard to the type of pharmaceutical composition in question, for example those suitable for oral administration may include flavoring agents.

Compounds may be administered at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be oral, parenteral (including subcutaneous, intradermal, intramuscular, intravenous, intraarticular, and intramedullary), pulmonary (e.g., by inhalation or insufflation of powders or aerosols, including by nebulizer; intratracheal or intranasal), intraperitoneal, intrathecal, intradural, transmucosal, transdermal, rectal, topical (including dermal, buccal, sublingual and intraocular), or intravaginal administration. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the compounds can be contained in such pharmaceutical compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, Modem Pharmaceutics, 5th Edition, Banker & Rhodes, CRC Press (2009); and Goodman & Gilman's The Pharmaceutical Basis of Therapeutics, 13th Edition, McGraw Hill, New York (2018) can be consulted.

In some embodiments, a method of treating a p38 MAP Kinase mediated disease comprises administering a pharmaceutical composition of embodiments disclosed herein. In some embodiments, the compound is in a therapeutically effective amount. In some embodiments, the therapeutically effective amount is an amount disclosed herein.

In some embodiments, a method of making a pharmaceutical composition comprises, mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The pharmaceutical compositions can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The pharmaceutical compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the pharmaceutical composition may comprise about 0.01% to about 50% of one or more compounds disclosed herein. In some embodiments, the one or more compounds is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration. In some embodiments, the pharmaceutical composition is suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration.

In some embodiments, the therapeutically effective amount can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 μg/kg to about 1 g/kg of body weight per day. In some embodiments, the dose range is from about 0.01 mg/kg to about 100 mg/kg of body weight per day. In some embodiments, the dose range is from about 0.1 mg/kg to about 10 mg/kg of body weight per day. The dosage is likely to depend on such variables as the type and extent of progression of the disease or disorder, the overall health status of the particular patient, the relative biological efficacy of the compound selected, pharmaceutical composition of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the pharmaceutical composition so that the pharmaceutical composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the pharmaceutical compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the composition in an appropriate manner.

In some embodiments, the pharmaceutical compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

The compositions can further include one or more additional pharmaceutical agents such as a chemotherapeutic, steroid, anti-inflammatory compound, or immunosuppressant as described herein.

Methods of Use

The present invention relates to a method of modulating a p38 MAP Kinase-mediated function in a subject comprising the administration of a therapeutically effective amount of a compound as disclosed herein. In certain embodiments each of the compounds disclosed herein of Formula (P)-Ia, Formula (P)-IIa, Formula (P)-IIIa, Formula (P)-IVa, Formula (P)-Va, Formula (P)-VIa, and Formula (P)-VIIa, or a pharmaceutical composition comprising the same, is substantially free of their corresponding M isomer.

In some embodiments, the methods of modulating a p38 MAP Kinase mediated function comprising administering a therapeutically effective amount of the crystalline form of Compound 49a, or a pharmaceutically acceptable salt thereof, or a freebase thereof, or a pharmaceutical composition comprising the same. In some embodiments, Compound 49a administered in accordance with these methods is substantially free of its corresponding M isomer. In some embodiments, the crystalline form of Compound 49a is Form A.

The present invention also relates to a method of inhibiting at least one p38 MAP Kinase function comprising the step of contacting p38 MAP Kinase with a compound as described herein. The cell phenotype, cell proliferation, activity of p38 MAP Kinase, change in biochemical output produced by active p38 MAP Kinase, expression of p38 MAP Kinase, or binding of p38 MAP Kinase with a natural binding partner may be monitored to determine the level of p38 MAK Kinase modulation achieved with the compounds described herein. Such methods may be modes of treatment of disease, biological assays, cellular assays, biochemical assays, or the like.

Also provided herein is a method of treating a p38 MAP Kinase-mediated disease comprising administering to a patient in need thereof a therapeutically effective amount of a compound as disclosed herein or a combination thereof. In certain embodiments, the therapeutically effective amount of a compound as disclosed herein or a combination thereof, may be in the form of a pharmaceutical composition. In embodiments, the pharmaceutical composition may include a pharmaceutically acceptable excipient.

In embodiments, diseases or disorders associated with a p38 MAP Kinase that are treated by compounds of the present invention include autoimmune disorders, chronic inflammatory disorders, acute inflammatory disorders, autoinflammatory disorders, fibrotic disorders, metabolic disorders, neoplasias, or cardiovascular or cerebrovascular disorders. Thus, in some embodiments, the present invention provides a method for treating a p38 MAP Kinase mediated disease or disorder in a patient in need thereof, wherein said method comprises administering to said patient a therapeutically effective amount of a provided compound, or composition thereof. Such p38 MAP Kinase-mediated diseases or disorders include, but are not limited to those described herein.

In any embodiment, the pharmaceutical compositions disclosed herein are suitable for treating chronic or acute inflammatory or autoimmune gastrointestinal disorders, inflammatory or autoimmune skin disorders, neuroinflammatory disorders, inflammatory heart disease, inflammatory lung diseases, inflammatory myopathies, inflammatory bone disorders or diseases, periodic fever syndromes, as well as pain or pruritus associated with any aforementioned disease.

In any embodiment, the pharmaceutical compositions disclosed herein may also be used to treat scarring/fibrotic diseases or disorders and various types of cancers and hyper proliferative disorders.

In any embodiment, the pharmaceutical compositions disclosed herein are suitable for treating inflammatory arthritis, such as rheumatoid arthritis (RA), spondyloarthritis such as ankylosing spondylitis, psoriatic arthritis, reactive arthritis and Reiter's syndrome, juvenile rheumatoid arthritis (JIA), systemic-onset juvenile rheumatoid arthritis, idiopathic arthritis (JIA) (including systemic (SJIA)), and gout; cryopyrin-associated autoinflammatory syndromes (CAPS), including Muckle-Wells syndrome (MWS), neonatal-onset multisystem inflammatory disease (NOMID), and familial cold autoinflammatory syndrome (FCAS); chronic obstructive pulmonary diseases (COPD), including emphysema, chronic bronchitis, and asthma (allergic and non-allergic), hidradenitis suppurativa (HS); psoriasis, such as plaque psoriasis; colitis from an inflammatory bowel disease (IBD) like Crohn's disease or ulcerative colitis and inflammatory bowel disease-associated arthritis; pericarditis, including acute pericarditis, recurrent pericarditis, and chronic pericarditis; pulmonary inflammation or fibrosis, including idiopathic pulmonary fibrosis; metastatic breast cancer, and pancreatic cancer.

In any embodiment, the pharmaceutical compositions disclosed herein are suitable for treating Familial Mediterranean Fever (FMF); tumor necrosis factor receptor-associated periodic syndrome (TRAPS); adult-onset Still's disease; pyoderma gangrenosum; bone-resorption disorders (such as those associated with cancer (e.g., breast cancer)); metastatic melanoma; Castleman disease; and chronic atypical neutrophilic dermatosis with lipodystrophy (CANDLE).

In any embodiment, the condition that is treated in accordance with the methods described here is pruritus, which may be associated with any other condition, for example, pruritus associated with hidradenitis suppurativa, pruritus associated with inflammation, pruritus associated with rheumatoid arthritis, pruritus associated with psoriasis, and pruritus associated with TH17-associated inflammation.

In any embodiment, the pharmaceutical compositions disclosed herein are suitable for treating Lyme disease; cytokine release syndrome (CRS); adult respiratory distress syndrome (ARDS); chronic or acute bronchitis; epidermolysis bullosa (EB); bullous pemphigoid; juvenile dermatomyositis; inflammatory vitiligo (including marginal); pemphigus vulgaris; enterocolitis; polymyositis; myositis, bone cancer; lung cancer; inflammatory bone disorders such as chronic recurrent multi osteomyelitis (CRMO), Synovitis, acne, pustulosis, hyperostosis, and osteitis (SAPHO) syndrome, Majeed syndrome, deficiency of interleukin-1 receptor antagonist (DIRA) and cherubism; bone resorption (such as is associated with an autoimmune disease); neuroinflammatory diseases such as Alzheimer's disease (AD), Parkinson's disease (PD), multiple sclerosis (MS), acute disseminated encephalomyelitis (ADEM), acute optic neuritis (AON), transverse myelitis, and neuromyelitis optical (NMO); Behcet's disease; endotoxic shock (e.g., toxic shock syndrome (TSS) and other systemic gram-negative bacterial infections); enthesitis; polyarteritis nodosa (PAN); chronic pain; polymyalgia rheumatica; chronic allograft rejection; Sjogren's syndrome; and Schnitzler's syndrome (SchS).

In any embodiment, said p38 MAP Kinase-mediated disease or disorder is chosen from a skin disorder, pruritus, a hair loss disorder, a cancer, a neoplasm, Alzheimer's disease, an inflammatory condition, connective tissue diseases and an autoimmune condition.

In any embodiment, said p38 MAP Kinase-mediated disease or disorder is a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, acute and chronic leukemias, lymphomas, cutaneous lymphomas including mycosis fungoides, other myeloid malignancies, and myelodysplastic syndrome In some embodiments the methods described herein are used to treat patients with disorders arising from dysregulated cytokine, enzymes and/or inflammatory mediator production, stability, secretion, posttranslational processing. In some embodiments, the methods described herein are used to treat patients having cytokine release syndrome, which is a systemic inflammatory response triggered by a variety of factors including infections (e.g., viral infection) and certain drugs (CAR T− cell therapy). Examples of cytokines that may be dysregulated in the aforementioned disorders include interleukins 1, 2, 6, 8, 10, 12, 17, 22 and 23 along with tumor necrosis factor alpha and interferons alpha, beta and gamma. Examples of inflammatory mediators that may be dysregulated include nitric oxide, prostaglandins and leukotrienes. Examples of enzymes include cyclo-oxygenase, nitric oxide synthase and matrixmetalloprotease.

Also provided herein is a compound as disclosed herein for use as a medicament.

Also provided herein is a compound as disclosed herein for use as a medicament for the treatment of a p38 MAP Kinase-mediated disease.

Also provided is the use of a compound as disclosed herein as a medicament.

Also provided is the use of a compound as disclosed herein as a medicament for the treatment of a p38 MAP Kinase-mediated disease.

Also provided is a compound as disclosed herein for use in the manufacture of a medicament for the treatment of a p38 MAP Kinase-mediated disease.

Also provided is the use of a compound as disclosed herein for the treatment of a p38 MAP Kinase-mediated disease.

Also provided herein is a method of inhibiting p38 MAP Kinase comprising contacting p38 MAP Kinase with a compound as disclosed herein.

The compounds and compositions disclosed herein can be administered in various modes, e.g. oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration. The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. Also, the route of administration may vary depending on the condition and its severity.

Besides being useful for human treatment, certain compounds and compositions disclosed herein may also be useful for veterinary treatment of companion animals, exotic animals and farm animals, including mammals, rodents, and the like. More preferred animals include horses, dogs, and cats.

Combination Therapy

The compounds and pharmaceutical compositions of the present disclosure may be used to prevent or treat a p38 MAP Kinase-mediated disease by the sequential or co-administration of another pharmaceutical agent.

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In certain instances, it may be appropriate to administer at least one of the compounds described herein in combination with another pharmaceutical agent. By way of example only, if one of the side effects experienced by a patient upon receiving one of the compounds herein is hypertension, then it may be appropriate to administer an anti-hypertensive agent in combination with the initial pharmaceutical agent. Or, by way of example only, the therapeutic effectiveness of one of the compounds described herein may be enhanced by administration of an adjuvant (i.e., by itself the adjuvant may only have minimal therapeutic benefit, but in combination with another pharmaceutical agent, the overall therapeutic benefit to the patient is enhanced). Or, by way of example only, the benefit of experienced by a patient may be increased by administering one of the compounds described herein with another pharmaceutical agent (which also includes a therapeutic regimen) that also has therapeutic benefit. By way of example only, in a treatment for diabetes involving administration of one of the compounds described herein, increased therapeutic benefit may result by also providing the patient with another pharmaceutical agent for diabetes. In any case, regardless of the disease, disorder or condition being treated, the overall benefit experienced by the patient may simply be additive of the two pharmaceutical agents or the patient may experience a synergistic benefit.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneous, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

Thus, in another aspect, certain embodiments provide methods for treating p38 MAP Kinase-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of p38 MAP Kinase-mediated disorders.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

p38 MAP Kinase inhibitor compositions described herein are also optionally used in combination with other therapeutic reagents that are selected for their therapeutic value for the condition to be treated In general, the pharmaceutical compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified. In certain instances, it is appropriate to administer a p38 MAP Kinase inhibitor composition as described herein in combination with another therapeutic agent. By way of example only, if one of the side effects experienced by a patient upon receiving a p38 MAP Kinase inhibitor composition as described herein is rash, then it is appropriate to administer an anti-histamine agent in combination with the initial therapeutic agent. Or, by way of example only, the therapeutic effectiveness of a p38 MAP Kinase inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a p38 MAP Kinase inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses.

If not simultaneous, the timing between the multiple doses optionally varies from more than zero weeks to less than twelve weeks.

In addition, the combination methods and compositions are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a p38 MAP Kinase inhibitor is optionally used in combination with procedures that provide additional or synergistic benefit to the patient. A p38 MAP Kinase inhibitor and the additional therapy(ies) are optionally administered before, during or after the occurrence of a disease or condition, and the timing of administering the composition containing a p38 MAP Kinase inhibitor varies in some embodiments. Thus, for example, a p38 MAP Kinase inhibitor is used as a prophylactic and is administered continuously to subjects with a propensity to develop conditions or diseases in order to prevent the occurrence of the disease or condition. A p38 MAP Kinase inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A p38 MAP Kinase inhibitor may be used in combination with drugs from the following classes: NSAIDs, immunosuppressive drugs, immunomodulatory drugs, cytostatic drugs, anti-proliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a p38 MAP Kinase inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.)

Where a subject is suffering from or at risk of suffering from an inflammatory condition, a p38 MAP Kinase inhibitor composition described herein is optionally used together with one or more agents or methods for treating an inflammatory condition in any combination.

Specific, non-limiting examples of possible combination therapies include use of compounds of embodiments herein with: chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (ANSAID™) ketoprofen, oxaprozin (DAYPRO™), diclofenac sodium (VOLTAREN™), diclofenac potassium (CATAFLAM™), etodolac (LODINE™), indomethacin (INDOCIN™) ketorolac (TORADOL™), sulindac (CLINORIL™), tolmetin (TOLECTIN™) meclofenamate (MECLOMEN™), mefenamic acid (PONSTEL™), nabumetone (RELAFEN™) and piroxicam (FELDENE™); (3) immunosuppressants, including but not limited to methotrexate (RHEUMATREX™), leflunomide (ARAVA™), azathioprine (IMURAN™), cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™); (6) interleukin-1 receptor antagonists, including but not limited to anakinra (KINERET™); (7) interleukin-6 inhibitors, including but not limited to tocilizumab (ACTEMRA™); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN™), carboplatin (PARAPLATIN™) oxaliplatin (ELOXATIN™), streptozocin (ZANOSAR™), busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™), gemcitabine (GEMZAR™), fluorouracil (CARAC™), leucovorin (FUSILEV™) and methotrexate (RHEUMATREX™); (3) plant alkaloids and terpenoids, including but not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™)

and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™), lapatininb (TYKERB™) and axitinib (INLYTA™); and (8) immune checkpoint inhibitors, including but not limited to atezolizumab (TECENTRIQ™), avelumab (BAVENCIO™), durvalumab (IMFINZI™) ipilimumab (YERVOY™), pembrolizumab (KEYTRUDA™), nivolumab (OPDIVO™) tremelimumab; and combinations thereof, e.g., FOLFIRINOX which is a combination of folinic acid (also called leucovorin), fluorouracil, irinotecan, and oxaliplatin.

In some embodiments, the compounds disclosed in embodiments herein can also be co-administered (concurrently or sequentially) with a variety of other pharmaceutical agents or treatments, for example, pharmaceutical agents or treatments that are administered systemically, such as orally or parenterally. Examples of such systemic treatments include topical or systemic corticosteroids (such as prednisone), antibiotics (such as erythromycin, tetracycline, and dicloxacillin), antifungal agents (such as ketoconazole and fluconazole sold under the tradename Diflucan™), antiviral agents (such as valacyclovir sold under the tradename Valtrex™, acyclovir, and famciclovir sold under the tradename Famvir™) corticosteroids, immunosuppressants (such as cyclophosphamide sold under the tradename Cytoxan™, azathioprine, methotrexate, mycophenolate), biologics (such as rituximab sold under the tradename Rituxan™, etanercept sold under the tradename Enbrel™, adalimumab sold under the tradename Humira™, infliximab sold under the tradename Remicade™, ustenkinumab sold under the tradename Stelara™, and alefacept sold under the tradename Amevive™), and/or thyroid hormone replacement.

In some embodiments, other therapies that can be used in combination with the compounds disclosed herein include, for example, mercaptopurine, topical or systemic corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, antilymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the compounds of embodiments herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the compounds of embodiments herein or the additional pharmaceutical agents, or both. Azathioprine is currently available from Salix Pharmaceuticals, Inc. under the brand name Azasan™; mercaptopurine is currently available from Gate Pharmaceuticals, Inc. under the brand name Purinethol™; prednisone and prednisolone are currently available from Roxane Laboratories, Inc.; methyl prednisolone is currently available from Pfizer; sirolimus (rapamycin) is currently available from Wyeth-Ayerst under the brand name Rapamune™; tacrolimus is currently available from Fujisawa under the brand name Prograf™; cyclosporine is current available from Novartis under the brand name Sandimmune™ and Abbott under the brand name Gengraf™; IMPDH inhibitors such as mycophenolate mofetil and mycophenolic acid are currently available from Roche under the brand name Cellcept™ and Novartis under the brand name Myfortic™; azathioprine is currently available from Glaxo Smith Kline under the brand name Imuran™; and antibodies are currently available from Ortho Biotech under the brand name Orthoclone™, Novartis under the brand name Simulect™ (basiliximab) and Roche under the brand name Zenapax™ (daclizumab).

In some embodiments, the compounds of embodiments herein are administered in conjunction, concomitantly or adjunctively, with the pharmaceutical agents or therapies above and/or with a pharmaceutical agent or therapy for another disease. For example, the compounds of embodiments herein may be combined with thyroid hormone replacement therapy or with anti-inflammatory or immunomodulatory therapies.

In some embodiments, the combination therapies in embodiments herein may be administered in sub-therapeutic amounts of either the compounds of embodiments herein or the additional pharmaceutical agents, or both.

For use in cancer and neoplastic diseases a p38 MAP Kinase inhibitor is optimally used together with one or more of the following classes of drugs: wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteosome inhibitor, chemotherapy agent, or glucose reduction agent.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneous, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

In certain embodiments, the additional pharmaceutical agent is selected from taxanes, inhibitors of bcr-abl, inhibitors of EGFR, DNA damaging agents, antimetabolites, paclitaxel, imatinib, dasatinib, nilotinib, erlotinib, gefitinib, cisplatin, oxaliplatin, carboplatin, anthracyclines, AraC, 5-FU, camptothecin, doxorubicin, idarubicin, paclitaxel, docetaxel, vincristine, a MEK inhibitor, U0126, a KSP inhibitor, vorinostat, pembrolizumab, nivolumab, atezolizumab, avelumab, tremelimumab, and durvalumab.

In some embodiments, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, and an agent for treating immunodeficiency disorders.

In some embodiments, one or more compounds of the embodiments herein can be used in combination with one or more other therapeutics used in the treatment of p38 MAP Kinase-mediated disorders, and may improve the treatment response as compared to the response to the other therapeutics alone, without exacerbation of its toxic effects. In some embodiments, compounds of embodiments herein can be used in combination with one or more JAK 1 and/or JAK3 inhibitors and/or JAK2 inhibitors and/or TYK2 inhibitors for the treatment of p38 MAP Kinase-mediated disorders. Additive or synergistic effects are desirable outcomes of such combinations. The additional agents can be combined with the present compounds in a single or continuous dosage form, or the agents can be administered simultaneously or sequentially as separate dosage forms. In some embodiments, one or more additional agents can be administered to a patient in combination with at least one p38 MAP Kinase inhibitor/antagonist described herein where the additional agents are administered intermittently as opposed to continuously.

General Synthetic Methods for Preparing Compounds

Some embodiments herein are directed to methods for maximizing the synthetic yield of a compound having the structure of Formula (P)-Ia (as described herein) by interconverting a compound having the structure of Formula (M)-Ib:

(P)-Ia

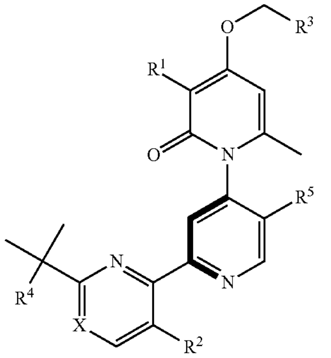

(M)-Ib

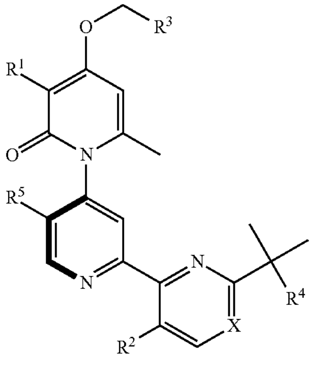

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^3$ is selected from the group consisting of

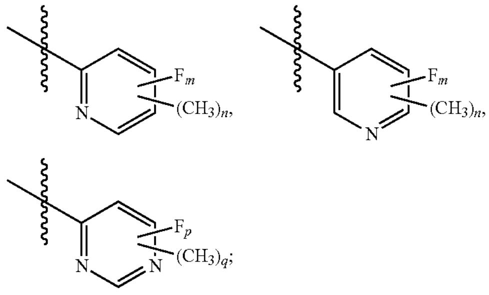

$R^4$ is selected from the group consisting of H, methyl, OH, and —$OCH_3$;

$R^5$ is H or $C_1$-$C_3$ alkyl;

m is 1 or 2;

n is 0 or 1;

p is 1;

q is 0 or 1; or a derivative thereof, and wherein the method comprises heating a solution comprising a compound of Formula (M)-Ib to a temperature at which the compound interconverts.

In another embodiment, there is provided methods for maximizing the synthetic yield of a compound having the structure of Formula (P)-Ia (as described herein) by interconverting a compound having the structure of Formula (M)-Ib, wherein the solution comprises a solvent which affords an interconversion temperature of 110° C.-170° C.

In another embodiment, there is provided methods for maximizing the synthetic yield of a compound having the structure of Formula (P)-IIa (as described herein) by interconverting a compound having the structure of Formula (M)-IIb:

(P)-IIa

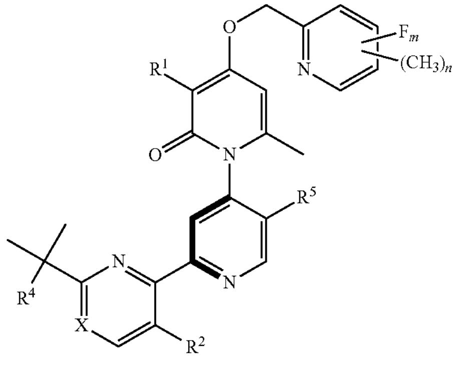

-continued (M)-IIb

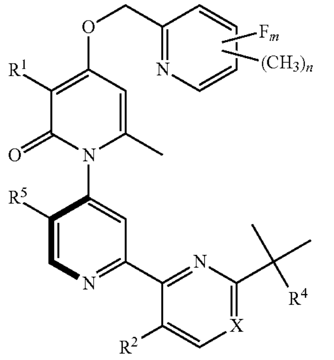

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^4$ is selected from the group consisting of H, methyl, OH, and —$OCH_3$;

$R^5$ is H or $C_1$-$C_3$ alkyl;

m is 1 or 2;

n is 0 or 1; or a derivative thereof; and wherein the method comprises heating a solution comprising the compound of Formula (M)-Ib to an interconversion temperature to form a mixture of atropisomers of the compound of Formula (M)-Ib and the compound of Formula (P)-Ia.

In another embodiment the solution is heated to the interconversion temperature for 1 hour, 2 hours, 3 hours, 4 hours, 5 hours, 6 hours, 7 hours, 8 hours, 9 hours, 10 hours, or a range between any two of these values.

In another embodiment the solution is heated to the interconversion temperature for 3 hours.

In another embodiment, the interconversion temperature is 110° C.-210° C.

In another embodiment, the interconversion temperature is 110° C.-170° C.

In another embodiment, the interconversion temperature is 110° C.-150° C.

In another embodiment, the interconversion temperature is 110° C.-140° C.

In another embodiment, the interconversion temperature is 110° C.-125° C.

In another embodiment, the interconversion temperature is 145° C.-150° C.

In another embodiment, the solvent is an alcohol.

In another embodiment, the solvent is N-methylpyrrolidone or dimethylacetamide or combinations thereof.

In another embodiment, the solvent has a boiling point of 110° C.-150° C.

In another embodiment, the solvent is ethylene glycol.

In another embodiment, the solvent is n-butanol.

In another embodiment, there is provided methods for maximizing the synthetic yield of a compound having the structure of Formula (P)-Ia by interconverting a compound having the structure of Formula (M)-Ib, wherein the method comprises heating a solution comprising a compound of Formula (M)-Ib to the boiling point of the solvent.

In another embodiment, the solvent is an alcohol.

In another embodiment, the solvent is N-methylpyrrolidone or dimethylacetamide or combinations thereof.

In another embodiment, the solvent has a boiling point of 110° C.-150° C.

In another embodiment, the solvent is ethylene glycol.

In another embodiment, the solvent is n-butanol.

In another embodiment, there is provided methods of maximizing the synthetic yield of a compound having the structure of Formula (P)-Ia by adding a polar solvent to the post-interconversion mixture to precipitate the interconverted product comprising a compound of Formula (P)-Ia.

In another embodiment, the polar solvent is added to the post-interconversion mixture at a ratio (% $v_{added}/v_{initial}$) which affords the most precipitate with the least excess polar solvent.

In another embodiment, the polar solvent is added before cooling of the post-interconversion mixture.

In another embodiment, the polar solvent is added after cooling of the post-interconversion mixture.

In another embodiment, the polar solvent is water.

In another embodiment, water is added to about 75% $v_{added}/v_{initial}$.

In another embodiment, water is added to 80% $v_{added}/v_{initial}$.

In another embodiment, water is added to about 85% $v_{added}/v_{initial}$.

In another embodiment the method for isolating a compound of Formula (P)-Ia by interconverting a compound of Formula (M)-Ib is repeated multiple times.

In another embodiment the method for isolating a compound of Formula (P)-Ia by interconverting a compound of Formula (M)-Ib is repeated once, twice, thrice, or four times.

In another embodiment the method for isolating a compound of Formula (P)-Ia by interconverting a compound of Formula (M)-Ib is repeated twice.

In another embodiments the method for isolating a compound of Formula (P)-Ia by interconverting a compound of Formula (M)-Ib yields a ratio of a compound having the structure of Formula (P)-Ia, substantially free of the corresponding M isomer, to a compound having the structure of Formula (M)-Ib, substantially free of the corresponding P isomer, of about 2:1, about 3:1, about 4:1, about 5:1, about 6:1, about 7:1, about 8:1, about 9:1, or about 10:1.

In another embodiment the method for isolating a compound of Formula (P)-Ia by interconverting a compound of Formula (M)-Ib yields a ratio of a compound having the structure of Formula (P)-Ia, substantially free of the corresponding M isomer, to a compound having the structure of Formula (M)-Ib, substantially free of the corresponding P isomer, of about 5:1.

Non-limiting examples of Formula (M)-Ib compounds include the following compounds, or a derivative thereof:

| No. | Structure | Compound Name |
|---|---|---|
| 1b | 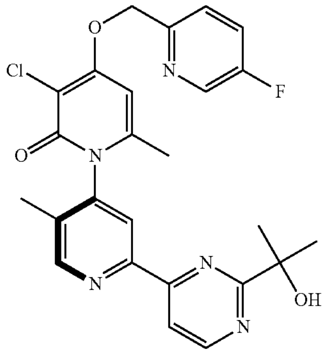 | (M)-3-chloro-4-((5-fluoropyridin-2-yl)methoxy)-2'-(2-(2-hydroxypropan-2-yl)pyrimidin-4-yl)-5',6-dimethyl-2H-[1,4'-bipyridin]-2-one |
| 2b | 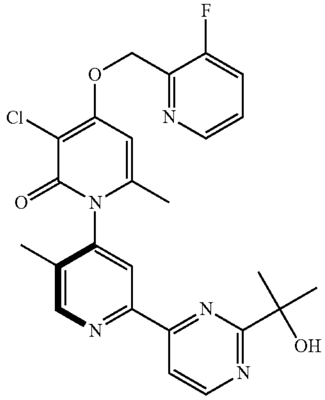 | (M)-3-chloro-4-((3-fluoropyridin-2-yl)methoxy)-2'-(2-(2-hydroxypropan-2-yl)pyrimidin-4-yl)-5',6-dimethyl-2H-[1,4'-bipyridin]-2-one |
| 3b | 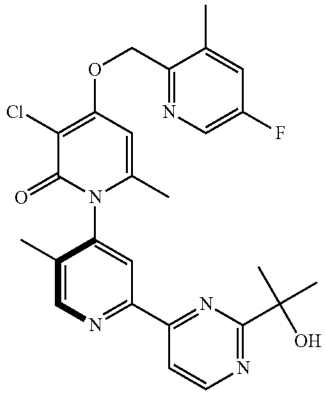 | (M)-3-chloro-4-((5-fluoro-3-methylpyridin-2-yl)methoxy)-2'-(2-(2-hydroxypropan-2-yl)pyrimidin-4-yl)-5',6-dimethyl-2H-[1,4'-bipyridin]-2-one |
| 4b | 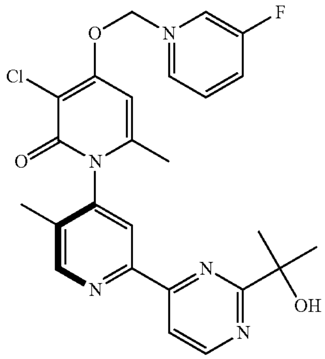 | (M)-3-chloro-4-((6-fluoropyridin-2-yl)methoxy)-2'-(2-(2-hydroxypropan-2-yl)pyrimidin-4-yl)-5',6-dimethyl-2H-[1,4'-bipyridin]-2-one |

-continued

| No. | Structure | Compound Name |
|---|---|---|
| 5b | 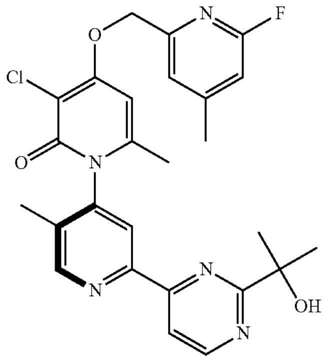 | (M)-3-chloro-4-((6-fluoro-4-methylpyridin-2-yl)methoxy)-2'-(2-(2-hydroxypropan-2-yl)pyrimidin-4-yl)-5',6-dimethyl-2H-[1,4'-bipyridin]-2-one |
| 6b | 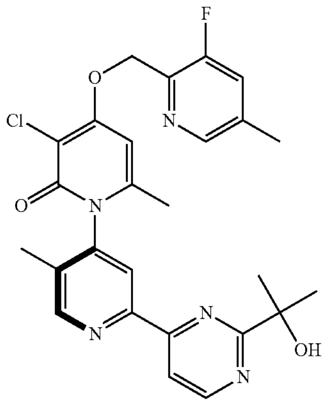 | (M)-3-chloro-4-((3-fluoro-5-methylpyridin-2-yl)methoxy)-2'-(2-(2-hydroxypropan-2-yl)pyrimidin-4-yl)-5',6-dimethyl-2H-[1,4'-bipyridin]-2-one |
| 7b | 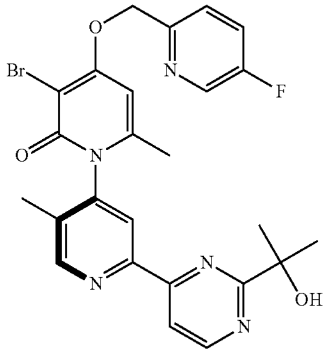 | (M)-3-bromo-4-((5-fluoropyridin-2-yl)methoxy)-2'-(2-(2-hydroxypropan-2-yl)pyrimidin-4-yl)-5',6-dimethyl-2H-[1,4'-bipyridin]-2-one |
| 8b | 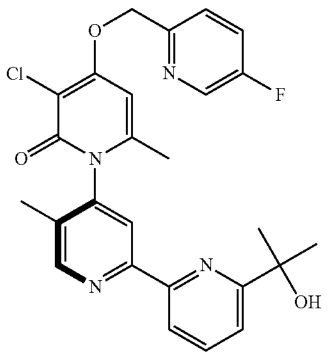 | (M)-3-chloro-4-((5-fluoropyridin-2-yl)methoxy)-6''-(2-hydroxypropan-2-yl)-5',6-dimethyl-2H-[1,4':2',2''-terpyridin]-2-one |

-continued

| No. | Structure | Compound Name |
|---|---|---|
| 9b | 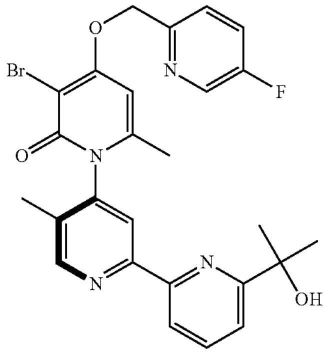 | (M)-3-bromo-4-((5-fluoropyridin-2-yl)methoxy)-6''-(2-hydroxypropan-2-yl)-5',6-dimethyl-2H-[1,4':2',2''-terpyridin]-2-one |
| 10b | 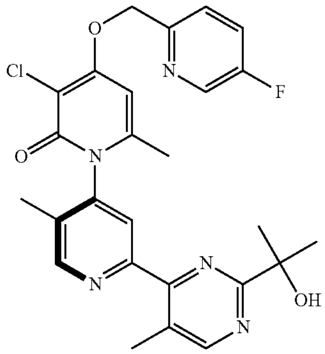 | (M)-3-chloro-4-((5-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 11b | 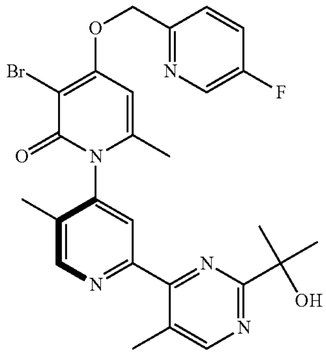 | (M)-3-bromo-4-((5-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 12b | 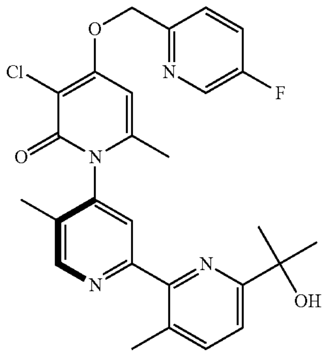 | (M)-3-chloro-4-((5-fluoropyridin-2-yl)methoxy)-6''-(2-hydroxypropan-2-yl)-3'',5',6-trimethyl-2H-[1,4':2',2''-terpyridin]-2-one |

-continued

| No. | Structure | Compound Name |
|---|---|---|
| 13b | 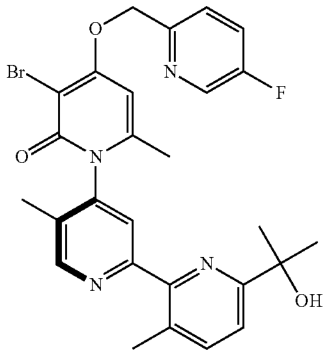 | (M)-3-bromo-4-((5-fluoropyridin-2-yl)methoxy)-6''-(2-hydroxypropan-2-yl)-3'',5',6-trimethyl-2H-[1,4':2',2''-terpyridin]-2-one |
| 14b | 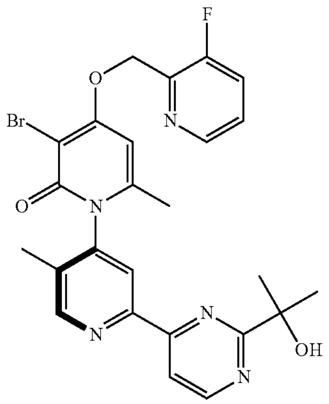 | (M)-3-bromo-4-((3-fluoropyridin-2-yl)methoxy)-2'-(2-(2-hydroxypropan-2-yl)pyrimidin-4-yl)-5',6-dimethyl-2H-[1,4'-bipyridin]-2-one |
| 15b | 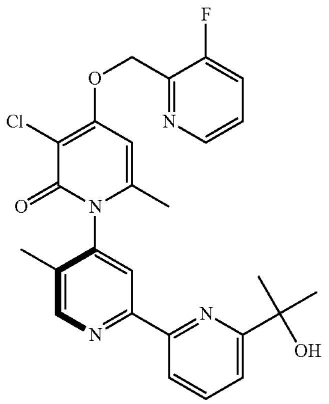 | (M)-3-chloro-4-((3-fluoropyridin-2-yl)methoxy)-6''-(2-hydroxypropan-2-yl)-5',6-dimethyl-2H-[1,4':2',2''-terpyridin]-2-one |
| 16b | 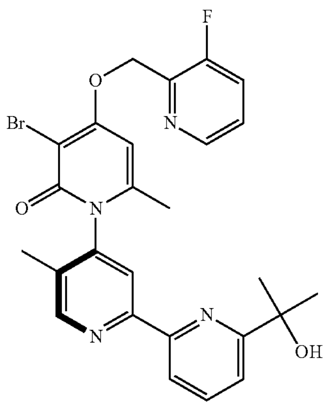 | (M)-3-bromo-4-((3-fluoropyridin-2-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 17b | 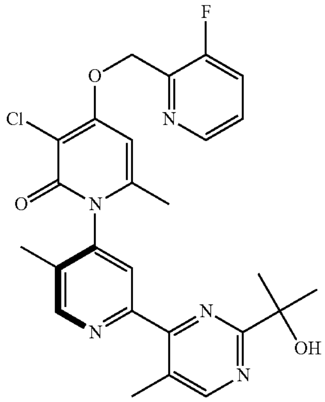 | (M)-3-chloro-4-((3-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 18b | 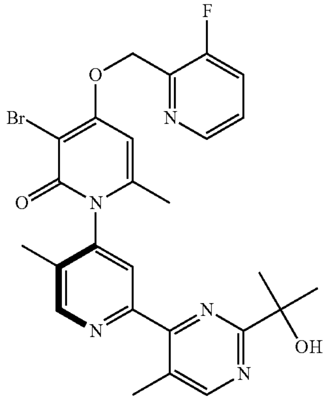 | (M)-3-bromo-4-((3-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 19b | 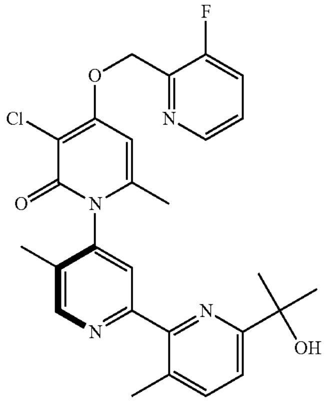 | (M)-3-chloro-4-((3-fluoropyridin-2-yl)methoxy)-6''-(2-hydroxypropan-2-yl)-3'',5',6-trimethyl-2H-[1,4':2',2''-terpyridin]-2-one |

-continued
| No. | Structure | Compound Name |
|---|---|---|
| 20b | 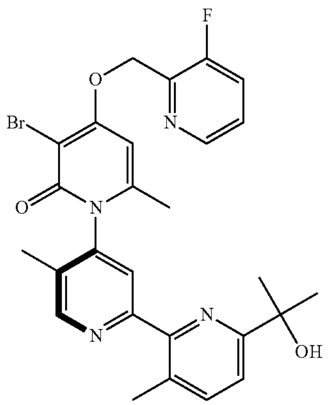 | (M)-3-bromo-4-((3-fluoropyridin-2-yl)methoxy)-6''-(2-hydroxypropan-2-yl)-3'',5',6-trimethyl-2H-[1,4':2',2''-terpyridin]-2-one |
| 21b | 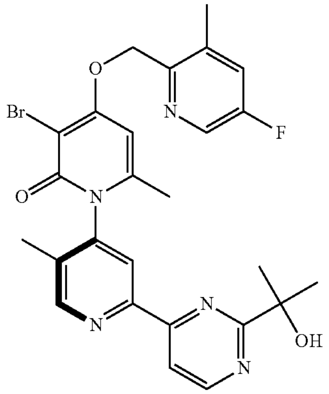 | (M)-3-bromo-4-((5-fluoro-3-methylpyridin-2-yl)methoxy)-2'-(2-(2-hydroxypropan-2-yl)pyrimidin-4-yl)-5',6-dimethyl-2H-[1,4'-bipyridin]-2-one |
| 22b | 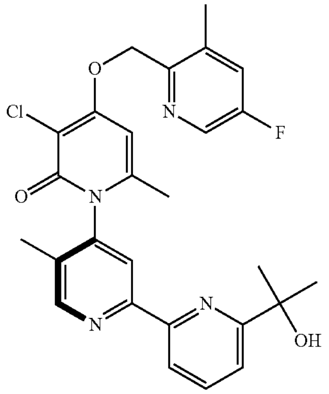 | (M)-3-chloro-4-((5-fluoro-3-methylpyridin-2-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 23b | 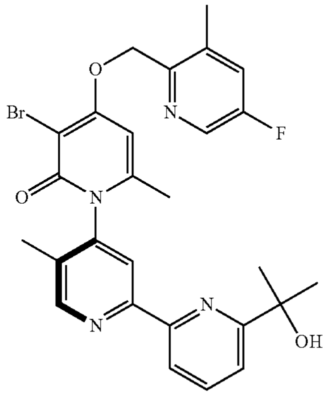 | (M)-3-bromo-4-((5-fluoro-3-methylpyridin-2-yl)methoxy)-6''-(2-hydroxypropan-2-yl)-5',6-dimethyl-2H-[1,4':2',2''-terpyridin]-2-one |
| 24b | 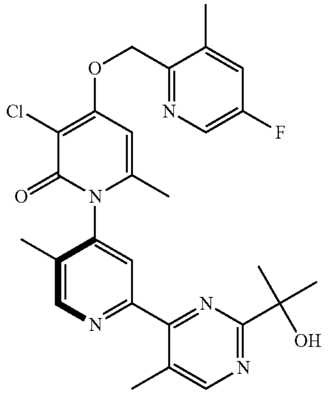 | (M)-3-chloro-4-((5-fluoro-3-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 25b | 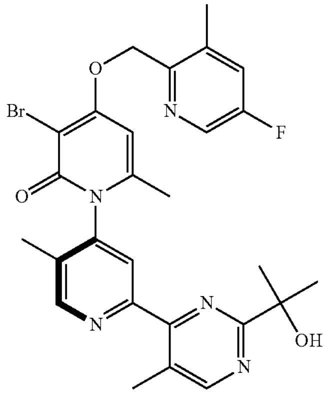 | (M)-3-bromo-4-((5-fluoro-3-methylpyridin-2-yl)methoxy)-2'-(2-(2-hydroxypropan-2-yl)-5-methylpyrimidin-4-yl)-5',6-dimethyl-2H-[1,4'-bipyridin]-2-one |

-continued

| No. | Structure | Compound Name |
|---|---|---|
| 26b | 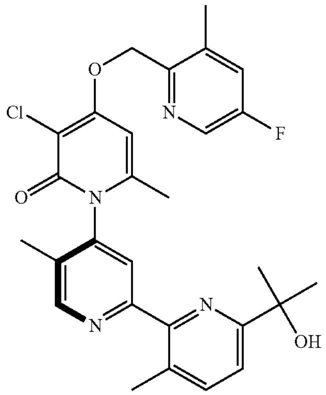 | (M)-3-chloro-4-((5-fluoro-3-methylpyridin-2-yl)methoxy)-6''-(2-hydroxypropan-2-yl)-3'',5',6-trimethyl-2H-[1,4':2',2''-terpyridin]-2-one |
| 27b | 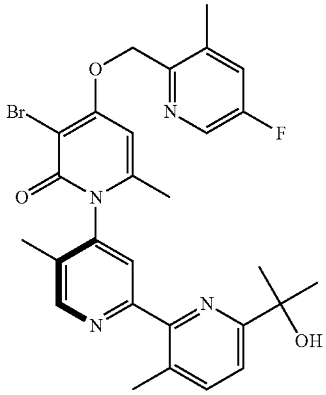 | (M)-3-bromo-4-((5-fluoro-3-methylpyridin-2-yl)methoxy)-6''-(2-hydroxypropan-2-yl)-3'',5',6-trimethyl-2H-[1,4':2',2''-terpyridin]-2-one |
| 28b | 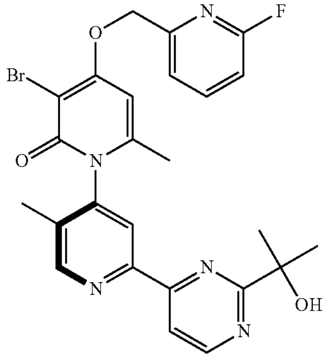 | (M)-3-bromo-4-((6-fluoropyridin-2-yl)methoxy)-2'-(2-(2-hydroxypropan-2-yl)pyrimidin-4-yl)-5',6-dimethyl-2H-[1,4'-bipyridin]-2-one |
| 29b | 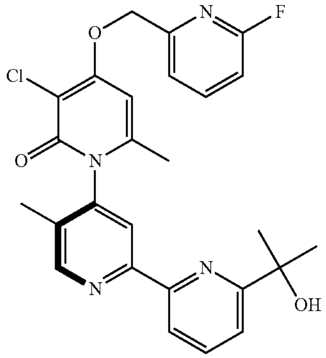 | (M)-3-chloro-4-((6-fluoropyridin-2-yl)methoxy)-6''-(2-hydroxypropan-2-yl)-5',6-dimethyl-2H-[1,4':2',2''-terpyridin]-2-one |

-continued

| No. | Structure | Compound Name |
| --- | --- | --- |
| 30b | 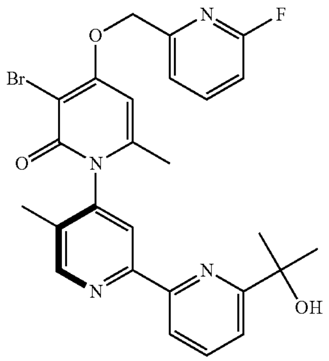 | (M)-3-bromo-4-((6-fluoropyridin-2-yl)methoxy)-6''-(2-hydroxypropan-2-yl)-5',6-dimethyl-2H-[1,4':2',2''-terpyridin]-2-one |
| 31b | 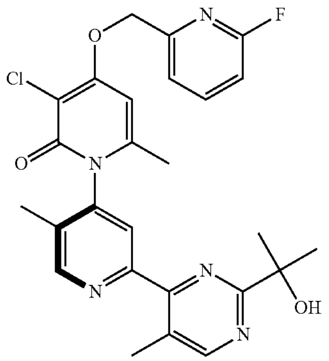 | (M)-3-chloro-4-((6-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 32b | 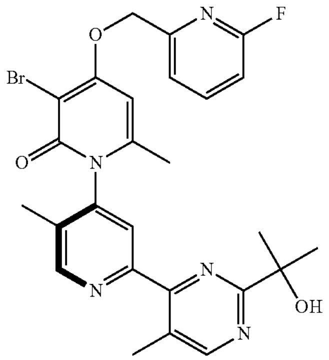 | (M)-3-bromo-4-((6-fluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 33b | 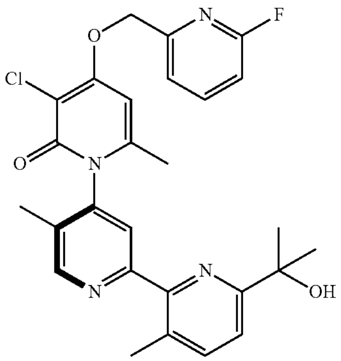 | (M)-3-chloro-4-((6-fluoropyridin-2-yl)methoxy)-6''-(2-hydroxypropan-2-yl)-3'',5',6-trimethyl-2H-[1,4':2',2''-terpyridin]-2-one |

-continued

| No. | Structure | Compound Name |
|---|---|---|
| 34b | 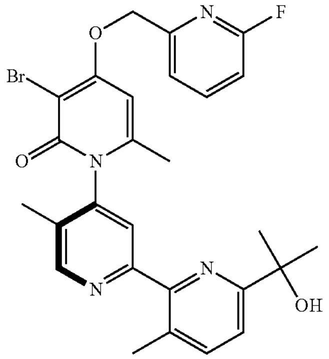 | (M)-3-bromo-4-((6-fluoropyridin-2-yl)methoxy)-6''-(2-hydroxypropan-2-yl)-3'',5',6-trimethyl-2H-[1,4':2',2''-terpyridin]-2-one |
| 35b | 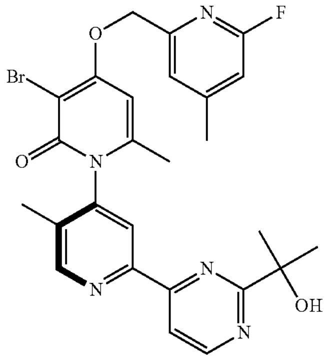 | (M)-3-bromo-4-((6-fluoro-4-methylpyridin-2-yl)methoxy)-2'-(2-(2-hydroxypropan-2-yl)pyrimidin-4-yl)-5',6-dimethyl-2H-[1,4'-bipyridin]-2-one |
| 36b | 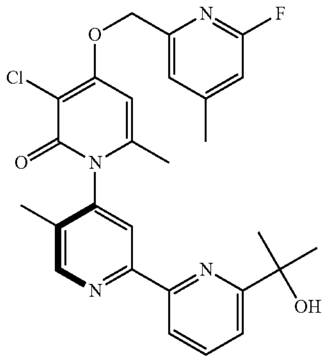 | (M)-3-chloro-4-((6-fluoro-4-methylpyridin-2-yl)methoxy)-6''-(2-hydroxypropan-2-yl)-5',6-dimethyl-2H-[1,4':2',2''-terpyridin]-2-one |
| 37b | 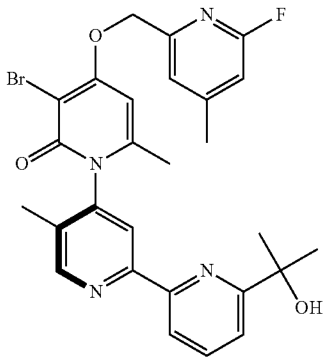 | (M)-3-bromo-4-((6-fluoro-4-methylpyridin-2-yl)methoxy)-6''-(2-hydroxypropan-2-yl)-5',6-dimethyl-2H-[1,4':2',2''-terpyridin]-2-one |

-continued

| No. | Structure | Compound Name |
|---|---|---|
| 38b | 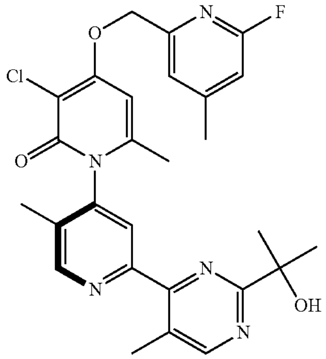 | (M)-3-chloro-4-((6-fluoro-4-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 39b | 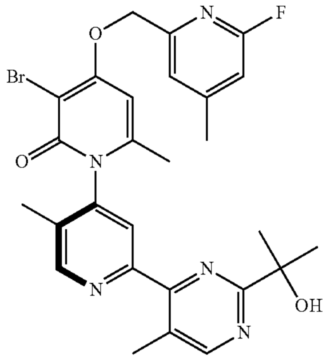 | (M)-3-bromo-4-((6-fluoro-4-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 40b | 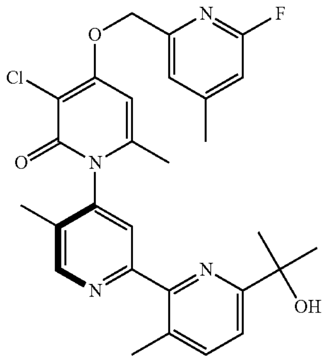 | (M)-3-chloro-4-((6-fluoro-4-methylpyridin-2-yl)methoxy)-6''-(2-hydroxypropan-2-yl)-3'',5',6-trimethyl-2H-[1,4':2',2''-terpyridin]-2-one |
| 41b | 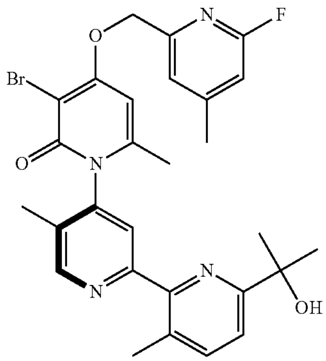 | (M)-3-bromo-4-((6-fluoro-4-methylpyridin-2-yl)methoxy)-6''-(2-hydroxypropan-2-yl)-3'',5',6-trimethyl-2H-[1,4':2',2''-terpyridin]-2-one |

-continued
| No. | Structure | Compound Name |
| --- | --- | --- |
| 42b | 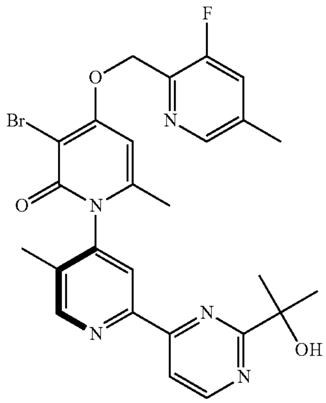 | (M)-3-bromo-4-((3-fluoro-5-methylpyridin-2-yl)methoxy)-2'-(2-(2-hydroxypropan-2-yl)pyrimidin-4-yl)-5',6-dimethyl-2H-[1,4'-bipyridin]-2-one |
| 43b | 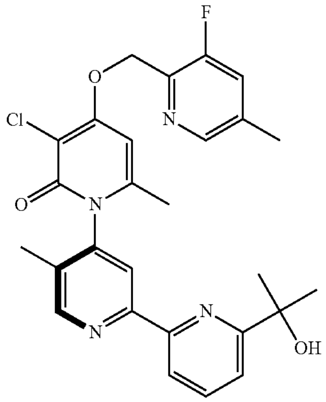 | (M)-3-chloro-4-((3-fluoro-5-methylpyridin-2-yl)methoxy)-6''-(2-hydroxypropan-2-yl)-5',6-dimethyl-2H-[1,4':2',2''-terpyridin]-2-one |
| 44b | 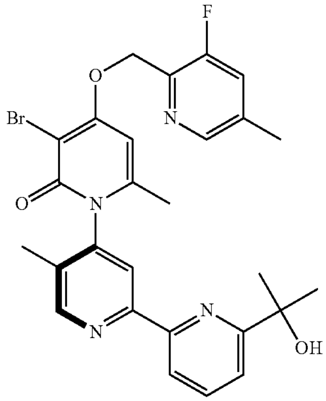 | (M)-3-bromo-4-((3-fluoro-5-methylpyridin-2-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 45b | 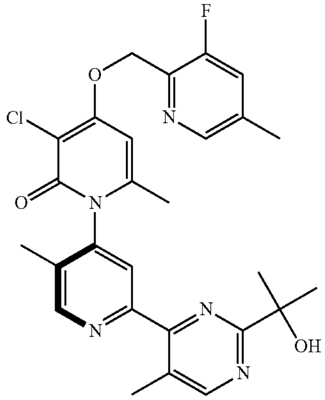 | (M)-3-chloro-4-((3-fluoro-5-methylpyridin-2-yl)methoxy)-2'-(2-(2-hydroxypropan-2-yl)-5-methylpyrimidin-4-yl)-5',6-dimethyl-2H-[1,4'-bipyridin]-2-one |
| 46b | 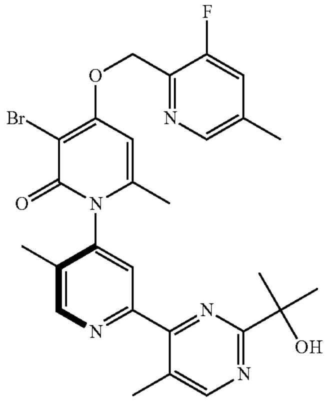 | (M)-3-bromo-4-((3-fluoro-5-methylpyridin-2-yl)methoxy)-2'-(2-(2-hydroxypropan-2-yl)-5-methylpyrimidin-4-yl)-5',6-dimethyl-2H-[1,4'-bipyridin]-2-one |

-continued

| No. | Structure | Compound Name |
| --- | --- | --- |
| 47b | 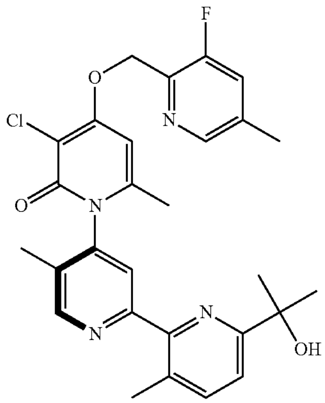 | (M)-3-chloro-4-((3-fluoro-5-methylpyridin-2-yl)methoxy)-6"-(2-hydroxypropan-2-yl)-3",5',6-trimethyl-2H-[1,4':2',2"-terpyridin]-2-one |
| 48b | 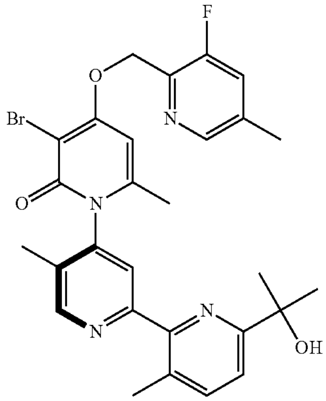 | (M)-3-bromo-4-((3-fluoro-5-methylpyridin-2-yl)methoxy)-6"-(2-hydroxypropan-2-yl)-3",5',6-trimethyl-2H-[1,4':2',2"-terpyridin]-2-one |

In another embodiment, there is provided methods for maximizing the synthetic yield of a compound having the structure of Formula (P)-IIIa by interconverting a compound having the structure of Formula (M)-IIIb:

(P)-IIIa

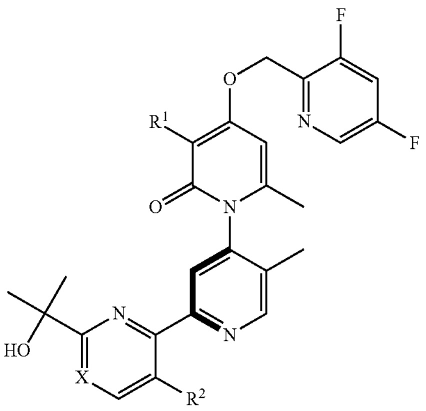

-continued (M)-IIIb

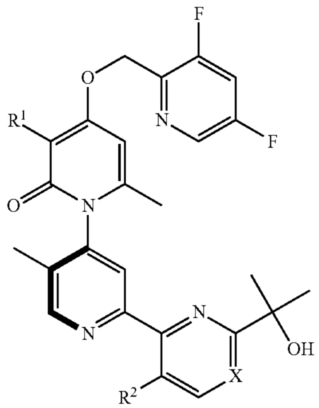

wherein:

X is CH or N;

$R^1$ is chloro or bromo;

$R^2$ is —H or methyl; or a derivative thereof, and wherein the method comprises heating a solution comprising a compound of Formula (M)-IIIb to a temperature at which the compound interconverts.

Non-limiting examples of Formula (M)-IIIb compounds include the following compounds, or a derivative thereof:

| No. | Structure | Compound Name |
|---|---|---|
| 49b | 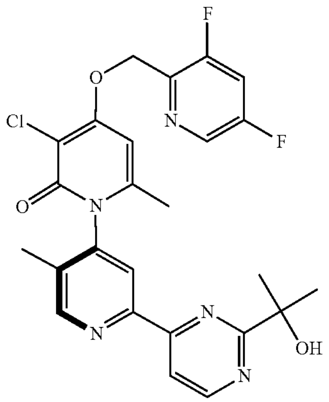 | (M)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one |
| 50b | 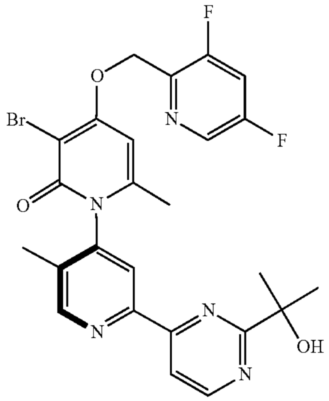 | (M)-3-bromo-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one |
| 51b | 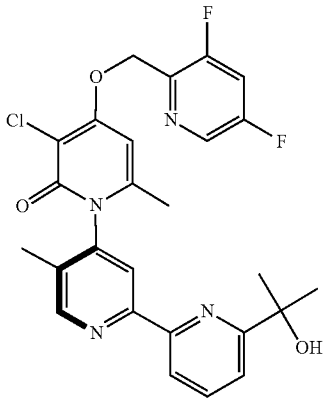 | (M)-3-chloro-4-((3,5-difluoropyridin-2-yl)methoxy-6''-(2-hydroxypropan-2-yl)-5',6-dimethyl-2H-[1,4':2',2''-terpyridin]-2-one |
| 52b | 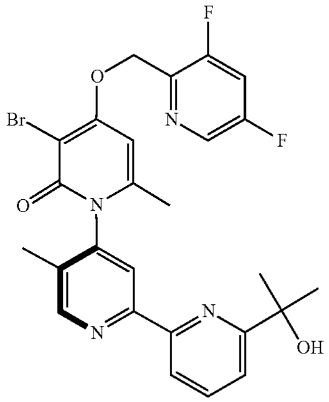 | (M)-3-bromo-4-((3,5-difluoropyridin-2-yl)methoxy)-6''-(2-hydroxypropan-2-yl)-5',6-dimethyl-2H-[1,4':2',2''-terpyridin]-2-one |

-continued
| No. | Structure | Compound Name |
|---|---|---|
| 53b | 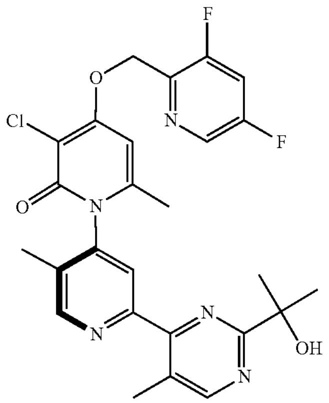 | (M)-3-chloro-4-((3,5-difluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 54b | 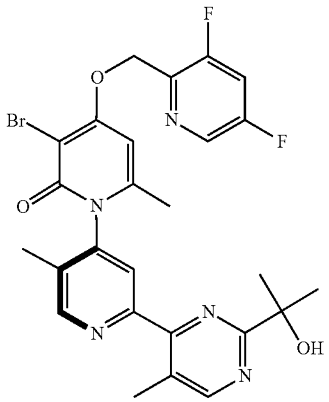 | (M)-3-bromo-4-((3,5-difluoropyridin-2-yl)methoxy)-2'-(2-(2-hydroxypropan-2-yl)-5-methylpyrimidin-4-yl)-5',6-dimethyl-2H-[1,4'-bipyridin]-2-one |
| 55b | 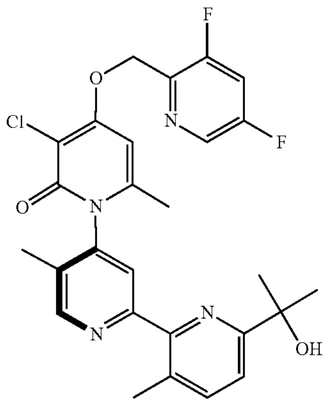 | (M)-3-chloro-4-((3,5-difluoropyridin-2-yl)methoxy)-6''-(2-hydroxypropan-2-yl)-3'',5',6-trimethyl-2H-[1,4':2',2''-terpyridin]-2-one |

-continued

| No. | Structure | Compound Name |
|---|---|---|
| 56b | 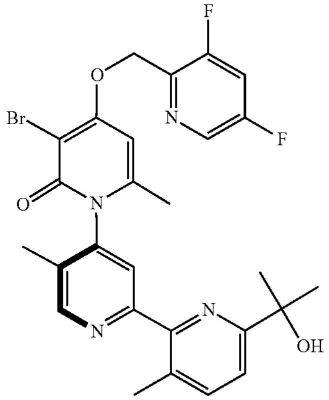 | (M)-3-bromo-4-((3,5-difluoropyridin-2-yl)methoxy)-6''-(2-hydroxypropan-2-yl)-3'',5',6-trimethyl-2H-[1,4':2',2''-terpyridin]-2-one |

In another embodiment, there is provided methods for maximizing the synthetic yield of a compound having the structure of Formula (P)-IVa by interconverting a compound having the structure of Formula (M)-IVb:

(P)-IVa

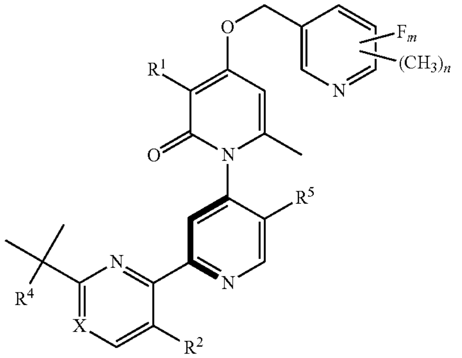

(M)-IVb

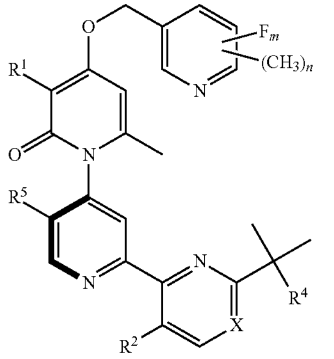

wherein:

X is CH or N;

$R^1$ is selected from the group consisting of H, $C_1$-$C_6$ alkyl, fluoro, chloro, bromo, cyano, or $-CF_3$;

$R^2$ is selected from the group consisting of H, methyl, cyano, or fluoro;

$R^4$ is selected from the group consisting of H, methyl, OH, and $-OCH_3$;

$R^5$ is H or $C_1$-$C_3$ alkyl;

m is 1 or 2;

n is 0 or 1; or a derivative thereof, and wherein the method comprises heating a solution comprising a compound of Formula (M)-IVb to a temperature at which the compound interconverts.

In another embodiment, there is provided methods for maximizing the synthetic yield of a compound having the structure of Formula (P)-Va by interconverting a compound having the structure of Formula (M)-Vb:

(P)-Va

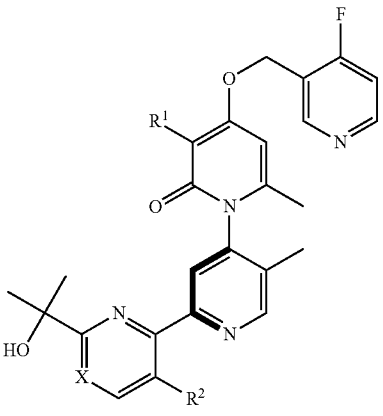

(M)-Vb

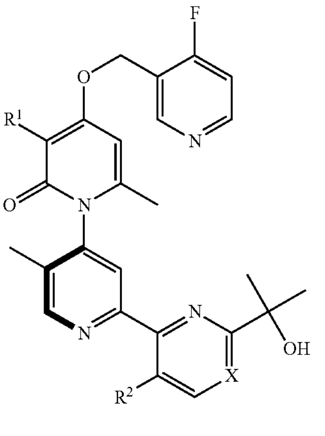

wherein:

X is CH or N;

$R^1$ is chloro or bromo;

$R^2$ is H or methyl;

a derivative thereof, and wherein the method comprises heating a solution comprising a compound of Formula (M)-Vb to a temperature at which the compound interconverts.

Non-limiting examples of Formula (M)-Vb compounds include the following compounds and a derivative thereof:

| No. | Structure | Compound Name |
|---|---|---|
| 57b | 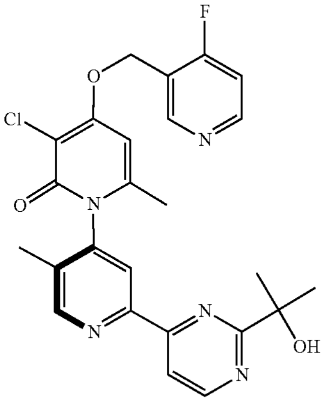 | (M)-3-chloro-4-((4-fluoropyridin-3-yl)methoxy)-2'-(2-(2-hydroxypropan-2-yl)pyrimidin-4-yl)-5',6-dimethyl-2H-[1,4'-bipyridin]-2-one |
| 58b | 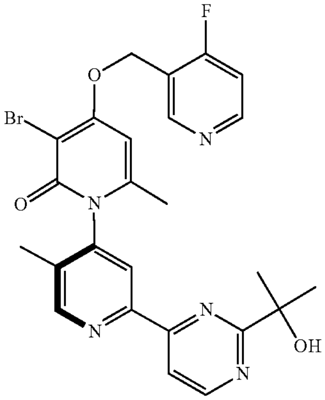 | (M)-3-bromo-4-((4-fluoropyridin-3-yl)methoxy)-2'-(2-(2-hydroxypropan-2-yl)pyrimidin-4-yl)-5',6-dimethyl-2H-[1,4'-bipyridin]-2-one |
| 59b | 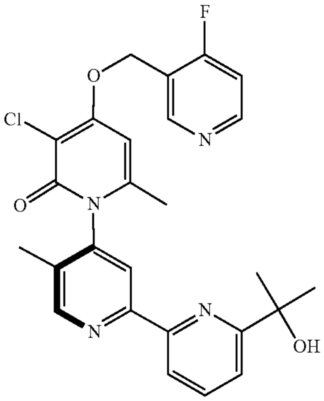 | (M)-3-chloro-4-((4-fluoropyridin-3-yl)methoxy)-6''-(2-hydroxypropan-2-yl)-5',6-dimethyl-2H-[1,4':2',2''-terpyridin]-2-one |

-continued

| No. | Structure | Compound Name |
|---|---|---|
| 60b | 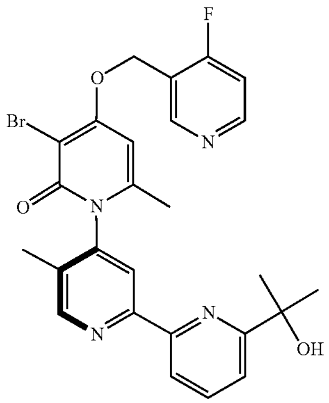 | (M)-3-bromo-4-((4-fluoropyridin-3-yl)methoxy)-6''-(2-hydroxypropan-2-yl)-5',6-dimethyl-2H-[1,4':2',2''-terpyridin]-2-one |
| 61b | 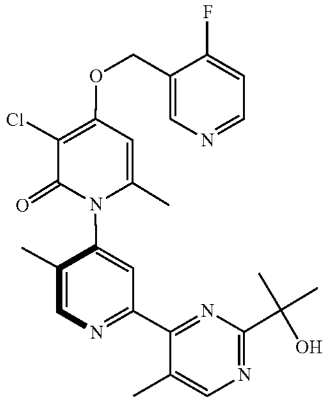 | (M)-3-chloro-4-((4-fluoropyridin-3-yl)methoxy)-2'-(2-(2-hydroxypropan-2-yl)-5-methylpyrimidin-4-yl)-5',6-dimethyl-2H-[1,4'-bipyridin]-2-one |
| 62b | 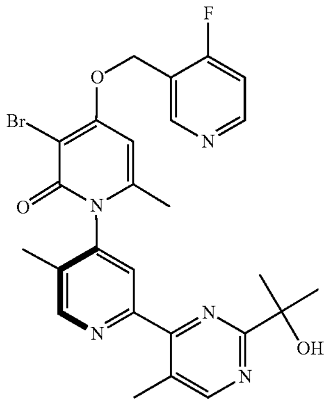 | (M)-3-bromo-4-((4-fluoropyridin-3-yl)methoxy)-2'-(2-(2-hydroxypropan-2-yl)-5-methylpyrimidin-4-yl)-5',6-dimethyl-2H-[1,4'-bipyridin]-2-one |
| 63b | 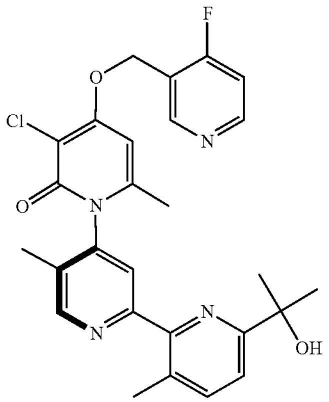 | (M)-3-chloro-4-((4-fluoropyridin-3-yl)methoxy)-6''-(2-hydroxypropan-2-yl)-3'',5',6-trimethyl-2H-[1,4':2',2''-terpyridin]-2-one |

-continued

| No. | Structure | Compound Name |
|---|---|---|
| 64b | 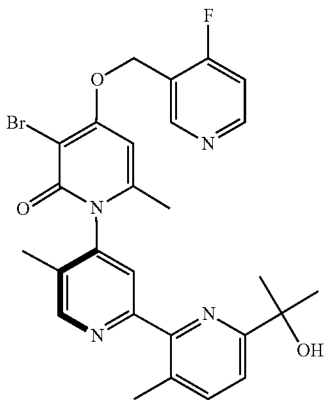 | (M)-3-bromo-4-((4-fluoropyridin-3-yl)methoxy)-6''-(2-hydroxypropan-2-yl)-3'',5',6-trimethyl-2H-[1,4':2',2''-terpyridin]-2-one |

In another embodiment, there is provided methods for maximizing the synthetic yield of a compound having the structure of Formula (P)-VIa by interconverting a compound having the structure of Formula (M)-VIb:

(P)-VIa

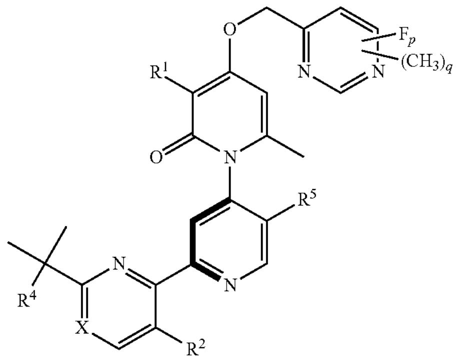

(M)-VIb

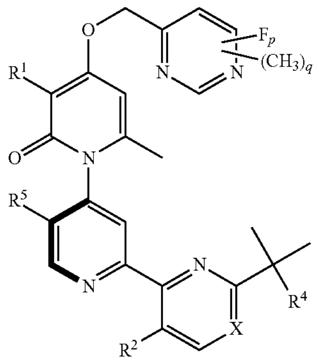

wherein:

X is CH or N;

$R^1$ is selected from the group consisting of H, $C_1$-$C_6$ alkyl, fluoro, chloro, bromo, cyano, or —$CF_3$;

$R^2$ is selected from the group consisting of H, methyl, cyano, or fluoro;

$R^4$ is selected from the group consisting of H, methyl, OH, and —$OCH_3$;

$R^5$ is H or $C_1$-$C_3$ alkyl;

p is 1;

q is 0 or 1;

a derivative thereof, and wherein the method comprises heating a solution comprising a compound of Formula (M)-VIb to a temperature at which the compound interconverts.

In another embodiment, there is provided methods for maximizing the synthetic yield of a compound having the structure of Formula (P)-VIIa by interconverting a compound having the structure of Formula (M)-VIIb:

(P)-VIIa

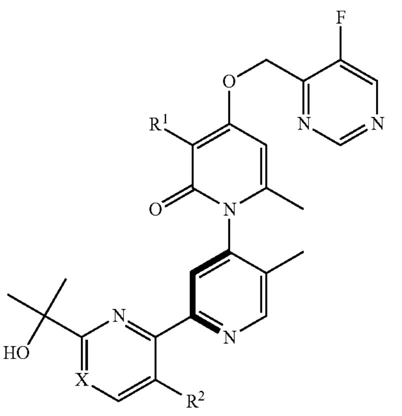

-continued (M)-VIIb

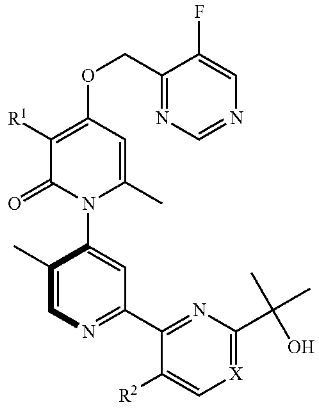

wherein:

X is CH or N;

$R^1$ is chloro or bromo;

$R^2$ is H or methyl a derivative thereof, and wherein the method comprises heating a solution comprising a compound of Formula (M)-VIb to a temperature at which the compound interconverts.

Non-limiting examples of Formula (M)-VIIb compounds include the following compounds and a derivative thereof:

| No. | Structure | Compound Name |
|---|---|---|
| 65b | 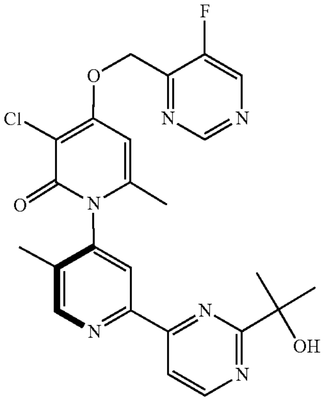 | (M)-3-chloro-4-((5-fluoropyrimidin-4-yl)methoxy)-2'-(2-(2-hydroxypropan-2-yl)pyrimidin-4-yl)-5',6-dimethyl-2H-[1,4'-bipyridin]-2-one |
| 66b | 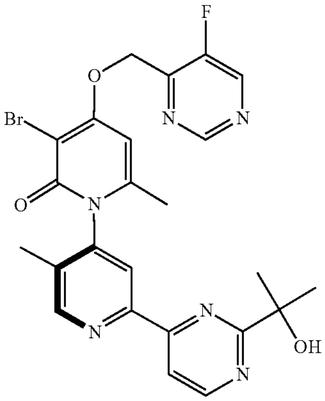 | (M)-3-bromo-4-((5-fluoropyrimidin-4-yl)methoxy)-2'-(2-(2-hydroxypropan-2-yl)pyrimidin-4-yl)-5',6-dimethyl-2H-[1,4'-bipyridin]-2-one |

-continued

| No. | Structure | Compound Name |
|---|---|---|
| 67b | 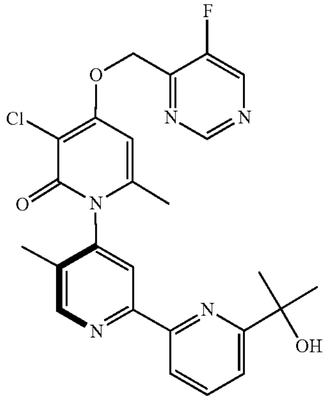 | (M)-3-chloro-4-((5-fluoropyrimidin-4-yl)methoxy)-6''-(2-hydroxypropan-2-yl)-5',6-dimethyl-2H-[1,4':2',2''-terpyridin]-2-one |
| 68b | 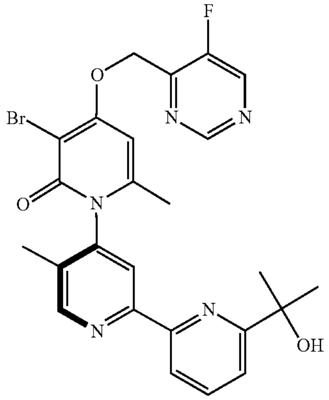 | (M)-3-bromo-4-((5-fluoropyrimidin-4-yl)methoxy)-6''-(2-hydroxypropan-2-yl)-5',6-dimethyl-2H-[1,4':2',2''-terpyridin]-2-one |
| 69b | 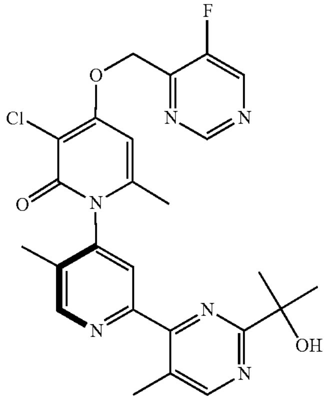 | (M)-3-chloro-4-((5-fluoropyrimidin-4-yl)methoxy)-2'-(2-(2-hydroxypropan-2-yl)-5-methylpyrimidin-4-yl)-5',6-dimethyl-2H-[1,4'-bipyridin]-2-one |
| 70b | 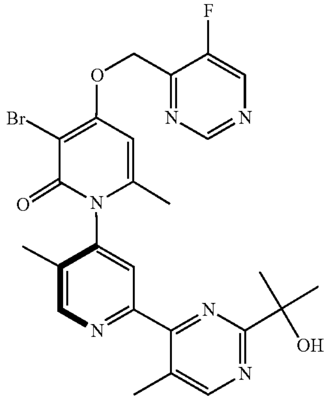 | (M)-3-bromo-4-((5-fluoropyrimidin-4-yl)methoxy)-2'-(2-(2-hydroxypropan-2-yl)-5-methylpyrimidin-4-yl)-5',6-dimethyl-2H-[1,4'-bipyridin]-2-one |

-continued

| No. | Structure | Compound Name |
|---|---|---|
| 71b | 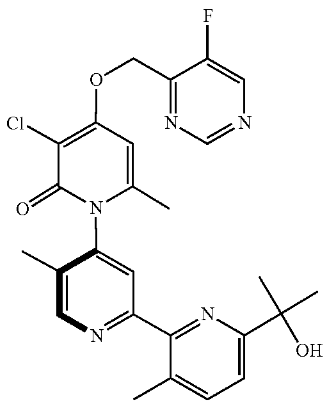 | (M)-3-chloro-4-((5-fluoropyrimidin-4-yl)methoxy)-6''-(2-hydroxypropan-2-yl)-3'',5',6-trimethyl-2H-[1,4':2',2''-terpyridin]-2-one |
| 72b | 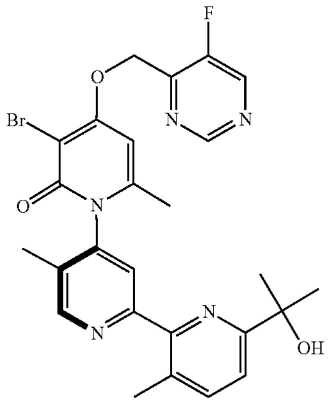 | (M)-3-bromo-4-((5-fluoropyrimidin-4-yl)methoxy)-6''-(2-hydroxypropan-2-yl)-3'',5',6-trimethyl-2H-[1,4':2',2''-terpyridin]-2-one |

In certain embodiments each of the compounds of Formula (M)-Ib, Formula (M)-IIb, Formula (M)-IIIb, Formula (M)-IVb, Formula (M)-Vb, Formula (M)-VIb, and Formula (M)-VIIb, are substantially free of their corresponding P isomer.

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1 and 2 below. Solvents and reagents, whose synthetic preparations are not described below, can be purchased at Sigma-Aldrich or Fisher Scientific.

The compounds of the present invention can be prepared using the methods illustrated in the general synthetic schemes and experimental procedures detailed below. These general synthetic schemes and experimental procedures are presented for purposes of illustration and are not intended to be limiting. The starting materials used to prepare the compounds of the present invention are commercially available or can be prepared using routine methods known in the art.

Exemplary methods of maximizing yield by conformational interconversion are also illustrated below. Example solvents, solvent mixtures, and azeotropes used for interconversion by reflux are not meant to be limiting. Example solvents, solvent mixtures, azeotropes, and processes used to interconvert or recover product or reduce residual solvent levels are not meant to be limiting. Any solvent or solvent mixture having the appropriate thermal characteristics, being ICH Class II or above, having low residual solvent levels, and permitting some mechanism for product recovery post-interconversion is suited for the purposes of this method. Use of some solvents may result in production of more impurities in the post-racemization mixture than others. It is preferred that the solvents of this disclosure have a more desirable relative impurity profile.

Any solvent or azeotrope with a boiling point higher than the $T_{onset}$ of the interconversion and a boiling point lower than the decomposition temperature would be preferred.

For example, Compound 49b has a decomposition temperature range of 240° C.-300° C. and was found to interconvert in NMP at 138° C. The boiling point at of NMP is 138° C. (at 1 atm); below the decomposition temperature range of Compound 49b. Therefore, NMP would be a preferred solvent to use for the interconversion of Compound 49b.

In another example, Compound 49b was found to interconvert in ethylene glycol at ~114° C. The boiling point of ethylene glycol is 197° C. (at 1 atm); below the decomposition temperature range of Compound 49b. Therefore, ethylene glycol would be a preferred solvent for the interconversion of Compound 49b.

ICH Class II or III includes any solvent or azeotrope with non-genotoxicity in animals or, at most, possible causative agents of irreversible toxicity satisfies this criterion. These solvents or azeotropes may be suspected of other significant but reversible toxicities and satisfy this criterion. The entire ICH Q3C series of guidance publications is incorporated by reference.

Class II Solvents: Acetonitrile, Chlorobenzene, Chloroform, Cumene, Cyclohexane, 1,2-Dichloroethene, Dichloromethane, 1,2-Dimethoxyethane, N,N-Dimethylacetamide, N,N-Dimethylformamide, 1,4-Dioxane, 2-Ethoxyethanol, Ethyleneglycol, Formamide, Hexane, Methanol, 2-Methoxyethanol, Methylbutyl ketone, Methylcyclohexane, N-Methylpyrrolidone, Nitromethane, Pyridine, Sulfolane, Tetrahydrofuran, Tetralin, Toluene, 1,1,2-Trichloroethene, and Xylene.

ICH Class III: Any solvent or azeotrope which is not known as a human health hazard at levels normally accepted in pharmaceuticals.

Class III Solvents: Acetic acid, Acetone, Anisole, 1-Butanol, 2-Butanol, Butyl acetate, tert-Butylmethyl ether, Dimethyl sulfoxide, Ethanol, Ethyl acetate, Ethyl ether, Ethyl formate, Formic acid, Heptane, Isobutyl acetate, Isopropyl acetate, Methyl acetate, 3-Methyl-1-butanol, Methylethyl ketone, Methylisobutyl ketone, 2-Methyl-1-propanol, Pentane, 1-Pentanol, 1-Propanol, 2-Propanol, and Propyl Acetate Any solvent or azeotrope which results in the drug product containing no higher levels of residual solvents than can be supported by safety data would be preferred. Based on International Council for Harmonisation of Technical Requirements for Pharmaceuticals for Human Use (ICH) guidelines, specifically, Option 1 (assumed 10 g or lower administered daily) in Q3C(R5) Impurities: Guideline for Residual Solvents. This document is incorporated by reference.

For example, ethylene glycol has a maximum limit of 620 ppm.

As another example, NMP has a maximum limit of 530 ppm.

Any solvent, solvent mixture or azeotrope which has characteristics allowing for product recovery after interconversion would be preferred. For example, addition of a polar solvent to the post-interconversion mixture may precipitate an amount of interconverted product. Certain ratios of polar solvent to the interconversion solvent may afford higher precipitation levels of interconverted product.

For example, Compound 49b may be interconverted using ethylene glycol and addition of pure water to the post-interconversion mixture comprising ethylene glycol to an about 75% v/v (based on starting solution) allows for precipitation of at least 75-85% of the interconversion product.

In another example, when Compound 49b is interconverted in NMP, addition of pure water to the post-interconversion mixture comprising NMP allows for precipitation of about at least 70% of interconverted product.

Compounds interconverted in this invention are equilibrated with no or relatively small production of impurities and no or relatively small losses of mass balance. For example, the destructive melt decomposition onset temperature is ca. 240° C.-300° C. based on TGA and DSC for exemplary Compound 49b. Dry solids based interconversion temperature is ca. 170° C.-208° C. based on TGA and DSC for exemplary Compound 49b. However, liquid based interconversion temperature (or $T_{onset\ of\ interconversion}$) is ~113° C. for exemplary Compound 49b in ethylene glycol. For exemplary Compound 49b, the gap between dry solid interconversion temperature and destructive melt decomposition temperature is ca. 20° C., while the gap between liquid based interconversion temperature and destructive melt decomposition temperature is 125° C. in ethylene glycol. This increase in the gap between dry solid interconversion temperature and destructive melt decomposition onset temperature and to liquid based interconversion temperature and destructive melt decomposition onset temperature is unexpected. Additionally, interconversion temperature is about 138° C. in NMP, which affords a gap between interconversion and destructive decomposition temperature of about 67° C. This is another example of an increase in the workable temperature gap relative to the dry solid based interconversion temperature.

This disclosure outlines a method to significantly increase recovery of atropisomers with a negative optical rotation through recycling of waste atropisomers with a positive optical rotation with no modification to the original synthesis outlined in Scheme 1 or 2. Such recycling would greatly increase the cumulative maximum recovery of atropisomers with a negative optical rotation with relatively few unit operations.

Representative Synthetic Methods

Representative procedures for the preparation of compounds of this disclosure are outlined in Schemes 1 and 2. The substituted pyridine starting material can be purchased or prepared using methods known in the art with a representative procedure provided as an intermediate. Scheme 1 highlights the synthesis of the fully elaborated 1,4'-bipyridin-2-ones. The synthesis of pyridinone 1c can be accomplished by reaction of acetal 1a and pyridine 1b in a solvent such as dioxane. Alkylation of the phenol of 1c with the desired heteroaryl substituent ($R^3$) gives alkylated 1d. Pyridinone 1d may be converted to the title compound via one of three routes depending on the $R^2$ and X-substituents. For instance, if $R^2$ is methyl, reaction of 1d with a vinyl tin reagent in the presence of a palladium catalyst provides methyl ketone 1i. Halogenation of 1i using N-chlorosuccinimide (or N-bromosuccinimide if the corresponding bromo is desired) in a solvent such as isopropanol provides 1j. In situ enamine formation by reaction of 1j with N,N-dimethylformamide dimethyl acetal provides an intermediate, which is then reacted with 2-hydroxy-2-methylpropionamidine in a solvent such as DMF to give pyridinone 1g. Alternatively, if X is N 1 d may be carboxylated by treating the halide with carbon monoxide in the presence of a palladium catalyst in ethanol to give ester 1e. Hydrolysis of the ester of 1e with lithium hydroxide in water followed by treating the intermediate carboxylic acid with CDI, and subsequently with methoxymethylamine and an amine base such as diisopropylethylamine under Weinreb conditions gives 1h. Reaction of the Weinreb amide 1h with the desired $R^2$ Grinard reagent in a solvent such as THF provides 1i. Ketone 1i is then converted to 1j and then the final compound 1g, as indicated above. Another option to set the pyridine or pyrimidine D-ring is to react 1d with the desired boronic acid under Suzuki conditions using an appropriate palladium catalyst to give the coupled intermediate which is then halogenated using NCS or NBS to provide 1f. Addition of methyl magnesium bromide to if in a solvent such as THF provides the title compound 1g. Resulting equilibrated mixtures of atropisomers can be resolved by supercritical fluid chromatography with a mobile phase of carbon dioxide and ethanol. Individual atropisomers may then conformationally interconverted by dissolution in a solvent such as NMP or ethylene glycol and heating to the appropriate internal temperature for interconversion. Product is recovered by addition of water to the post-interconversion solution and precipitation followed by resolved by supercritical fluid chromatography with a mobile phase of carbon dioxide and ethanol.
Scheme 1
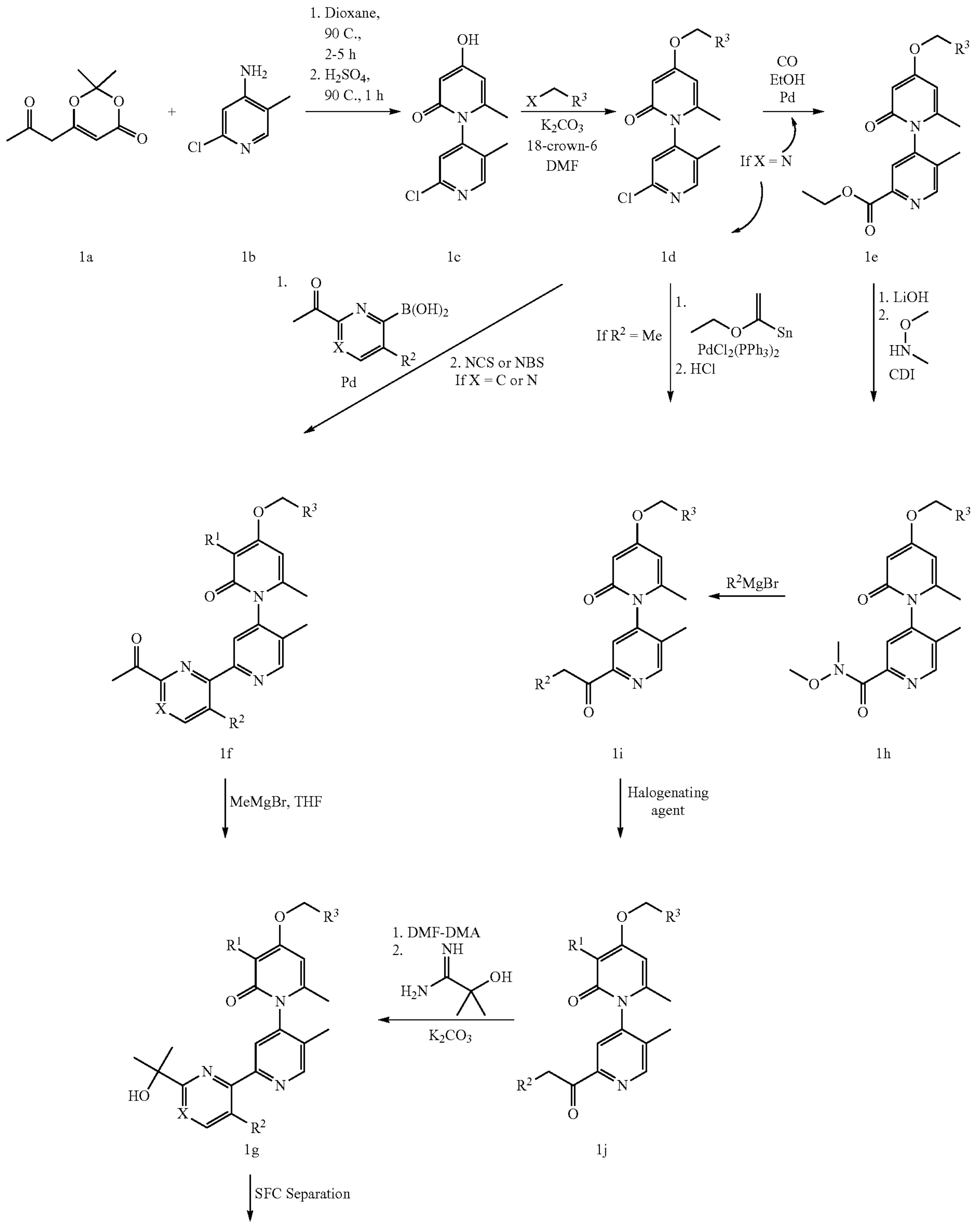

-continued

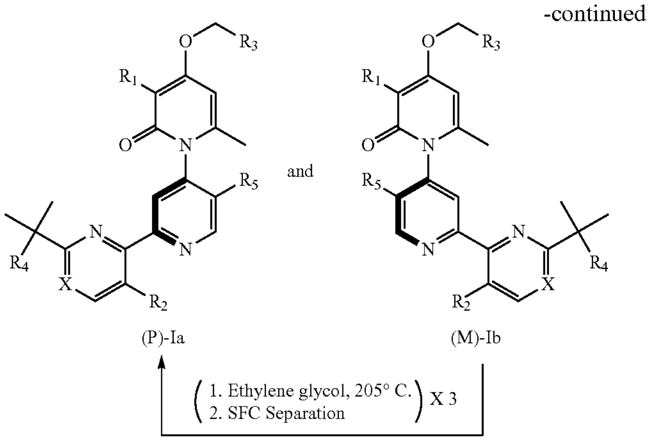

(P)-Ia and (M)-Ib

The synthesis of the desired compounds wherein the benzyl substituent $R^3$ is added in the last step is shown in Scheme 2. Pyridinone 2c can be accomplished by reaction of acetal 2a and pyridine 2b in a solvent such as dioxane as described in Scheme 1. Protection of the phenol of 2c with para-methoxybenzyl bromide gives benzylated 2d. Reaction of 2d with a vinyl tin reagent in the presence of a palladium catalyst provides methyl ketone 2e. Halogenation of 1e using N-chlorosuccinimide (or N-bromosuccinimide if the corresponding bromo is desired) in a solvent such as iso-propanol provides 2f. In situ enamine formation by reaction of 2f with N,N-dimethylformamide dimethyl acetal provides an intermediate, which is then reacted with 2-hydroxy-2-methylpropionamidine in a solvent such as DMF to give pyrimidinone 2g. Deprotection of the benzyl group by treating 2g with an acid such as TFA or HCl provides 2h. Alkylation of phenol 2 h with the desired benzyl halide substituent ($R^3CH_2Br$ or $R^3CH_2C_1$) provides the desired pyridinones 2i. Resulting equilibrated mixtures of atropisomers can be resolved by supercritical fluid chromatography with a mobile phase of carbon dioxide and ethanol. Individual atropisomers may then conformationally interconverted by dissolution in a solvent such as NMP or ethylene glycol and heating to the appropriate internal temperature for interconversion. Product is recovered by addition of water to the post-interconversion solution and precipitation then resolved by supercritical fluid chromatography with a mobile phase of carbon dioxide and ethanol.

Scheme 2

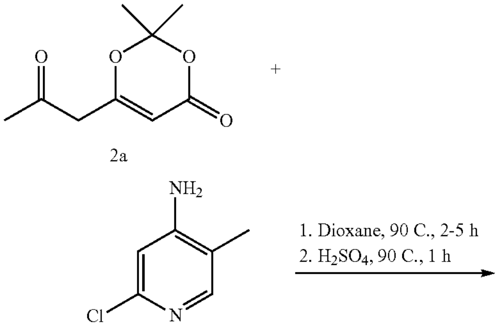

2a

2b

-continued

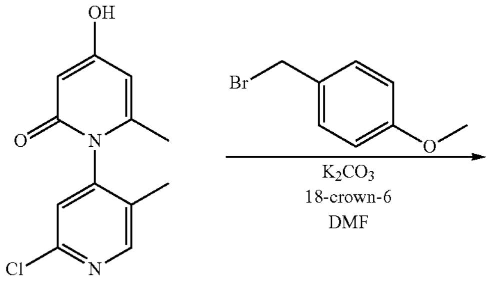

2c

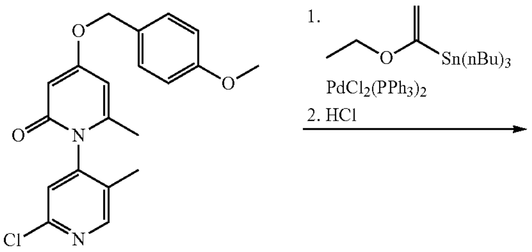

2d

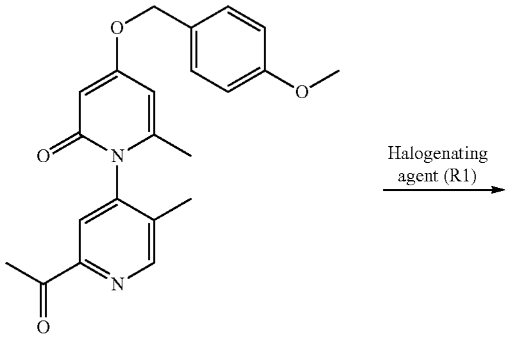

2e

-continued

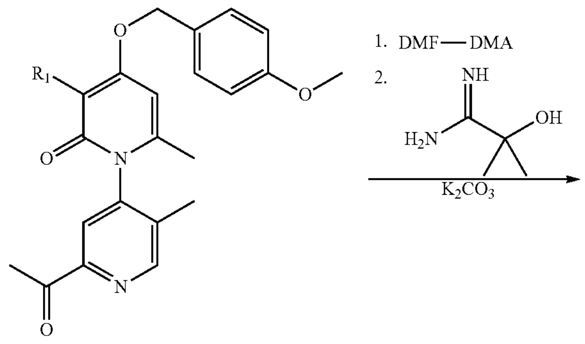

2f

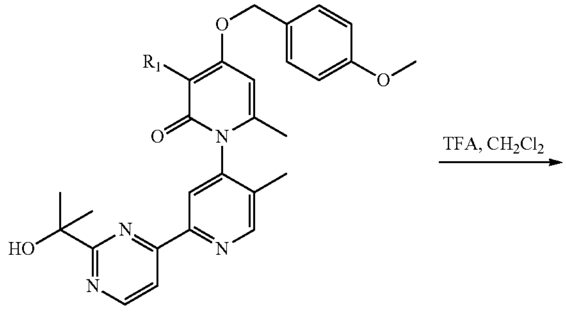

2g

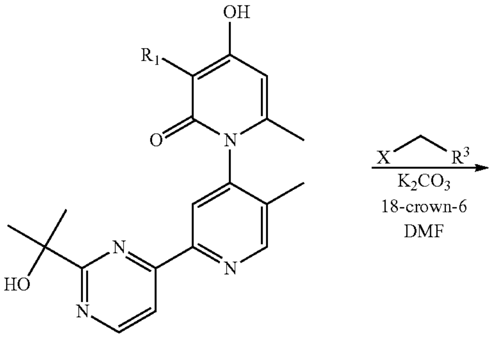

2h

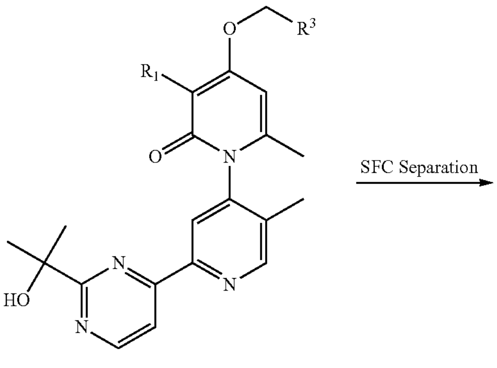

2f

-continued

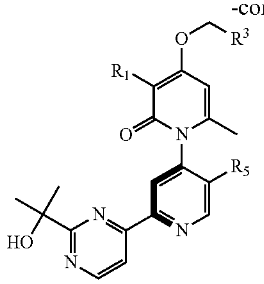

and

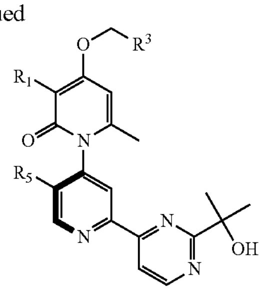

(P)-Ia (M)-Ib

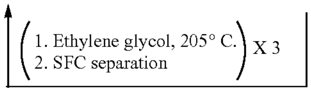

Example 1: Synthesis of Compound 49a

Preparation of 2-chloromethyl-3,5-difluoro-pyridine

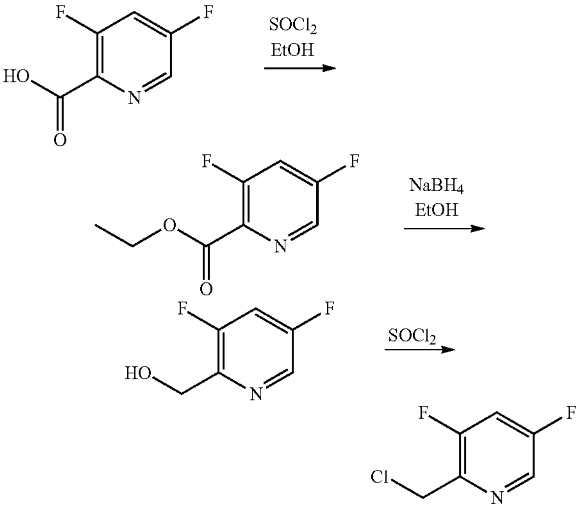

Step A: Preparation of 3,5-Difluoro-Pyridine-2-Carboxylic Acid Ethyl Ester

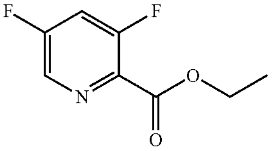

To a suspension of 3,5-difluoropyridine-2-carboxylic acid (2.0 g, 12.6 mmol) in ethanol (5 mL), cooled using an ice water bath, was added thionyl chloride (2 mL) in a dropwise manner. The solution was heated at 60° C. for 3 h. The reaction was returned to ambient temperature and was concentrated in vacuo to provide the ethyl ester, hydrochloride salt as a yellow oil (2.5 g).

Step B: Preparation of (3,5-Difluoro-Pyridin-2-Yl)-Methanol

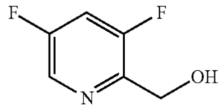

To a solution of 3,5-difluoro-pyridine-2-carboxylic acid ethyl ester of part A (2.5 g, 12.6 mmol) in ethanol (10 mL), cooled using an ice water bath, was added sodium borohydride (1.43 g, 37.8 mmol) in a portion wise manner. The solution was stirred at 0° C. for thirty minutes and at ambient temperature for 2 h. The reaction was returned to 0° C. and saturated ammonium chloride was added dropwise. The solvent was removed in vacuo and the resulting residue was partitioned between ethyl acetate and water. The organic layer was washed with saturated ammonium chloride, water and brine, and dried over magnesium sulfate. The slurry was filtered and concentrated to provide the alcohol as a yellow oil (1.8 g): MS (ES) m/e 146 (M+H).

Step C: Preparation of 2-Chloromethyl-3,5-Difluoro-Pyridine

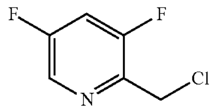

To a solution of (3,5-difluoro-pyridin-2-yl)-methanol from part B (1.8 g, 12.3 mmol) in dichloromethane (20 mL) was added three drops of N,N-dimethylformamide and cooled using an ice water bath. Thionyl chloride (2 mL) was added dropwise and the solution was stirred at ambient temperature for one hour. The solution was concentrated in vacuo to provide the chloro compound as a light brown liquid (1.75 g).

Compound 49a: Preparation of 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one

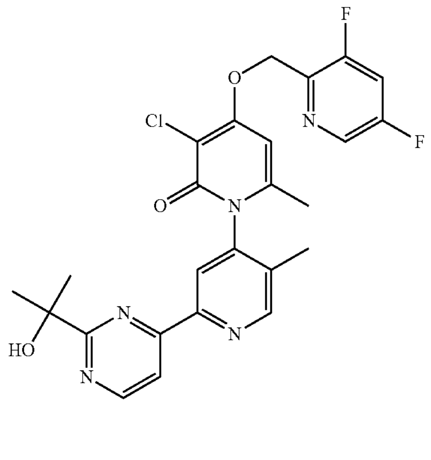 [SMILES: Cc1cnc(-c2ccnc(C(C)(C)O)n2)cc1-n1c(C)cc(OCc2ncc(F)cc2F)c(Cl)c1=O]

Step A: Preparation of 2'-chloro-4-hydroxy-6,5'-dimethyl-[1,4']bipyridinyl-2-one

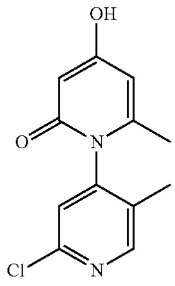 [SMILES: Cc1cnc(Cl)cc1-n1c(C)cc(O)cc1=O]

To a screw top vial with rubber septa inset was added 2,2-dimethyl-6-(2-oxo-propyl)-[1,3]dioxin-4-one, prepared as described in Organic Letters, 11(21), 4910-4913; 2009, (500 mg, 2.7 mmol) and 2-chloro-5-methyl-pyridin-4-ylamine (575 mg, 4 mmol, 1.5 eq). The mixture was dissolved in anhydrous 1,4-dioxane (10 mL). Once the mixture was homogeneous the vial was placed on a stirrer/hot plate preset to 90° C. The reaction vessel was heated at this temperature for 3.5 h. The reaction vial was removed from heat and analyzed by HPLC which showed that the reaction was >95% complete. The vial was placed back on the hot plate. To the heated mixture was added $H_2SO_4$ (250 μL) and the reaction was heated for 1 h. The reaction vial was removed from the heat and after cooling to ambient temperature, the dioxane was removed by passing a stream of air over the top of the open vial to give a brown residue. Water (~4 mL) was added to the vial, and the mixture was stirred for 30 min. The resulting tan solid was filtered off with washing from additional water and the diethyl ether to give the desired product (531 mg, 57% based on being the sulfate salt) as a tan solid which by HPLC was ~95% pure: MS (ES) m/e 250 (M+H).

Step B: Preparation of 2'-chloro-4-((4-methoxybenzyl)oxy)-5',6-dimethyl-2H-[1,4'-bipyridin]-2-one

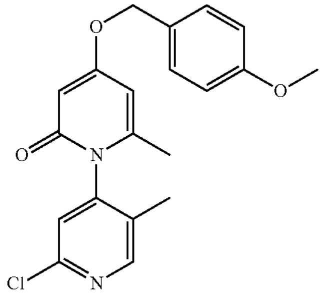 [SMILES: COc1ccc(COc2cc(C)n(-c3cc(Cl)ncc3C)c(=O)c2)cc1]

To a solution of 2'-chloro-4-hydroxy-6,5'-dimethyl-[1,4']bipyridinyl-2-one of part A (6.0 g, 20.1 mmol) in N,N-dimethylformamide (20 mL) was added 4-methoxybenzylchloride (2.73 mL, 20.1 mmol), potassium carbonate (6.93 g, 50.2 mmol) and 18-crown-6 (100 mg). The slurry was heated at 60° C. for 3 h and was stirred at ambient temperature for 18 h. The reaction mixture was partitioned between ethyl acetate and water. The organic layer was washed with water and brine and dried over magnesium sulfate. The solution was concentrated in vacuo to provide a brown oil. Normal phase chromatography (ethyl acetate/heptane) provided the alkylated product as a light yellow solid (4.6 g): MS (ES) m e 371 (M+H).

Step C: Preparation of 2'-acetyl-4-((4-methoxybenzyl)oxy)-5',6-dimethyl-2H-[1,4'-bipyridin]-2-one

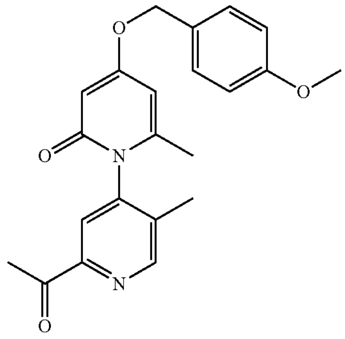 [SMILES: COc1ccc(COc2cc(C)n(-c3cc(C(C)=O)ncc3C)c(=O)c2)cc1]

A solution of 2'-chloro-4-((4-methoxybenzyl)oxy)-5',6-dimethyl-2H-[1,4'-bipyridin]-2-one of part B (4.6 g, 12.4 mmol), tributyl(1-ethoxyvinyl)tin (4.6 mL, 13.6 mmol) and $PdCl_2(PPh_3)_2$(87 mg, 0.12 mmol) in 1,4-dioxane (30 mL) was irradiated using a CEM Explorer™ microwave at 130° C. for 2 h. The resulting dark solution was filtered through Celite, rinsing with ethyl acetate. The filtrate was concentrated and the residue was dissolved into tetrahydrofuran (5 mL) and treated with concentrated HCl until hydrolysis was complete. The solution was concentrated in vacuo and purified using normal phase chromatography (ethyl acetate/heptane) to provide the acetyl compound as a yellow oil (3.3 g): MS (ES) m/e 379 (M+H).

Step D: Preparation of 2'-acetyl-3-chloro-4-hydroxy-5',6-dimethyl-2H-[1,4'-bipyridin]-2-one

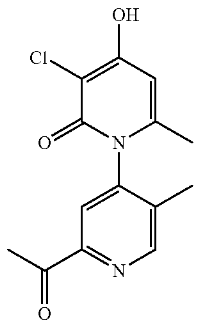 [SMILES: CC(=O)c1cc(-n2c(C)cc(O)c(Cl)c2=O)c(C)cn1]

To a solution of 2'-acetyl-4-((4-methoxybenzyl)oxy)-5',6-dimethyl-2H-[1,4'-bipyridin]-2-one of part C (3.3 g, 8.7 mmol) in 2-propanol (100 mL) was added N-chlorosuccinimide (1.27 g, 9.6 mmol) and 10 drops of dichloroacetic acid. The slurry was heated at 60° C. for 3 h. The resulting slurry was concentrated and the residue was partitioned between ethyl acetate and water. The organic layer was washed with water and brine and dried over magnesium sulfate. The solution was concentrated in vacuo. The residue was suspended into dichloromethane and the resulting white solid was collected by vacuum filtration to provide the chlorinated deprotected product (1.16 g): MS (ES) m/e 293 (M+H).

Step E: Preparation of 2'-acetyl-3-chloro-4-((3,5-difluoropyridin-2-yl)methoxy)-5',6-dimethyl-2H-[1,4'-bipyridin]-2-one

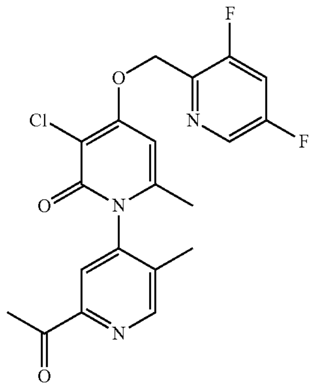 [SMILES: CC(=O)c1cc(-n2c(C)cc(OCc3ncc(F)cc3F)c(Cl)c2=O)c(C)cn1]

To a solution of 2'-acetyl-3-chloro-4-hydroxy-5',6-dimethyl-2H-[1,4'-bipyridin]-2-one of part D (500 mg, 1.7 mmol) in N,N-dimethylformamide (3 mL) was added 2-chloromethyl-3,5-difluoro-pyridine (277 mg, 1.7 mmol), potassium carbonate (590 mg, 4.28 mmol) and 18-crown-6 (10 mg) and the reaction was stirred at 60° C. for 4 h. After cooling the solution was partitioned between ethyl acetate and water. The organic layer was washed with water and brine and dried over magnesium sulfate. The solution was filtered and concentrated in vacuo. The crude material was purified using normal phase chromatography (ethyl acetate/heptane) to provide alkylated product as a yellow solid (397 mg): MS (ES) m/e 420 (M+H).

Step F: Preparation of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one

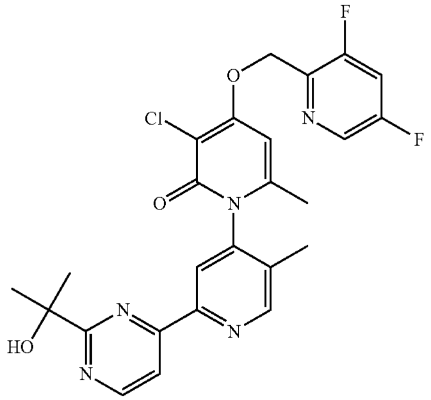 [SMILES: Cc1cnc(-c2ccnc(C(C)(C)O)n2)cc1-n1c(C)cc(OCc2ncc(F)cc2F)c(Cl)c1=O]

To a solution of 2'-acetyl-3-chloro-4-((3,5-difluoropyridin-2-yl)methoxy)-5',6-dimethyl-2H-[1,4'-bipyridin]-2-one from step E (397 mg, 0.95 mmol) in N,N-dimethylformamide (3 mL) was added N,N-dimethylformamide dimethyl acetal (0.18 mL, 1.42 mmol) and the solution was heated to 55° C. for 18 h. The solution was concentrated to half volume and 2-hydroxy-2-methylpropionamidine HCl (195 mg, 1.42 mmol) and potassium carbonate (393 mg, 2.85 mmol) were added. The slurry was heated at 75° C. for 18 h. The slurry was returned to ambient temperature and partitioned between ethyl acetate and water. The organic layer was washed with brine and dried over magnesium sulfate. The solution was concentrated and purified using normal phase chromatography (ethyl acetate/heptane) to provide the title compound as a light yellow solid (255 mg, 46%): MS (ES) m/e 514 (M+H).

Chiral resolution of 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

Racemic 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (250 mg, 0.49 mmol) was separated using supercritical fluid chromatography (Thar 80, preparative SFC, ChiralCel OD-H, 250×30 mmID column) with a mobile phase of carbon dioxide and ethanol. The separation method used an isocratic method of 40% ethanol with a flow rate of 50 mL/min and a cycle time of 10 min. Optical rotation was determined using a WZZ-2S polarimeter.

The faster isomer eluted at 1.77 minutes yielded 115 mg of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in ethylene glycol: $[\alpha]_D^{20}$−46° ($CH_3OH$); $^1H$ NMR (400 MHz, DMSO-$d_6$) δ ppm 8.97 (d, J=5.09 Hz, 1H), 8.86 (s, 1H), 8.69 (s, 1H), 8.61 (s, 1H), 8.24 (d, J=5.08 Hz, 1H), 8.10 (t, 1H), 6.85 (s, 1H), 5.50 (s, 2H), 5.26 (s, 1H), 2.11 (s, 3H), 1.98 (s, 3H), 1.54 (s, 3H), 1.52 (s, 3H); MS (ES) m/e 514 (M+H).

The slower isomer eluted at 3.68 minutes yielded 112 mg of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in ethylene glycol: $[\alpha]_D^{20}$+45° ($CH_3OH$); $^1H$ NMR (400 MHz, DMSO-$d_6$) δ ppm 8.97 (d, J=5.09 Hz, 1H), 8.86 (s, 1H), 8.69 (s, 1H), 8.61 (s, 1 H), 8.24 (d, J=5.08 Hz, 1H), 8.10 (t, 1H), 6.85 (s, 1H), 5.50 (s, 2H), 5.26 (s, 1H), 2.11 (s, 3H), 1.98 (s, 3H), 1.54 (s, 3H), 1.52 (s, 3H); MS (ES) m/e 514 (M+H).

Conformational interconversion of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in ethylene glycol.

In a 10 Lit 4-necked RBF equipped with a mechanical stirrer, thermometer pocket, reflux condenser and oil bath for heating, (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (40 g, 77.8 mmol) was suspended in ethylene glycol (4 L) at room temperature. The mixture was heated to 145-150° C. (internal temperature) and maintained for ~3h. The reaction mixture was allowed to cool to 80° C. and water (2.8 L) was added. The reaction mixture was cooled to RT (25-28° C.) and the precipitated solid was filtered and washed with water (1 L). It was suck dried well, air dried for 12 h and then dried under vacuum at 40° C. for 5 h to afford 30.5 g of mixture of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one and (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one. The aqueous portion was extracted with ethyl acetate (2×2 L). The combined extract was washed with water (2 L), dried over sodium sulfate and concentrated to yield mixture of product and ethylene glycol. It was stirred with water (500 mL) for 1 h, filtered and dried to yield another 3.5 g of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one. The crude product was 97.84% pure by LCMS analysis. Chiral HPLC analysis revealed a ratio of 53: 47 of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one: (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

Alternative procedure for the chiral resolution of 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

68 g of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one was submitted for SFC purification using the conditions described below; 27 g of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one and 32 g of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one was obtained. 32 g of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one recovered from this batch was racemized for two more cycles. At the end of three racemization cycles and three SFC purifications, 44.9 g of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one, 9g of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one and 4g-f (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one was obtained.

Preparative SFC Conditions:
Column/dimensions: Chiralcel OD-H (30×250 mm), 5μ
% CO2: 50.0%
% Co solvent: 50.0% (100% IPA)
Total Flow: 90.0g/min
Back Pressure: 100.0 bar
UV: 214 nm
Stack time: 13.5 min
Load/Inj: 240 mg
Solubility: 320 mL MeOH+ACN Conformational interconversion of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in NMP.

Figure 2:
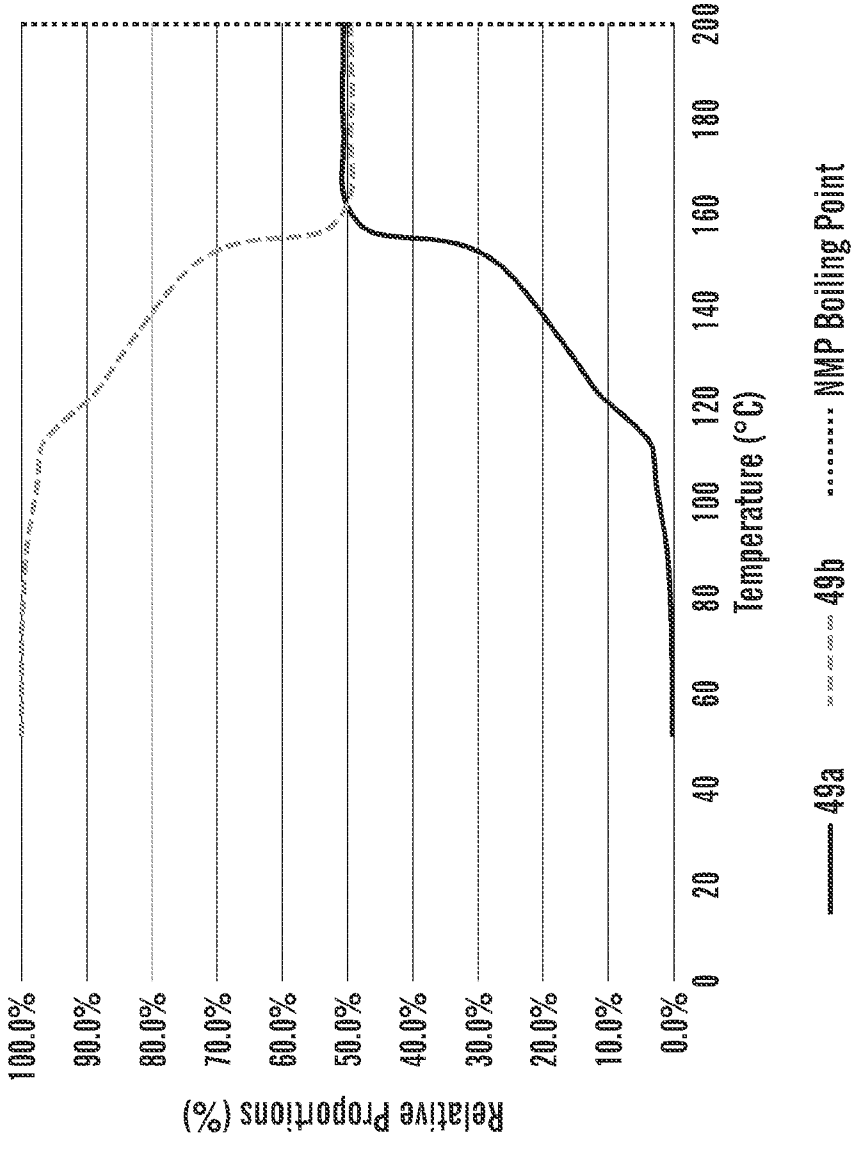
FIG. 2 illustrates that racemization of Compound 49b in NMP progresses relatively smoothly with Tonset≈114° C. and that racemization was complete ca. 40° C. below boiling point.

(+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (250.2 mg, 0.49 mmol) was dissolved in NMP (24 mL, Alfa Aesar, J29Z048) at room temperature. The mixture was ramped to reflux over 3 hours, periodically withdrawing 100 μL aliquots by vacuum. Each aliquot was diluted with Chromasolv ethanol (900 μL) and analyzed by chiral (Agilent LC 1100, Phenomenex Lux Cellulose-1, 4.6×100 mm, 5 μm 1.5 mL $min^{-1}$ flow rate) and non-chiral HPLC (Waters LC 2695, Waters XBridge C18, 4.6×150 mm, 3.5 μm, 35° C. column temperature, 1.0 mL $min^{-1}$ flow rate). Results are shown in FIG. 2.

Conformational interconversion of (+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in ethylene glycol.

Figure 3:
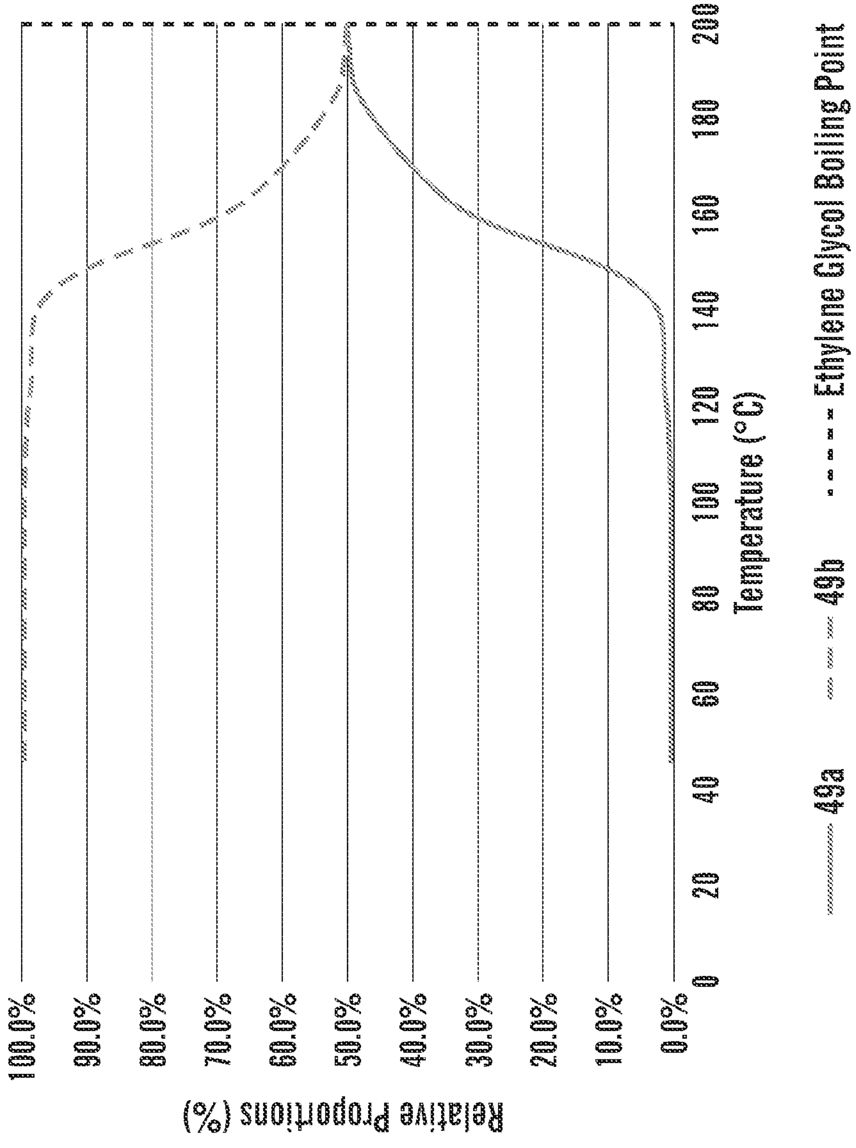
FIG. 3 illustrates that racemization of Compound 49b in ethylene glycol progresses relatively smoothly with Tonset≈138° C. and that racemization was complete before reflux is reached.

(+)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (250.2 mg, 0.49 mmol) was dispersed in ethylene glycol (25 mL, Beantown Chemical, 50009421) at room temperature. The mixture was ramped to reflux over 3 hours, periodically withdrawing 100 µL aliquots by vacuum. Each aliquot was diluted with Chromasolv ethanol (900 µL) and analyzed by chiral (Agilent LC 1100, Phenomenex Lux Cellulose-1, 4.6×100 mm, 5 µm 1.5 mL $min^{-1}$ flow rate) and non-chiral HPLC (Waters LC 2695, Waters XBridge C18, 4.6×150 mm, 3.5 µm, 35° C. column temperature, 1.0 mL $min^{-1}$ flow rate). Results are shown in FIG. 3.

Water induced precipitation of interconverted 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in ethylene glycol.

A solution of interconverted 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one in ethylene glycol (12.0 mL, 9.8 mg $mL^{-1}$) with pyridine (120 µL), was cooled from $T_{internal}$ 142° C. to 90° C. Water was added in ca. 1 mL portions to a total added volume of 9.02 mL (75.2% v/v based on starting solution). Precipitation was not observed during or following addition of any water. The solution was allowed to cool to room temperature and aged on standing over 96 hours. Crystallization began during cooling, $T_{nucleation}$≈75° C. The mother liquor was sampled, filtered through a 0.45 µm filter and an aliquot (100 µL) withdrawn, diluted with Chromasolv ethanol (900 µL) and analyzed by non-chiral HPLC (Waters LC 2695, Waters XBridge C18, 4.6×150 mm, 3.5 µm, 35° C. column temperature, 1.0 mL $min^{-1}$ flow rate). Relative proportion of precipitated product was calculated by comparison of the ratio of peak areas (pyridine: product) in sample to fully dissolved starting material. 84.2% of product dissolved initially was determined to have crystallized. Note, on prolonged standing, a small amount of additional crystallization was observed in the filtrate.

Chemical Purity of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one A summary of the impurities and related substances observed in drug substance batches is presented in Table 1. Batch 4, Batch 5, Batch 6, and Batch 7 are all clinical batches and have no impurities nor related substances at a level higher than that tested in the toxicology studies. Impurities <0.05% are not displayed in the table.

Some method differences exist between the methods used for Batch 1 (Toxicology) and the GMP batches. For Batch 1, purity is assessed using a development non-validated laboratory UPLC method and the chiral purity test uses SFC (%, area). These SFC chiral and UPLC purity test methods were routinely used for early development batches. For the GMP batches, impurities and related substances and chiral purity tests both utilize HPLC methods with phase appropriate method validation. Relative retention times (RRTs) presented in the Table 1 below are from the HPLC method unless otherwise noted.

TABLE 1

| Impurity/Related Substances | RRT | Batch 1 | Batch 2 | Batch 3 | Batch 4 | Batch 5 | *Batch 6 | *Batch 7 |
|---|---|---|---|---|---|---|---|---|
| | **RRT 0.53 | 0.26% | ND | ND | ND | ND | ND | ND |
| | RRT 0.92 | ND | ND | ND | ND | ND | 0.25% | 0.41% |
| | **RRT 0.96 | 0.30% | ND | ND | ND | ND | ND | ND |
| | **RRT 1.03 | 0.53% | ND | ND | ND | ND | ND | ND |
| | RRT 1.19 | ND | ND | ND | ND | ND | 0.26% | 0.41% |
| Total Impurities | | 0.68% | 0.05% | BRT | 0% | <LOQ | 0.51% | 0.84% |

N/A = Not Tested, only a reagent in the recycle batches
ND = Not Detected
LOQ = 0.03%
BRT = Below reporting threshold
* = Recycle batch manufacture process B
** = RRT from UPLC method Residual solvents specification was established in-line with ICHQ3C guidelines. A tabulated summary of the observed levels of the solvent levels in (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one is given below in Table 2.

TABLE 2

| Solvents | Acceptance Criteria (ppm) | Result in Batch 4 | Result in Batch 5 | Result in Batch 6 | Result in Batch 7 |
|---|---|---|---|---|---|
| Methanol | Not more than 3000 ppm | 101 ppm | ND | ND | 49 |

TABLE 2-continued

| Solvents | Acceptance Criteria (ppm) | Result in Batch 4 | Result in Batch 5 | Result in Batch 6 | Result in Batch 7 |
|---|---|---|---|---|---|
| Isopropyl alcohol | Not more than 5000 ppm | 1417 ppm | 1202 | 1228 | 1150 |
| Dichloromethane | Not more than 600 ppm | 394 ppm | ND | ND | 153 |
| Methyl tertiary butyl ether | Not more than 5000 ppm | 6 ppm | ND | ND | ND |
| Hexanes | Not more than 290 ppm | ND | ND | ND | ND |
| Ethyl acetate | Not more than 5000 ppm | ND | ND | ND | ND |
| 1,4-Dioxane | Not more than 380 ppm | ND | ND | ND | ND |
| Dimethyl formamide | Not more than 880 ppm | ND | ND | ND | ND |
| Glycerol | Not more than 5000 ppm | N/A | ND | ND | ND |

N/A = Not Tested, only a reagent in the recycle batches
ND = Not Detected

Inorganic Impurities: Potential inorganic impurities include heavy metals, palladium from coupling reaction catalysts used in the chemical synthesis, and drying and filtering agents utilized in the manufacturing process. Heavy metals are controlled by the use of standard manufacturing equipment in the manufacturing process and the heavy metals test included in the drug substance specification. Palladium carry-over in the drug substance manufacturing process is controlled during the multiple isolation procedures within the manufacturing process. The proposed palladium specification (not more than 50 ppm) is based on the permissible daily exposure for orally administered drug products as recommended in the USP chapter on limits for elemental impurities. Drying and filtering agent carry-over is controlled by subsequent filtration steps to remove the agents and the residue on ignition test included in the drug substance specification. Data presented in Table 3 confirm that all potential inorganic impurities are well controlled and below the specified limit.

TABLE 3

| Test | | Proposed Drug Substance Limit | Batch 19 Results | Batch 20 Results | Batch 21 Results | Batch 22 Results |
|---|---|---|---|---|---|---|
| Elemental Impurities by ICP-MS | Cd | Not more than 0.5 ppm | ND | ND | ND | ND |
| | Pb | Not more than 0.5 ppm | ND | ND | ND | ND |
| | As | Not more than 1.5 ppm | ND | ND | ND | BLQ |
| | Hg | Not more than 3 ppm | ND | BLQ | ND | ND |
| | Co | Not more than 5 ppm | ND | ND | ND | ND |
| | V | Not more than 10 ppm | ND | ND | ND | ND |
| | Ni | Not more than 20 ppm | ND | ND | ND | ND |
| | Li | Not more than 55 ppm | ND | ND | ND | ND |
| | Sn | Not more than 600 ppm | ND | ND | ND | ND |
| | Pd | Not more than 50 ppm | ND | ND | ND | ND |
| | Cu | Not more than 300 ppm | ND | ND | ND | ND |
| Residue on ignition | | NMT 0.5% w/w | 0.18% | 0.07% | 0.08% | 0.10% |

ND = Not Detected

BLQ = Below Level of Quantitation

Compound No. 65, Example B: Preparation of 3-chloro-4-((5-fluoropyrimidin-4-yl)methoxy)-2'-(2-(2-hydroxypropan-2-yl)pyrimidin-4-yl)-5',6-dimethyl-2H-[1,4'-bipyridin]-2-one.

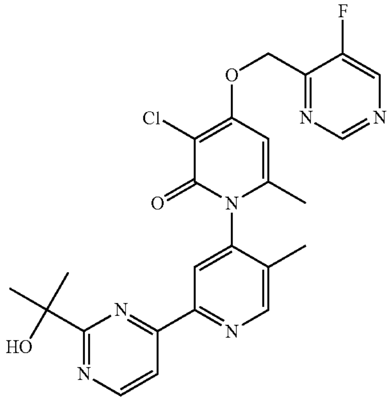 [SMILES: Cc1cnc(-c2ccnc(C(C)(C)O)n2)cc1-n1c(C)cc(OCc2ncncc2F)c(Cl)c1=O]

The title compound was prepared following Compound 49, Example A, up to Step E, but alkylating 3-chloro-4-hydroxy-2'-(2-(2-hydroxypropan-2-yl)pyrimidin-4-yl)-5',6-dimethyl-2H-[1,4'-bipyridin]-2-one with 4-(chloromethyl)-5-fluoropyrimidine instead of 2-(chloromethyl)-3,5-difluoropyridine to give the desired benzyl ether. The title compound was prepared following the general procedure of Compound 49, Example A, Step F.

Example 2: Single Crystal Structure Determination

Sample Preparation for determination of x-ray crystal structure for (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

In a 10 mL scintillation vial, 100 mg (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Lot 6, GVK Bio, Hyderabad, India) was dissolved in 1 mL of anhydrous acetonitrile (Sigma-Aldrich) with moderate warming. The vial was sealed with Parafilm® and the cap loosely tightened. X-ray quality crystals were obtained after approximately four days and were then transported to the University of Toledo Instrumentation Center for data collection.

X-ray Structure Determination of (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

Crystals of an appropriate size were obtained by slow evaporation of acetonitrile at room temperature. A single, needle-like crystal was mounted on a MiTeGen™ cryo-loop with the central axis of the needle off-set to the axis of rotation. Preliminary analysis and data collection were performed at a temperature of 100 K using Copper Kα radiation (1.54184 Å) with a Bruker-Nonius Kappa APEX II Duo™ diffractometer equipped with an IμS Cu source and an Oxford Cryostream™ low temperature device.

The total exposure time for data collection was 67.77 hours. The frames were integrated with the Bruker SAINT software package (Reference: Bruker Analytical X-Ray, Madison, WI, 2015) using a narrow-frame algorithm. The integration of the data using a triclinic unit cell yielded a total of 11397 reflections to a maximum θ angle of 66.980 (0.84 Å resolution), of which 11397 were independent (average redundancy 1.000, completeness=99.4%, Rint=4.58%, Rsig=4.38%) and 9621 (84.42%) were greater than 2σ(F2). The final cell constants of a=7.8581(16) Å, b=9.7289(19) Å, c=17.619(4) A, a=79.27(3)°, R=81.35(3)°, γ=69.05(3)°, volume=1230.8(5) A3, are based upon the refinement of the XYZ-centroids of 8394 reflections above 20 σ(I) with 10.26°<2θ<136.1°. Data were corrected for absorption effects using the Multi-Scan method (SADABS) (Reference: Bruker Analytical X-Ray, Madison, WI, 2014). The ratio of minimum to maximum apparent transmission was 0.881.

The structure was determined and refined using the Bruker SHELXTL Software Package (Reference: Sheldrick, G. M. (2008). Acta Cryst. A64, 112-122)., using the space group P 1, with Z=2 for the formula unit, C25.25H22.38ClF2N5.12O3. The final anisotropic full-matrix least-squares refinement on F2 with 836 variables converged at $R^1$=4.90%, for the observed data and wR2=13.21% for all data. The goodness-of-fit was 1.048. The largest peak in the final difference electron density synthesis was 0.354 e−/Å3 and the largest hole was −0.227 e−/Å3 with an RMS deviation of 0.051 e−/Å3. On the basis of the final model, the calculated density was 1.401 g/cm3 and F(000), 538 e−.

The unit cell contains two crystallographically independent molecules of $C_{25}H_{22}N5O_3F_2Cl$ and 0.25 molecules of acetonitrile. All crystals evaluated were twinned by 180° rotation around the a-axis. The crystal showed a twin ratio of 0.75:0.25. Both $C_{25}H_{22}N5O_3F_2Cl$ molecules show the same rotamer. However, one of them is slightly disordered in the ring-$C(CH_3)_2(OH)$ area. The ratio of the two different orientations is approximately 85:15. The OH-hydrogen atom of the lesser part was not included in the refinement. Full matrix least-squares refinements were carried out by minimizing $w(Fo^2\text{-}FC^2)^2$. The non-hydrogen atoms were refined anisotropically to convergence. Hydrogen atoms with full occupancy were located from difference-Fourier-syntheses and refined, while the hydrogen atoms on the disordered parts and the acetonitrile molecule were calculated on idealized positions and treated using an appropriate riding model as well as atomic displacement parameters constrained to the ones of the bonding atom. The final residual values and structure refinement parameters are listed in Tables 4 and 5.

Complete listings of positional and isotropic displacement coefficients for hydrogen atoms, anisotropic displacement coefficients for the non-hydrogen atoms are listed in Tables 6-10.

TABLE 4

Sample and crystal data for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridinl-2-one

| | | |
|---|---|---|
| Chemical formula | 2 $C_{25}H_{22}ClF_2N_5O_3$•0.25 $CH_3CN$ | |
| Formula weight | 519.06 g/mol | |
| Temperature | 120(2) K | |
| Wavelength | 1.54184 Å | |
| Crystal system | triclinic | |
| Space group | P 1 | |
| Unit cell dimensions | a = 7.8581(16) Å | α = 79.27(3)° |
| | b = 9.7289(19) Å | β = 81.35(3)° |
| | c= 17.619(4) Å | γ = 69.05(3)° |
| Volume | 1230.8(5) $Å^3$ | |
| Z | 2 | |
| Density (calculated) | 1.401 g/$cm^3$ | |
| Absorption coefficient | 1.839 $mm^{-1}$ | |
| F(000) | 538 | |

TABLE 5

| Data collection and structure refinement for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one | |
|---|---|
| Theta range for data collection | 2.56 to 66.98° |
| Index ranges | −9 <= h <= 9, −11 <= k <= 11, −20 <= l <= 20 |
| Reflections collected | 11397 |
| Independent reflections | 11397 [R(int) = 0.0458] |
| Coverage of independent reflections | 99.4% |
| Absorption correction | Multi-Scan |
| Structure solution technique | direct methods |
| Structure solution program | XT, VERSION 2014/4 |
| Refinement method | Full-matrix least-squares on $F^2$ |
| Refinement program | SHELXL-2014/7 (Sheldrick, 2014) |
| Function minimized | $\Sigma w(F_o^2 - F_c^2)^2$ |
| Data/restraints/parameters | 11397/15/836 |
| Goodness-of-fit on $F^2$ | 1.048 |
| Final R indices | 9621 data; I > 2σ(I) R1 = 0.0490, wR2 = 0.1223<br>all data R1 = 0.0612, wR2 = 0.1321 |
| Weighting scheme | $w = 1/[\sigma^2(F_o^2) + (0.0770P)^2 + 0.1692P]$<br>where $P = (F_o^2 + 2F_c^2)/3$ |
| Absolute structure parameter | 0.0(0) |
| Largest diff. peak and hole | 0.354 and −0.227 eÅ$^{-3}$ |
| R.M.S. deviation from mean | 0.051 eÅ$^{-3}$ |

TABLE 6

Atomic coordinates and equivalent isotropic atomic displacement parameters (Å$^2$) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one

| | x/a | y/b | z/c | U(eq) |
|---|---|---|---|---|
| Cl1 | 0.53120(17) | 0.71536(16) | 0.92483(8) | 0.0322(3) |
| Cl2 | 0.17506(18) | 0.28468(16) | 0.08423(8) | 0.0338(3) |
| O1 | 0.4095(5) | 0.7004(5) | 0.0943(2) | 0.0306(9) |
| O2 | 0.2520(5) | 0.6773(4) | 0.8512(2) | 0.0243(8) |
| O4 | 0.1733(5) | 0.3053(5) | 0.9138(2) | 0.0294(9) |
| O5 | 0.8084(5) | 0.3203(4) | 0.1496(2) | 0.0263(8) |
| O6 | 0.4837(7) | 0.1003(6) | 0.6102(3) | 0.0521(14) |
| N1 | 0.1314(6) | 0.6803(5) | 0.0857(3) | 0.0220(10) |
| N2 | 0.0211(7) | 0.6677(6) | 0.3284(3) | 0.0297(11) |
| N5 | 0.1984(8) | 0.7704(6) | 0.6804(3) | 0.0385(12) |
| N6 | 0.8760(6) | 0.3206(5) | 0.9145(3) | 0.0218(10) |
| N7 | 0.9898(7) | 0.3361(5) | 0.6716(3) | 0.0318(11) |
| N8 | 0.7582(6) | 0.7280(5) | 0.6782(3) | 0.0271(10) |
| N9 | 0.7137(8) | 0.8613(6) | 0.5505(3) | 0.0409(13) |
| N10 | 0.6994(7) | 0.2281(6) | 0.3198(3) | 0.0366(12) |
| F1 | 0.3380(5) | 0.3795(4) | 0.7461(2) | 0.0422(9) |
| F2 | 0.4226(8) | 0.6442(6) | 0.5016(2) | 0.0714(15) |
| F3 | 0.7584(7) | 0.3363(6) | 0.4949(2) | 0.0624(13) |
| F4 | 0.6074(7) | 0.6166(4) | 0.2522(2) | 0.0565(12) |
| C1 | 0.3301(7) | 0.6941(6) | 0.9703(3) | 0.0235(11) |
| C2 | 0.3015(7) | 0.6925(6) | 0.0525(3) | 0.0234(11) |
| C3 | 0.0017(8) | 0.6711(6) | 0.0439(3) | 0.0240(12) |
| C4 | 0.0394(8) | 0.6690(6) | 0.9660(3) | 0.0234(12) |
| C5 | 0.2052(7) | 0.6783(6) | 0.9285(3) | 0.0209(11) |
| C6 | 0.8262(9) | 0.6644(8) | 0.0875(4) | 0.0294(13) |
| C7 | 0.0971(7) | 0.6774(6) | 0.1687(3) | 0.0223(11) |
| C8 | 0.0062(8) | 0.8088(6) | 0.1997(3) | 0.0283(12) |
| C9 | 0.9683(9) | 0.7950(7) | 0.2798(4) | 0.0325(13) |
| C10 | 0.1159(7) | 0.5428(6) | 0.2965(3) | 0.0254(12) |
| C11 | 0.1527(7) | 0.5437(6) | 0.2170(3) | 0.0217(11) |
| C12 | 0.9544(10) | 0.9585(7) | 0.1498(4) | 0.0402(15) |
| C13 | 0.1840(8) | 0.4042(7) | 0.3514(3) | 0.0275(12) |
| C14 | 0.1852(9) | 0.4088(8) | 0.4299(3) | 0.0372(15) |
| C15 | 0.2469(10) | 0.2758(9) | 0.4771(4) | 0.0473(19) |
| N3 | 0.2465(7) | 0.2752(6) | 0.3229(3) | 0.0322(11) |
| N4 | 0.3125(8) | 0.1453(7) | 0.4495(3) | 0.0464(15) |
| O3A | 0.5322(8) | 0.9019(6) | 0.3873(4) | 0.0395(14) |
| C16A | 0.3178(14) | 0.1511(9) | 0.3716(5) | 0.0287(19) |
| C17A | 0.3882(13) | 0.0014(8) | 0.3422(4) | 0.0324(16) |
| C18A | 0.2302(13) | 0.9396(11) | 0.3536(8) | 0.062(3) |
| C19A | 0.4688(12) | 0.0108(8) | 0.2587(4) | 0.0400(18) |
| O3B | 0.232(7) | 0.046(5) | 0.272(3) | 0.077(12) |

TABLE 6-continued

Atomic coordinates and equivalent isotropic atomic displacement parameters (Å$^2$) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one

| | x/a | y/b | z/c | U(eq) |
|---|---|---|---|---|
| C16B | 0.250(7) | 0.161(6) | 0.380(3) | 0.023(13) |
| C17B | 0.289(7) | 0.013(5) | 0.351(3) | 0.033(10) |
| C18B | 0.160(10) | 0.936(8) | 0.395(4) | 0.064(17) |
| C19B | 0.492(8) | 0.925(9) | 0.357(4) | 0.06(2) |
| C20 | 0.1324(8) | 0.6450(7) | 0.8074(3) | 0.0269(12) |
| C21 | 0.2203(8) | 0.6407(6) | 0.7258(3) | 0.0273(12) |
| C22 | 0.3147(8) | 0.5078(7) | 0.6980(3) | 0.0308(13) |
| C23 | 0.3865(10) | 0.5039(8) | 0.6222(4) | 0.0399(16) |
| C24 | 0.3606(10) | 0.6374(8) | 0.5774(4) | 0.0462(17) |
| C25 | 0.2701(11) | 0.7701(8) | 0.6065(4) | 0.0463(18) |
| C26 | 0.9924(8) | 0.3054(6) | 0.0346(3) | 0.0247(11) |
| C27 | 0.0268(8) | 0.3098(6) | 0.9518(3) | 0.0238(12) |
| C28 | 0.7072(8) | 0.3273(6) | 0.9520(3) | 0.0252(12) |
| C29 | 0.6802(9) | 0.3295(7) | 0.0302(4) | 0.0262(13) |
| C30 | 0.8232(8) | 0.3199(6) | 0.0719(3) | 0.0238(12) |
| C31 | 0.5633(9) | 0.3325(9) | 0.9045(4) | 0.0362(15) |
| C32 | 0.9106(7) | 0.3243(6) | 0.8307(3) | 0.0217(11) |
| C33 | 0.0091(8) | 0.1938(6) | 0.8004(3) | 0.0294(13) |
| C34 | 0.0448(9) | 0.2090(7) | 0.7194(4) | 0.0348(14) |
| C35 | 0.8914(7) | 0.4595(6) | 0.7034(3) | 0.0247(11) |
| C36 | 0.8501(7) | 0.4584(6) | 0.7827(3) | 0.0241(11) |
| C37 | 0.0790(12) | 0.0461(7) | 0.8497(4) | 0.0454(18) |
| C38 | 0.8323(7) | 0.5989(6) | 0.6482(3) | 0.0264(12) |
| C39 | 0.8509(9) | 0.5982(8) | 0.5687(4) | 0.0355(14) |
| C40 | 0.7904(9) | 0.7320(8) | 0.5218(3) | 0.0422(17) |
| C41 | 0.7012(8) | 0.8517(7) | 0.6279(3) | 0.0300(13) |
| C42 | 0.6153(9) | 0.9994(7) | 0.6604(3) | 0.0344(14) |
| C43 | 0.5182(12) | 0.9802(8) | 0.7391(4) | 0.0464(19) |
| C44 | 0.7654(12) | 0.0647(9) | 0.6620(6) | 0.062(2) |
| C45 | 0.6279(8) | 0.3605(7) | 0.1908(4) | 0.0314(13) |
| C46 | 0.6584(8) | 0.3588(7) | 0.2735(3) | 0.0308(12) |
| C47 | 0.6501(9) | 0.4861(7) | 0.3001(4) | 0.0386(15) |
| C48 | 0.6826(11) | 0.4846(9) | 0.3755(4) | 0.0476(18) |
| C49 | 0.7241(10) | 0.3486(9) | 0.4207(4) | 0.0439(16) |
| C50 | 0.7307(10) | 0.2237(8) | 0.3929(4) | 0.0426(16) |
| N11 | 0.754(5) | 0.959(4) | 0.896(2) | 0.085(10) |
| C51 | 0.641(5) | 0.985(4) | 0.949(2) | 0.062(8) |
| C52 | 0.521(4) | 0.006(3) | 0.0100(16) | 0.045(6) |

U(eq) is defined as one third of the trace of the orthogonalized Uy tensor.

TABLE 7

Bond lengths (Å) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

| | | | |
|---|---|---|---|
| Cl1-C1 | 1.724(5) | CL2-C26 | 1.724(5) |
| O1-C2 | 1.235(7) | O2-C5 | 1.357(6) |
| O2-C20 | 1.449(7) | O4-C27 | 1.232(7) |
| O5-C30 | 1.357(7) | O5-C45 | 1.446(7) |
| O6-C42 | 1.429(7) | O6-H6O | 0.91(9) |
| N1-C3 | 1.380(7) | N1-C2 | 1.412(7) |
| N1-C7 | 1.444(7) | N2-C9 | 1.335(8) |
| N2-C10 | 1.353(7) | N5-C21 | 1.331(8) |
| N5-C25 | 1.340(8) | N6-C28 | 1.376(8) |
| N6-C27 | 1.403(7) | N6-C32 | 1.456(7) |
| N7-C34 | 1.329(8) | N7-C35 | 1.345(7) |
| N8-C41 | 1.331(7) | N8-C38 | 1.351(7) |
| N9-C41 | 1.340(7) | N9-C40 | 1.343(9) |
| N10-C46 | 1.336(8) | N10-C50 | 1.337(8) |
| F1-C22 | 1.343(7) | F2-C24 | 1.348(7) |
| F3-C49 | 1.350(8) | F4-C47 | 1.349(8) |
| C1-C5 | 1.378(7) | C1-C2 | 1.431(7) |
| C3-C4 | 1.362(8) | C3-C6 | 1.491(9) |
| C4-C5 | 1.395(8) | C4-H4 | 0.99(6) |
| C6-H6A | 1.08(9) | C6-H6B | 0.97(7) |
| C6-H6C | 0.96(7) | C7-C11 | 1.378(8) |
| C7-C8 | 1.389(8) | C8-C9 | 1.390(8) |
| C8-C12 | 1.506(9) | C9-H9 | 0.88(7) |
| C10-C11 | 1.385(8) | C10-C13 | 1.481(8) |
| C11-H11 | 0.95(6) | C12-H12A | 1.06(5) |
| C12-H12B | 1.06(5) | C12-H12C | 1.06(5) |
| C13-N3 | 1.338(8) | C13-C14 | 1.393(8) |
| C14-C15 | 1.369(9) | C14-H14 | 0.94(7) |
| C15-N4 | 1.342(10) | C15-H15 | 0.95(8) |
| N3-C16A | 1.335(9) | N3-C16B | 1.35(5) |
| N4-C16B | 1.35(5) | N4-C16A | 1.357(10) |
| O3A-C17A | 1.431(9) | O3A-H3A | 0.82 |
| C16A-C17A | 1.521(12) | C17A-C19A | 1.513(10) |
| C17A-C18A | 1.536(12) | C18A-H18A | 0.96 |
| C18A-H18B | 0.96 | C18A-H18C | 0.96 |
| C19A-H19A | 0.96 | C19A-H19B | 0.96 |
| C19A-H19C | 0.96 | O3B-C17B | 1.48(6) |
| C16B-C17B | 1.53(7) | C17B-C18B | 1.51(3) |
| C17B-C19B | 1.52(3) | C18B-H18D | 0.96 |
| C18B-H18E | 0.96 | C18B-H18F | 0.96 |
| C19B-H19D | 0.96 | C19B-H19E | 0.96 |
| C19B-H19F | 0.96 | C20-C21 | 1.500(8) |
| C20-H20A | 1.00(6) | C20-H20B | 0.92(7) |
| C21-C22 | 1.379(8) | C22-C23 | 1.370(9) |
| C23-C24 | 1.354(11) | C23-H23 | 0.82(8) |
| C24-C25 | 1.383(10) | C25-H25 | 1.01(7) |
| C26-C30 | 1.362(8) | C26-C27 | 1.438(8) |
| C28-C29 | 1.365(9) | C28-C31 | 1.486(8) |
| C29-C30 | 1.399(8) | C29-H29 | 0.77(7) |
| C31-H31A | 0.97(10) | C31-H31B | 1.00(7) |
| C31-H31C | 0.88(7) | C32-C36 | 1.382(8) |
| C32-C33 | 1.386(8) | C33-C34 | 1.403(8) |
| C33-C37 | 1.495(8) | C34-H34 | 0.91(7) |
| C35-C36 | 1.385(8) | C35-C38 | 1.481(8) |
| C36-H36 | 0.92(6) | C37-H37A | 0.88(13) |
| C37-H37B | 1.10(9) | C37-H37C | 0.95(9) |
| C38-C39 | 1.388(8) | C39-C40 | 1.370(9) |
| C39-H39 | 0.91(9) | C40-H40 | 0.99(6) |
| C41-C42 | 1.532(8) | C42-C43 | 1.492(9) |
| C42-C44 | 1.533(11) | C43-H43A | 1.02(10) |
| C43-H43B | 0.99(9) | C43-H43C | 0.98(8) |
| C44-H44A | 1.08(5) | C44-H44B | 1.07(5) |
| C44-H44C | 1.07(5) | C45-C46 | 1.507(8) |
| C45-H45A | 0.94(6) | C45-H45B | 1.02(6) |
| C46-C47 | 1.381(9) | C47-C48 | 1.386(10) |
| C48-C49 | 1.367(11) | C48-H47 | 0.98(11) |
| C49-C50 | 1.374(11) | C50-H50 | 0.98(10) |
| N11-C51 | 1.18(5) | C51-C52 | 1.31(5) |
| C52-H52A | 0.96 | C52-H52B | 0.96 |
| C52-H52C | 0.96 | | |

TABLE 8

Bond angles (°) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

| | | | |
|---|---|---|---|
| C5-O2-C20 | 117.3(4) | C30-O5-C45 | 118.6(4) |
| C42-O6-H6O | 108.(5) | C3-N1-C2 | 124.1(5) |
| C3-N1-C7 | 120.0(5) | C2-N1-C7 | 115.9(4) |
| C9-N2-C10 | 116.9(5) | C21-N5-C25 | 118.7(6) |
| C28-N6-C27 | 124.2(5) | C28-N6-C32 | 121.2(5) |
| C27-N6-C32 | 114.6(5) | C34-N7-C35 | 117.4(5) |
| C41-N8-C38 | 116.6(5) | C41-N9-C40 | 115.9(5) |
| C46-N10-C50 | 118.4(6) | C5-C1-C2 | 122.3(5) |
| C5-C1-C11 | 120.8(4) | C2-C1-C11 | 116.9(4) |
| O1-C2-N1 | 119.9(5) | O1-C2-C1 | 126.1(5) |
| N1-C2-C1 | 114.0(5) | C4-C3-N1 | 119.0(5) |
| C4-C3-C6 | 123.6(5) | N1-C3-C6 | 117.4(5) |
| C3-C4-C5 | 120.8(5) | C3-C4-H4 | 114.(3) |
| C5-C4-H4 | 125.(3) | O2-C5-C1 | 116.3(5) |
| O2-C5-C4 | 124.1(5) | C1-C5-C4 | 119.6(5) |
| C3-C6-H6A | 110.(5) | C3-C6-H6B | 109.(4) |
| H6A-C6-H6B | 111.(6) | C3-C6-H6C | 110.(4) |
| H6A-C6-H6C | 106.(6) | H6B-C6-H6C | 111.(5) |
| C11-C7-C8 | 120.2(5) | C11-C7-N1 | 119.8(5) |
| C8-C7-N1 | 120.0(5) | C7-C8-C9 | 116.3(5) |
| C7-C8-C12 | 122.3(5) | C9-C8-C12 | 121.4(5) |
| N2-C9-C8 | 125.1(5) | N2-C9-H9 | 116.(4) |
| C8-C9-H9 | 119.(4) | N2-C10-C11 | 122.4(5) |
| N2-C10-C13 | 116.3(5) | C11-C10-C13 | 121.3(5) |
| C7-C11-C10 | 119.0(5) | C7-C11-H11 | 121.(3) |
| C10-C11-H11 | 120.(3) | C8-C12-H12A | 115.(4) |
| C8-C12-H12B | 115.(4) | H12A-C12-H12B | 91.(6) |
| C8-C12-H12C | 113.(5) | H12A-C12-H12C | 96.(6) |
| H12B-C12-H12C | 121.(7) | N3-C13-C14 | 121.3(5) |
| N3-C13-C10 | 117.8(5) | C14-C13-C10 | 120.9(6) |
| C15-C14-C13 | 117.4(6) | C15-C14-H14 | 122.(4) |
| C13-C14-H14 | 120.(4) | N4-C15-C14 | 122.1(6) |
| N4-C15-H15 | 120.(5) | C14-C15-H15 | 118.(5) |
| C16A-N3-C13 | 117.6(6) | C13-N3-C16B | 111.(2) |
| C15-N4-C16B | 110.(2) | C15-N4-C16A | 116.7(6) |
| C17A-O3A-H3A | 109.5 | N3-C16A-N4 | 124.4(7) |
| N3-C16A-C17A | 119.6(7) | N4-C16A-C17A | 115.5(6) |
| O3A-C17A-C19A | 106.6(7) | O3A-C17A-C16A | 108.8(6) |
| C19A-C17A-C16A | 112.7(6) | O3A-C17A-C18A | 109.0(6) |
| C19A-C17A-C18A | 111.5(8) | C16A-C17A-C18A | 108.2(8) |
| C17A-C18A-H18A | 109.5 | C17A-C18A-H18B | 109.5 |
| H18A-C18A-H18B | 109.5 | C17A-C18A-H18C | 109.5 |
| H18A-C18A-H18C | 109.5 | H18B-C18A-H18C | 109.5 |
| C17A-C19A-H19A | 109.5 | C17A-C19A-H19B | 109.5 |
| H19A-C19A-H19B | 109.5 | C17A-C19A-H19C | 109.5 |
| H19A-C19A-H19C | 109.5 | H19B-C19A-H19C | 109.5 |
| N4-C16B-N3 | 124.(4) | N4-C16B-C17B | 113.(4) |
| N3-C16B-C17B | 114.(4) | O3B-C17B-C18B | 102.(5) |
| O3B-C17B-C19B | 114.(5) | C18B-C17B-C19B | 115.(5) |
| O3B-C17B-C16B | 108.(4) | C18B-C17B-C16B | 110.(4) |
| C19B-C17B-C16B | 107.(5) | C17B-C18B-H18D | 109.5 |
| C17B-C18B-H18E | 109.5 | H18D-C18B-H18E | 109.5 |
| C17B-C18B-H18F | 109.5 | H18D-C18B-H18F | 109.5 |
| H18E-C18B-H18F | 109.5 | C17B-C19B-H19D | 109.5 |
| C17B-C19B-H19E | 109.5 | H19D-C19B-H19E | 109.5 |
| C17B-C19B-H19F | 109.5 | H19D-C19B-H19F | 109.5 |
| H19E-C19B-H19F | 109.5 | O2-C20-C21 | 106.7(5) |
| O2-C20-H20A | 104.(4) | C21-C20-H20A | 110.(3) |
| O2-C20-H20B | 109.(4) | C21-C20-H20B | 108.(4) |
| H20A-C20-H20B | 119.(6) | N5-C21-C22 | 121.3(5) |
| N5-C21-C20 | 117.3(5) | C22-C21-C20 | 121.4(5) |
| F1-C22-C23 | 119.1(6) | F1-C22-C21 | 119.4(5) |
| C23-C22-C21 | 121.4(6) | C24-C23-C22 | 115.9(6) |
| C24-C23-H23 | 119.(6) | C22-C23-H23 | 125.(6) |
| F2-C24-C23 | 120.0(6) | F2-C24-C25 | 117.9(6) |
| C23-C24-C25 | 122.1(6) | N5-C25-C24 | 120.6(6) |
| N5-C25-H25 | 118.(4) | C24-C25-H25 | 121.(4) |
| C30-C26-C27 | 121.8(5) | C30-C26-C12 | 121.5(4) |
| C27-C26-C12 | 116.6(4) | O4-C27-N6 | 120.1(5) |
| O4-C27-C26 | 125.4(5) | N6-C27-C26 | 114.5(5) |
| C29-C28-N6 | 118.7(5) | C29-C28-C31 | 123.6(6) |
| N6-C28-C31 | 117.7(6) | C28-C29-C30 | 120.7(6) |
| C28-C29-H29 | 115.(4) | C30-C29-H29 | 124.(5) |
| O5-C30-C26 | 115.6(5) | O5-C30-C29 | 124.5(5) |
| C26-C30-C29 | 119.9(5) | C28-C31-H31A | 110.(5) |
| C28-C31-H31B | 116.(4) | H31A-C31-H31B | 110.(6) |

TABLE 8-continued

Bond angles (°) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

| | | | |
|---|---|---|---|
| C28-C31-H31C | 113.(4) | H31A-C31-H31C | 106.(7) |
| H31B-C31-H31C | 101.(6) | C36-C32-C33 | 120.9(5) |
| C36-C32-N6 | 119.6(5) | C33-C32-N6 | 119.4(5) |
| C32-C33-C34 | 115.6(5) | C32-C33-C37 | 123.1(5) |
| C34-C33-C37 | 121.3(6) | N7-C34-C33 | 125.1(5) |
| N7-C34-H34 | 120.(4) | C33-C34-H34 | 115.(4) |
| N7-C35-C36 | 122.6(5) | N7-C35-C38 | 115.8(5) |
| C36-C35-C38 | 121.5(5) | C32-C36-C35 | 118.4(5) |
| C32-C36-H36 | 118.(4) | C35-C36-H36 | 123.(4) |
| C33-C37-H37A | 115.(8) | C33-C37-H37B | 112.(4) |
| H37A-C37-H37B | 96.(9) | C33-C37-H37C | 108.(5) |
| H37A-C37-H37C | 121.(9) | H37B-C37-H37C | 104.(7) |
| N8-C38-C39 | 120.8(5) | N8-C38-C35 | 117.5(5) |
| C39-C38-C35 | 121.7(5) | C40-C39-C38 | 117.9(6) |
| C40-C39-H39 | 119.(5) | C38-C39-H39 | 119.(5) |
| N9-C40-C39 | 122.2(5) | N9-C40-H40 | 117.(4) |
| C39-C40-H40 | 121.(4) | N8-C41-N9 | 126.6(6) |
| N8-C41-C42 | 117.6(5) | N9-C41-C42 | 115.8(5) |
| O6-C42-C43 | 107.8(6) | O6-C42-C41 | 108.7(5) |
| C43-C42-C41 | 111.6(5) | O6-C42-C44 | 108.7(6) |
| C43-C42-C44 | 111.2(7) | C41-C42-C44 | 108.9(6) |
| C42-C43-H43A | 114.(5) | C42-C43-H43B | 111.(5) |
| H43A-C43-H43B | 106.(7) | C42-C43-H43C | 112.(5) |
| H43A-C43-H43C | 105.(7) | H43B-C43-H43C | 109.(7) |
| C42-C44-H44A | 112.(6) | C42-C44-H44B | 109.(5) |
| H44A-C44-H44B | 96.(8) | C42-C44-H44C | 102.(5) |
| H44A-C44-H44C | 129.(8) | H44B-C44-H44C | 108.(7) |
| O5-C45-C46 | 105.2(5) | O5-C45-H45A | 111.(4) |
| C46-C45-H45A | 112.(4) | O5-C45-H45B | 106.(3) |
| C46-C45-H45B | 113.(3) | H45A-C45-H45B | 109.(5) |
| N10-C46-C47 | 120.9(5) | N10-C46-C45 | 117.5(5) |
| C47-C46-C45 | 121.6(6) | F4-C47-C46 | 119.6(6) |
| F4-C47-C48 | 118.4(6) | C46-C47-C48 | 121.9(6) |
| C49-C48-C47 | 115.1(7) | C49-C48-H47 | 122.(6) |
| C47-C48-H47 | 123.(6) | F3-C49-C48 | 119.3(7) |
| F3-C49-C50 | 118.9(6) | C48-C49-C50 | 121.8(6) |
| N10-C50-C49 | 121.9(6) | N10-C50-H50 | 114.(6) |
| C49-C50-H50 | 124.(6) | N11-C51-C52 | 177.(4) |
| C51-C52-H52A | 109.5 | C51-C52-H52B | 109.5 |
| H52A-C52-H52B | 109.5 | C51-C52-H52C | 109.5 |
| H52A-C52-H52C | 109.5 | H52B-C52-H52C | 109.5 |

TABLE 9

Anisotropic atomic displacement parameters ($Å^2$) for (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.
The anisotropic atomic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| Cl1 | 0.0261(7) | 0.0489(8) | 0.0216(6) | 0.0004(6) | −0.0004(5) | −0.0161(6) |
| Cl2 | 0.0281(7) | 0.0487(8) | 0.0259(7) | 0.0014(6) | −0.0112(5) | −0.0146(6) |
| O1 | 0.027(2) | 0.046(2) | 0.021(2) | −0.0021(17) | −0.0056(16) | −0.0146(18) |
| O2 | 0.0239(19) | 0.032(2) | 0.0157(17) | 0.0010(15) | −0.0030(14) | −0.0089(16) |
| O4 | 0.021(2) | 0.042(2) | 0.025(2) | −0.0010(17) | −0.0019(16) | −0.0117(17) |
| O5 | 0.026(2) | 0.029(2) | 0.0204(19) | 0.0015(15) | −0.0039(15) | −0.0068(16) |
| O6 | 0.059(3) | 0.043(3) | 0.028(2) | −0.005(2) | −0.019(2) | 0.020(2) |
| N1 | 0.022(2) | 0.024(2) | 0.018(2) | 0.0003(18) | −0.0030(18) | −0.0063(18) |
| N2 | 0.029(3) | 0.035(3) | 0.022(2) | −0.008(2) | −0.003(2) | −0.005(2) |
| N5 | 0.050(3) | 0.034(3) | 0.024(3) | 0.001(2) | −0.003(2) | −0.009(2) |
| N6 | 0.020(2) | 0.021(2) | 0.022(2) | 0.0011(18) | −0.0059(18) | −0.0044(18) |
| N7 | 0.033(3) | 0.029(3) | 0.028(3) | −0.007(2) | −0.006(2) | −0.001(2) |
| N8 | 0.026(2) | 0.031(3) | 0.018(2) | −0.0009(19) | −0.0057(18) | −0.0018(19) |
| N9 | 0.042(3) | 0.041(3) | 0.022(3) | 0.001(2) | −0.004(2) | 0.006(2) |
| N10 | 0.038(3) | 0.041(3) | 0.029(3) | 0.001(2) | −0.006(2) | −0.013(2) |
| F1 | 0.056(2) | 0.0284(19) | 0.0333(19) | −0.0005(15) | −0.0032(16) | −0.0058(16) |
| F2 | 0.095(4) | 0.075(3) | 0.0193(19) | −0.0007(19) | 0.013(2) | −0.010(3) |
| F3 | 0.078(3) | 0.095(4) | 0.027(2) | −0.011(2) | −0.005(2) | −0.044(3) |
| F4 | 0.096(4) | 0.035(2) | 0.036(2) | −0.0049(17) | 0.007(2) | −0.024(2) |
| C1 | 0.022(3) | 0.025(3) | 0.022(3) | 0.003(2) | −0.002(2) | −0.008(2) |
| C2 | 0.023(3) | 0.024(3) | 0.022(3) | 0.002(2) | −0.003(2) | −0.010(2) |
| C3 | 0.022(3) | 0.024(3) | 0.025(3) | 0.001(2) | −0.007(2) | −0.007(2) |
| C4 | 0.024(3) | 0.027(3) | 0.019(3) | 0.004(2) | −0.007(2) | −0.010(2) |
| C5 | 0.025(3) | 0.018(3) | 0.017(3) | 0.0015(19) | −0.006(2) | −0.004(2) |
| C6 | 0.029(3) | 0.039(4) | 0.023(3) | −0.004(3) | 0.000(3) | −0.016(3) |
| C7 | 0.022(3) | 0.028(3) | 0.017(3) | 0.000(2) | −0.003(2) | −0.010(2) |
| C8 | 0.027(3) | 0.027(3) | 0.030(3) | −0.003(2) | −0.006(2) | −0.008(2) |
| C9 | 0.036(3) | 0.028(3) | 0.029(3) | −0.009(3) | −0.005(3) | −0.002(3) |
| C10 | 0.023(3) | 0.031(3) | 0.021(3) | −0.001(2) | −0.003(2) | −0.009(2) |
| C11 | 0.021(3) | 0.025(3) | 0.020(3) | −0.003(2) | −0.002(2) | −0.009(2) |
| C12 | 0.052(4) | 0.027(3) | 0.038(4) | 0.002(3) | −0.010(3) | −0.011(3) |
| C13 | 0.026(3) | 0.034(3) | 0.018(3) | 0.002(2) | −0.002(2) | −0.008(2) |
| C14 | 0.035(3) | 0.042(4) | 0.021(3) | −0.004(3) | −0.003(2) | 0.003(3) |
| C15 | 0.045(4) | 0.059(5) | 0.016(3) | 0.002(3) | −0.005(3) | 0.005(3) |
| N3 | 0.040(3) | 0.032(3) | 0.023(2) | 0.004(2) | −0.008(2) | −0.011(2) |
| N4 | 0.052(4) | 0.048(4) | 0.023(3) | 0.010(2) | −0.006(2) | −0.003(3) |
| O3A | 0.041(3) | 0.033(3) | 0.030(3) | 0.008(3) | −0.012(3) | 0.003(2) |
| C16A | 0.020(4) | 0.036(4) | 0.026(4) | 0.005(3) | 0.000(4) | −0.008(4) |
| C17A | 0.029(4) | 0.030(4) | 0.033(4) | 0.011(3) | −0.012(4) | −0.009(3) |
| C18A | 0.038(5) | 0.040(5) | 0.106(10) | 0.009(5) | −0.019(6) | −0.015(4) |
| C19A | 0.059(5) | 0.027(4) | 0.030(4) | −0.001(3) | −0.017(4) | −0.006(3) |

TABLE 9-continued

Anisotropic atomic displacement parameters (Å$^2$) for (−)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.
The anisotropic atomic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| C20 | 0.030(3) | 0.030(3) | 0.020(3) | −0.003(2) | −0.005(2) | −0.010(3) |
| C21 | 0.026(3) | 0.033(3) | 0.020(3) | −0.002(2) | −0.005(2) | −0.006(2) |
| C22 | 0.033(3) | 0.033(3) | 0.023(3) | −0.001(2) | −0.007(2) | −0.007(2) |
| C23 | 0.044(4) | 0.041(4) | 0.027(3) | −0.010(3) | −0.006(3) | −0.001(3) |
| C24 | 0.050(4) | 0.053(4) | 0.021(3) | −0.001(3) | −0.001(3) | −0.003(3) |
| C25 | 0.062(5) | 0.041(4) | 0.025(3) | 0.005(3) | 0.003(3) | −0.011(3) |
| C26 | 0.024(3) | 0.024(3) | 0.023(3) | 0.005(2) | −0.010(2) | −0.007(2) |
| C27 | 0.026(3) | 0.019(3) | 0.026(3) | 0.001(2) | −0.007(2) | −0.007(2) |
| C28 | 0.024(3) | 0.024(3) | 0.025(3) | 0.002(2) | −0.006(2) | −0.005(2) |
| C29 | 0.016(3) | 0.029(3) | 0.030(3) | 0.000(2) | 0.000(2) | −0.007(2) |
| C30 | 0.031(3) | 0.017(3) | 0.020(3) | 0.002(2) | −0.003(2) | −0.007(2) |
| C31 | 0.023(3) | 0.053(4) | 0.034(3) | −0.006(3) | −0.006(3) | −0.013(3) |
| C32 | 0.020(3) | 0.026(3) | 0.020(3) | −0.002(2) | −0.006(2) | −0.006(2) |
| C33 | 0.033(3) | 0.023(3) | 0.029(3) | −0.002(2) | −0.010(2) | −0.005(2) |
| C34 | 0.041(4) | 0.028(3) | 0.033(3) | −0.015(3) | −0.005(3) | −0.003(3) |
| C35 | 0.022(3) | 0.030(3) | 0.022(3) | −0.005(2) | −0.004(2) | −0.006(2) |
| C36 | 0.021(3) | 0.023(3) | 0.026(3) | −0.006(2) | −0.005(2) | −0.002(2) |
| C37 | 0.063(5) | 0.021(3) | 0.037(4) | −0.001(3) | −0.003(4) | 0.002(3) |
| C38 | 0.021(3) | 0.031(3) | 0.021(3) | −0.004(2) | −0.005(2) | −0.002(2) |
| C39 | 0.034(3) | 0.041(4) | 0.024(3) | −0.009(3) | −0.004(2) | 0.000(3) |
| C40 | 0.043(4) | 0.050(4) | 0.016(3) | −0.001(3) | −0.004(3) | 0.005(3) |
| C41 | 0.030(3) | 0.030(3) | 0.022(3) | 0.001(2) | −0.006(2) | −0.002(2) |
| C42 | 0.039(4) | 0.027(3) | 0.026(3) | 0.006(2) | −0.013(3) | 0.002(3) |
| C43 | 0.064(5) | 0.029(4) | 0.032(4) | −0.007(3) | 0.004(3) | 0.001(3) |
| C44 | 0.057(5) | 0.034(4) | 0.089(7) | −0.003(4) | −0.013(5) | −0.008(3) |
| C45 | 0.029(3) | 0.038(3) | 0.026(3) | −0.001(3) | 0.000(2) | −0.012(3) |
| C46 | 0.028(3) | 0.036(3) | 0.028(3) | −0.006(2) | 0.002(2) | −0.012(2) |
| C47 | 0.046(4) | 0.039(4) | 0.029(3) | −0.007(3) | 0.009(3) | −0.017(3) |
| C48 | 0.059(5) | 0.063(5) | 0.032(4) | −0.020(3) | 0.014(3) | −0.034(4) |
| C49 | 0.045(4) | 0.068(5) | 0.022(3) | −0.007(3) | 0.001(3) | −0.026(3) |
| C50 | 0.045(4) | 0.048(4) | 0.031(3) | 0.001(3) | −0.008(3) | −0.013(3) |

TABLE 10

Hydrogen atomic coordinates and isotropic atomic displacement parameters (Å$^2$) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

| | x/a | y/b | z/c | U(eq) |
|---|---|---|---|---|
| H3A | 0.5158 | −0.0749 | 1.4309 | 0.059 |
| H18A | 0.2751 | −0.1596 | 1.3407 | 0.093 |
| H18B | 0.1370 | 0.0018 | 1.3206 | 0.093 |
| H18C | 0.1797 | −0.0622 | 1.4068 | 0.093 |
| H19A | 0.5670 | 0.0497 | 1.2534 | 0.06 |
| H19B | 0.3758 | 0.0753 | 1.2261 | 0.06 |
| H19C | 0.5146 | −0.0866 | 1.2434 | 0.06 |
| H18D | 0.0788 | −0.0035 | 1.4319 | 0.096 |
| H18E | 0.2294 | −0.1584 | 1.4225 | 0.096 |
| H18F | 0.0901 | −0.0803 | 1.3597 | 0.096 |
| H19D | 0.5310 | −0.1503 | 1.3235 | 0.097 |
| H19E | 0.5116 | −0.1206 | 1.4094 | 0.097 |
| H19F | 0.5610 | −0.0088 | 1.3410 | 0.097 |
| H52A | 0.5245 | −0.0878 | 0.0396 | 0.068 |
| H52B | 0.4010 | 0.0593 | −0.0064 | 0.068 |
| H52C | 0.5513 | 0.0637 | 0.0415 | 0.068 |
| H4 | −0.062(8) | 0.666(6) | 0.940(3) | 0.017(14) |
| H6A | −0.263(11) | 0.658(9) | 1.048(5) | 0.06(2) |
| H6B | −0.147(9) | 0.578(7) | 1.127(4) | 0.028(15) |
| H6C | −0.238(9) | 0.754(7) | 1.109(4) | 0.031(16) |
| H60 | 0.514(11) | 1.070(9) | −0.438(5) | 0.05(2) |
| H9 | −0.097(9) | 0.875(7) | 1.301(4) | 0.023(15) |
| H11 | 0.208(7) | 0.452(6) | 1.196(3) | 0.015(13) |
| H12A | −0.091(10) | 1.051(7) | 1.181(4) | 0.05(2) |
| H12B | 0.066(8) | 0.990(8) | 1.121(4) | 0.05(2) |
| H12C | −0.168(9) | 0.986(10) | 1.123(5) | 0.07(2) |
| H14 | 0.149(9) | 0.501(8) | 1.448(4) | 0.029(16) |

TABLE 10-continued

Hydrogen atomic coordinates and isotropic atomic displacement parameters (Å$^2$) for (—)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one.

| | x/a | y/b | z/c | U(eq) |
|---|---|---|---|---|
| H15 | 0.253(10) | 0.278(8) | 1.530(5) | 0.05(2) |
| H20A | 0.017(9) | 0.733(7) | 0.809(3) | 0.027(15) |
| H20B | 0.126(9) | 0.552(8) | 0.827(4) | 0.034(18) |
| H23 | 0.441(11) | 0.428(9) | 0.603(5) | 0.05(2) |
| H25 | 0.255(9) | 0.869(7) | 0.573(4) | 0.030(16) |
| H29 | 0.583(9) | 0.337(7) | 0.049(3) | 0.018(16) |
| H31A | 0.605(12) | 0.246(10) | −0.122(5) | 0.07(3) |
| H31B | 0.517(9) | 0.425(8) | −0.133(4) | 0.038(18) |
| H31C | 0.461(10) | 0.331(7) | −0.068(4) | 0.030(17) |
| H34 | 1.100(9) | 0.122(8) | −0.300(4) | 0.036(18) |
| H36 | 0.777(8) | 0.541(7) | −0.195(3) | 0.020(14) |
| H37A | 1.130(17) | −0.030(14) | −0.176(7) | 0.10(4) |
| H37B | 1.202(12) | 0.034(9) | −0.123(5) | 0.06(2) |
| H37C | 0.990(12) | 0.043(9) | −0.107(5) | 0.06(2) |
| H39 | 0.860(12) | 0.514(10) | −0.449(5) | 0.06(2) |
| H40 | 0.811(8) | 0.738(7) | −0.535(4) | 0.025(15) |
| H43A | 0.426(13) | 0.927(11) | −0.258(5) | 0.08(3) |
| H43B | 0.606(13) | 0.920(10) | −0.222(5) | 0.07(3) |
| H43C | 0.447(11) | 1.075(9) | −0.243(4) | 0.05(2) |
| H44A | 0.808(15) | 1.111(13) | −0.395(4) | 0.10(4) |
| H44B | 0.705(11) | 1.168(7) | −0.316(5) | 0.07(3) |
| H44C | 0.849(11) | 0.985(8) | −0.296(4) | 0.07(3) |
| H45A | 0.570(8) | 0.293(7) | 0.187(3) | 0.020(14) |
| H45B | 0.556(8) | 0.464(7) | 0.165(3) | 0.019(14) |
| H47 | 0.682(15) | 0.573(13) | 0.394(6) | 0.10(4) |
| H50 | 0.758(13) | 0.124(11) | 0.424(6) | 0.07(3) |

Example 3: Solubility Assessment of Compound 49a

The solubility of Compound 49a was assessed in 12 solvents to support the solvent selection for the subsequent crystal-form screening experiments. The solubility was visually estimated at room temperature (RT; ~23° C.) by dosing small aliquots of solvent into a fixed amount of solid (~10 mg) until the dissolution point or a maximum volume of 1.8 mL was reached. Samples that contained undissolved solids at RT were heated to 40° C. for 1 h, and the dissolution was assessed visually. Compound 49a exhibits high solubility (>100 mg/mL) in DCM, DMSO, and THF; moderate solubility in MeCN, MeOH, EtOAc, and IPA:water (9:1); and low solubility (<10 mg/mL) in five other solvents assessed at RT. Results are shown in Table 11.

TABLE 11

Estimated Solubility of Compound 49a in 12 Solvents at RT and 40° C.

| # | Solvent (v/v) | Solubility at RT [mg/mL] | Solubility at 40° C. [mg/mL] |
|---|---|---|---|
| 1 | Dichloromethane (DCM) | >420 | N/A |
| 2 | Dimethyl sulfoxide (DMSO) | 132-528 | N/A |
| 3 | Tetrahydrofuran (THF) | 146-584 | N/A |
| 4 | Acetonitrile (MeCN) | 60-119 | N/A |
| 5 | Methanol (MeOH) | 59-118 | N/A |
| 6 | Ethyl Acetate (EtOAc) | 28-69 | N/A |
| 7 | 2-Propanol:water (9:1) | 11-22 | N/A |
| 8 | Toluene | <9 | >9 |
| 9 | 2-Propanol (IPA) | <6 | >6 |
| 10 | Water | <6 | <6 |
| 11 | Methyl t-butyl ether (MTBE) | <6 | <6 |
| 12 | Isopropyl ether (IPE) | <6 | <6 |

Example 4: Crystal Form Screen of Compound 49a

The crystal-form screening study involved a total of 48 neat and binary solvent systems which addressed the moderate solubility of the input material and provided a diverse set of polarities, dielectric constants, dipole moments, and hydrogen-bond donor/acceptor attributes. Water-containing solvents with a variety of water activities (aw)[1] were also included to probe for the formation of hydrates. Temperatures ranging between 40° C. to −20° C.

The screening studies were comprised of the following crystallization modes:

Temperature-cycled ripening of API slurries between 5-40° C. for four days (TC)

Rapid cooling clarified saturated solutions from 40 to −20° C. and holding at −20° C. for three days (RC)

Slow evaporation of clarified solutions at RT over 14 days. Rapid evaporation of solvents under reduced pressure from solutions that did not produce solids during slow evaporation after 14 days (EV).

A summary of the outcomes of the screening study are shown in Table 12.

TABLE 12

Results of the Crystal Form Screen

| # | Solvent | TC | RC | EV | Water Activity |
|---|---|---|---|---|---|
| 1 | Water | Form A | | | 1.00 |
| 2 | Methanol | | | Form A | |
| 3 | 2-Methoxyethanol:Isopropyl ether (20:80) | Form A | | Form A | |
| 4 | 1-Propanol | | | Form A | |
| 5 | Nitromethane | Form A | Form A | Form A | |
| 6 | Acetonitrile | Form A | Form A | Form A | |
| 7 | Dimethylsulfoxide:t-Butyl methyl ether (20:80) | | | Form A | |
| 8 | Acetone | | | Form A | |
| 9 | 2-Butanone | | | Form A | |
| 10 | Dichloromethane | | | Form A | |
| 11 | Methyl acetate:Heptane (20:80) | Form A | | | |
| 12 | 4-Methyl-2-pentanone | Form A | | Form A | |
| 13 | Chloroform | | | | |
| 14 | Ethyl acetate | | | Form A | |
| 15 | Chlorobenzene:Cyclohexane (20:80) | Form A | | | |
| 16 | Tetrahydrofuran | | | Form A | |
| 17 | 1,4-Dioxane | | | Form A | |
| 18 | Isopropyl ether | Form A | | | |
| 19 | Toluene | Form A | | Form A | |
| 20 | Cyclohexane | Form A | | | |
| 21 | Heptane | Form A | | | |
| 22 | 1-Butanol | Form A | | | |
| 23 | 2-Propanol | Form A | | Form A | |
| 24 | Trifluoroethanol:Isopropyl ether (20:80) | Form A | | | |
| 25 | Dimethyl carbonate | Form A | | Form A | |
| 26 | t-Butyl methyl ether | Form A | | | |
| 27 | Isopropyl acetate | Form A | | Form A | |
| 28 | Ethanol | | | Form A | |
| 29 | 1-Methoxy-2-propanol:Isopropyl ether (20:80) | Form A | | | |
| 30 | Cyclohexanone | | | | |
| 31 | N,N-Dimethylformainide:Water (20:80) | Form A | | | 0.95 |
| 32 | 2-Methoxyethyl ether:Heptane (20:80) | Form A | | | |
| 33 | Methanol:Water (95:5) | Form A | | Form A | 0.20 |

TABLE 12-continued

| Results of the Crystal Form Screen | | | | | |
|---|---|---|---|---|---|
| # | Solvent | TC | RC | EV | Water Activity |
| 34 | Acetonitrile:Water (95:5) | Form A | | | 0.94 |
| 35 | Acetone:Water (20:80) | Form A | | Form A | 0.96 |
| 36 | Tetrahydrofuran::Water (20:80) | Form A | | Form A | 0.82 |
| 37 | 2-propanol:Water (95:5) | Form A | | Form A | 0.55 |
| 38 | Methanol:Water (90:10) | Form A | Form A | Form A | 0.33 |
| 39 | Acetonitrile:Water (90:10) | Form A | | Form A | 0.76 |
| 40 | Acetone:Water (90:10) | | | Form A | 0.70 |
| 41 | Tetrahydrofuran:Water (90:10) | | | Form A | 0.83 |
| 42 | 1,4-Dioxane:Water (90:10) | | | Form A | 0.70 |
| 43 | 2-propanol:Water (90:10) | | Form A | Form A | 0.65 |
| 44 | Acetone:Water (80:20) | | Form A | Form A | 0.77 |
| 45 | Ethanol:Water (20:80) | Form A | | | 0.93 |
| 46 | Ethyl acetate:Cyclohexane (20:80) | Form A | | | |
| 47 | Acetonitrile:Isopropyl ethyl ether (20:80) | Form A | | | |
| 48 | 4-Methyl-2-pentanone:Heptane (20:80) | Form A | | | |

Example 5: Single Crystal Structure Determination of Compound 49a (Form A)

The crystalline form of the Compound 49a has been characterized relative to the absolute stereochemical configuration of the spatial arrangement of the atoms using single crystal X-ray diffraction. A detailed description of structure determination by X-ray diffraction is provided in Stout & Jensen, X-Ray Structure Determination: A Practical Guide, Macmillan Co., New York (1968), Chapter 3, which is herein incorporated by reference. Alternatively, the unique spatial arrangements of atoms in three dimensions within the crystalline lattice may be characterized by X-ray powder diffraction analysis. A detailed description of X-ray powder diffraction is provided in Cullity, B. D. Elements of X-ray Diffraction. Addison-Wesley, (1978) ISBN 0-201-01174-3 Chapter 14), which is herein incorporated by reference. XRPD data consists of experimentally determined values of the two-theta position, the intensity values of multiple crystallographic reflections, also known as Bragg reflections, and their peak shape. The XRPD data may be analyzed computational, including by the method of Rietveld refinement. A detailed description of Rietveld refinement of X-ray powder diffraction data is provided in Pecharsky, Vitalij K.; Zavalij, Peter Y. (2009) Fundamentals of powder diffraction and structural characterization of materials (2nd ed.). New York: Springer. ISBN 978-0-387-09579-0. OCLC 314182615, which is herein incorporated by reference.

XRPD data may be collected at various temperatures or pressures in order to facilitate Rietveld refinement. The experimental XRPD data including 2-theta values, d-spacing, Bragg reflections and intensity values may be compared to a simulated XRPD pattern derived from the single crystal structure determination which represents an idealized pure powder, using a computational method such as described in Macrae, Clare F., et al. "Mercury 4.0: from visualization to analysis, design and prediction." Journal of Applied Crystallography vol. 53, 226-235. 1 Feb. 2020, doi:10.1107/S1600576719014092.

One of ordinary skill in the art will appreciate that an X-ray powder diffraction pattern may be obtained with a measurement error that is dependent upon the measurement conditions employed in the data collection. It is generally accepted that the peak shape, intensity values and two-theta positions derived from an X-ray powder diffraction pattern can fluctuate depending upon the type of instrument used, the measurement conditions and the method of computational analysis performed. It should be further understood that that the two-theta values and their relative intensities may also vary and accordingly, the exact order of intensity values should not be taken into account.

Additionally, the experimental error for diffraction angle measurements for a conventional X-ray powder diffraction pattern is typically about 5% or less. Assessment of the extent of measurement error should be taken into account when describing the position of the two-theta diffraction peaks. Consequently, it is to be understood that the crystal forms described in this invention are not limited to the crystal forms that provide X-ray powder diffraction patterns completely identical to the X-ray powder diffraction patterns depicted in the accompanying Figures disclosed herein. Any crystal forms that provide X-ray powder diffraction patterns substantially identical to those disclosed in the accompanying Figures fall within the scope of the present invention. The ability to ascertain substantial identities of X-ray diffraction patterns is within the purview of one of ordinary skill in the art. Likewise, it is to be understood that any crystal forms that provide differential scanning calorimetry (DSC) and/or thermogravimetric analysis (TGA) substantially identical to those disclosed in the accompanying Figures fall within the scope of the present invention. The ability to ascertain substantial identities of these patterns is within the purview of one of ordinary skill in the art.

Crystalline Form A of Compound 49a is anhydrous and was obtained from crystallization conditions described in Example 4 utilizing various organic solvents and organic/water solvent systems.

X-Ray Powder Diffraction (XRPD) diffractograms were acquired on PANalytical X'Pert Pro diffractometer using Ni-filtered Cu Ka (45 kV/40 mA) radiation and a step size of 0.02°±2θ and X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers.

Values of significant Bragg reflections, their 2-theta positions and d-spacing values, as compared to results from simulated XRPD data of crystalline Form A of Compound 49a are shown in table 13 and the XRPD spectrum is shown in FIG. 4.

TABLE 13

| Experimental and simulated XRPD data | | | | | | |
|---|---|---|---|---|---|---|
| Experimental XRPD data | | Simulated XRPD data | | | | |
| 2-Theta | d | Bragg Reflections | | | 2-Theta | d-spacing |
| (°) | (Å) | h | k | l | (°) | (Å) |
| 5.21 | 16.946 | 0 | 0 | 1 | 5.20 | 17.2385 |
| 9.78 | 9.0362 | 0 | 1 | 0 | 9.80 | 8.99183 |
| 10.27 | 8.6059 | 0 | 1 | 1 | 10.26 | 8.48713 |
| 13.00 | 6.8073 | 0 | 1 | 2 | 13.16 | 6.92863 |
| 15.34 | 5.7705 | 0 | 1 | −2 | 15.22 | 5.81934 |
| 15.51 | 5.7099 | 0 | 0 | 3 | 15.41 | 5.74618 |
| 16.92 | 5.2351 | 0 | 1 | 3 | 17.07 | 5.33869 |
| 17.92 | 4.9473 | 1 | 1 | −2 | 17.91 | 4.94901 |
| 18.86 | 4.7017 | 1 | −1 | 1 | 18.85 | 4.70444 |
| 19.60 | 4.5254 | 0 | 2 | 1 | 19.66 | 4.58616 |
| 20.57 | 4.3147 | 1 | −1 | −2 | 20.65 | 4.30016 |
| 21.01 | 4.2259 | 0 | 2 | 2 | 20.92 | 4.24356 |
| 23.60 | 3.7675 | 0 | 2 | −2 | 23.58 | 3.77065 |
| 24.29 | 3.6608 | 0 | 1 | −4 | 24.13 | 3.65807 |
| 25.92 | 3.4341 | 2 | 2 | 2 | 25.70 | 3.46431 |
| 29.05 | 3.0712 | 1 | −2 | 2 | 29.19 | 3.0598 |
| 29.48 | 3.0275 | 0 | 3 | 1 | 29.48 | 3.02715 |

Differential Scanning Calorimetry (DSC) was conducted with a TA Instruments Q100 differential scanning calorimeter equipped with an autosampler and a refrigerated cooling system under 40 mL/min $N_2$ purge. DSC thermograms were obtained at 15° C./min in crimped Al pans.

Thermogravimetric Analysis (TGA) thermograms were obtained with a TA Instruments Q500 thermogravimetric analyzer under 40 mL/min N2 purge at 15° C./min in Pt or Al pans.

DSC analysis indicates crystalline Form A of Compound49a exhibits a melting/racemization event at 187.92° C., followed by a recrystallization event at 195.8° C., and finally a sharp endotherm at 253.5° C. (melt of racemate). Negligible weight loss (0.7%) is observed between 25-256° C. by TGA. DSC and TGA thermograms are shown in FIG. 5.

Figure 6:
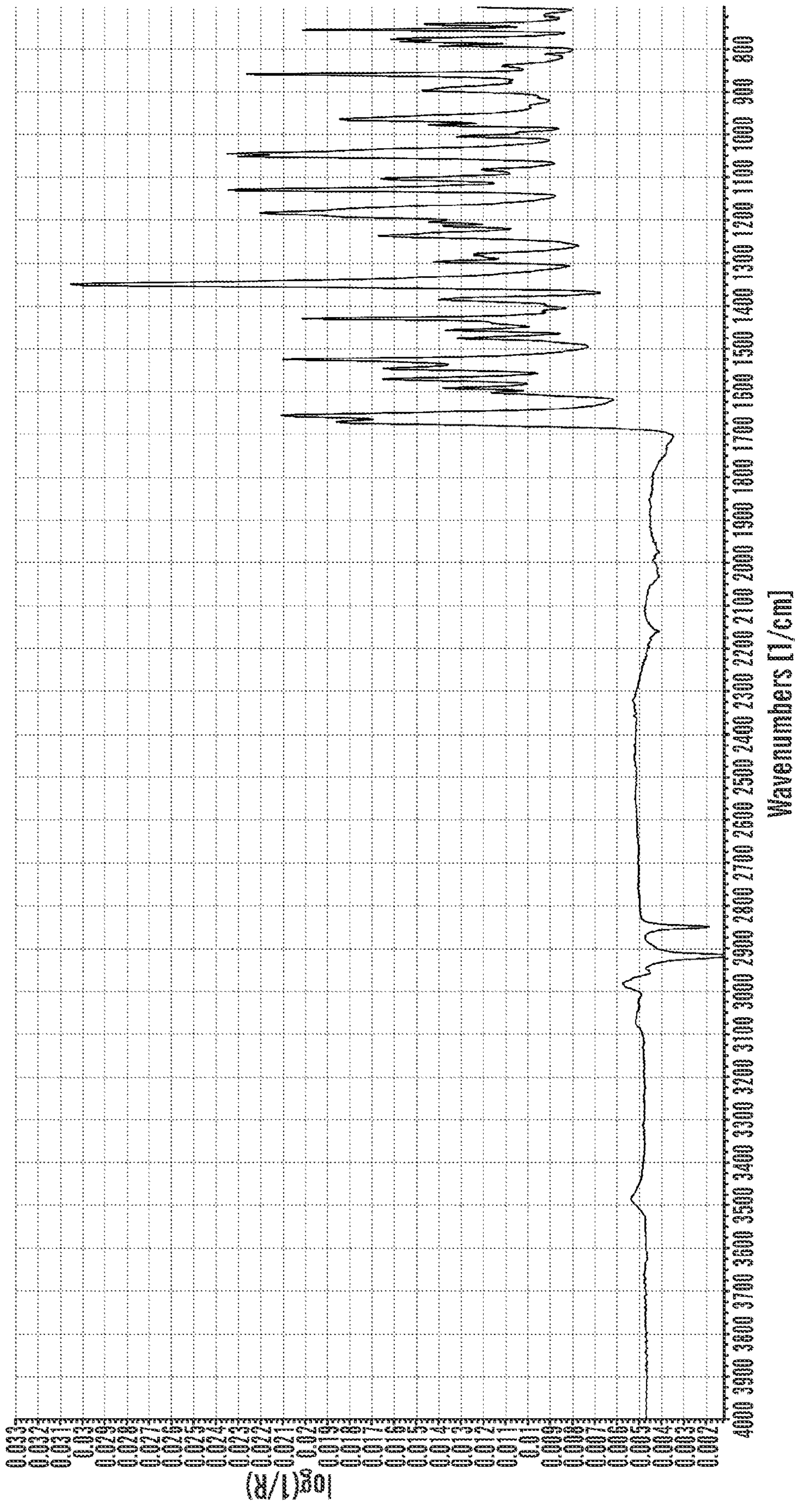
FIG. 6 shows characteristic spectral absorbance plot from Fourier Transform Infrared Spectroscopy (FT-IR) for crystalline Form A of Compound 49a showing the location of significant IR-active regions.

Fourier Transform Infrared Spectroscopy (FT-IR): Characteristic spectral absorbance data from FT-IR of Form A of Compound49a showing the location of significant IR-active regions and their functional group assignments is shown in table 14. FT-IR absorbance plot showing the location of significant IR active regions is shown in FIG. 6.

TABLE 14

| FT-IR Absorbance Data | |
|---|---|
| Wavenumber (cm−1) | Functional Group Assignment |
| 3486 | —OH stretch |
| 3072 | C—H (aromatic) stretch |
| 2982 | C—H (CH3) stretch |
| 1656 | C═O stretch |
| 1605 | C═N stretch |
| 1592 | C═N stretch |
| 1571 | C═C stretch |
| 1546 | C═N stretch |
| 1525 | C═C stretch |
| 1476 | C—H (CH2) bend |
| 1457 | CH2 scissor |
| 1429 | C—H (CH3) bend |
| 1385 | C—H (gem dimethyl) bend |
| 1380 | —O—H bend |
| 1350 | C—N(pyridone) stretch |
| 1296 | C—F stretch |
| 1237 | C—O (conjugated, alkyl ether) stretch |
| 1214 | C—H (aromatic) bend |

TABLE 14-continued

| FT-IR Absorbance Data | |
|---|---|
| Wavenumber (cm−1) | Functional Group Assignment |
| 1184 | C—O (tertiary alcohol) stretch |
| 1130 | C—F stretch |
| 1103 | C—H (aromatic) bend |
| 1051 | C—F stretch |
| 1044 | C—F stretch |
| 1005 | C—H (aromatic) bend |
| 978 | C—H (aromatic) bend |
| 964 | C—H (aromatic) bend |
| 860 | C—H (aromatic) bend |
| 840 | C—H (aromatic) bend |
| 810 | C—H (aromatic) bend |
| 793 | C—H (aromatic) bend |
| 781 | C—H (aromatic) bend |
| 755 | C—Cl stretch |
| 741 | C—H (aromatic) bend |
| 703 | C—H (aromatic) bend |
| 669 | N—C═O bend |

Example 6: Scale-Up of Phase-Pure of Compound49a

A scale-up procedure to produce phase-pure crystalline Form A of Compound 49a has been developed.

Compound 49a (4.927 g) was combined with MeOH/5% water (40 mL) and temperature cycled with stirring between 40-5° C. for four days. Aliquots were sampled, isolated by filtration, air-dried for 30 minutes and analyzed by DSC which showed presence of the racemate.

Approximately 0.5 mL was transferred to a 2 mL vial and heated to 60° C., filtered through a 0.2 μm syringe filter and the filtrate cooled to 5° C. No solids were observed. Water (60 μL) was added dropwise with stirring and solids were observed. The solids were isolated by filtration, air-dried and analyzed by DSC showing no racemate present. MeOH/5% water (20 mL) was added and the slurry was heated to 60° C. with stirring for 30 minutes. The slurry was filtered through a 0.2 μm syringe filter into a clean bottle, naturally cooled to RT, and water (6 mL) was added in 500 μL aliquots so that the filtrate remained cloudy. The filtrate was seeded and stirred at RT for 30 minutes. An aliquot of the slurry was sampled, filtered, air-dried for 15 minutes and analyzed by DSC showing no racemate present. The slurry was isolated by filtration using Whatman #1 paper and the mother liquor was recycled to wash the slurry bottle and added to the filter. The cake was air-dried for one hour and dried in a vacuum oven at 50° C. with slow $N_2$ bleed for 16 hours. Yield: 3.210 g (65%).

Figure 7:
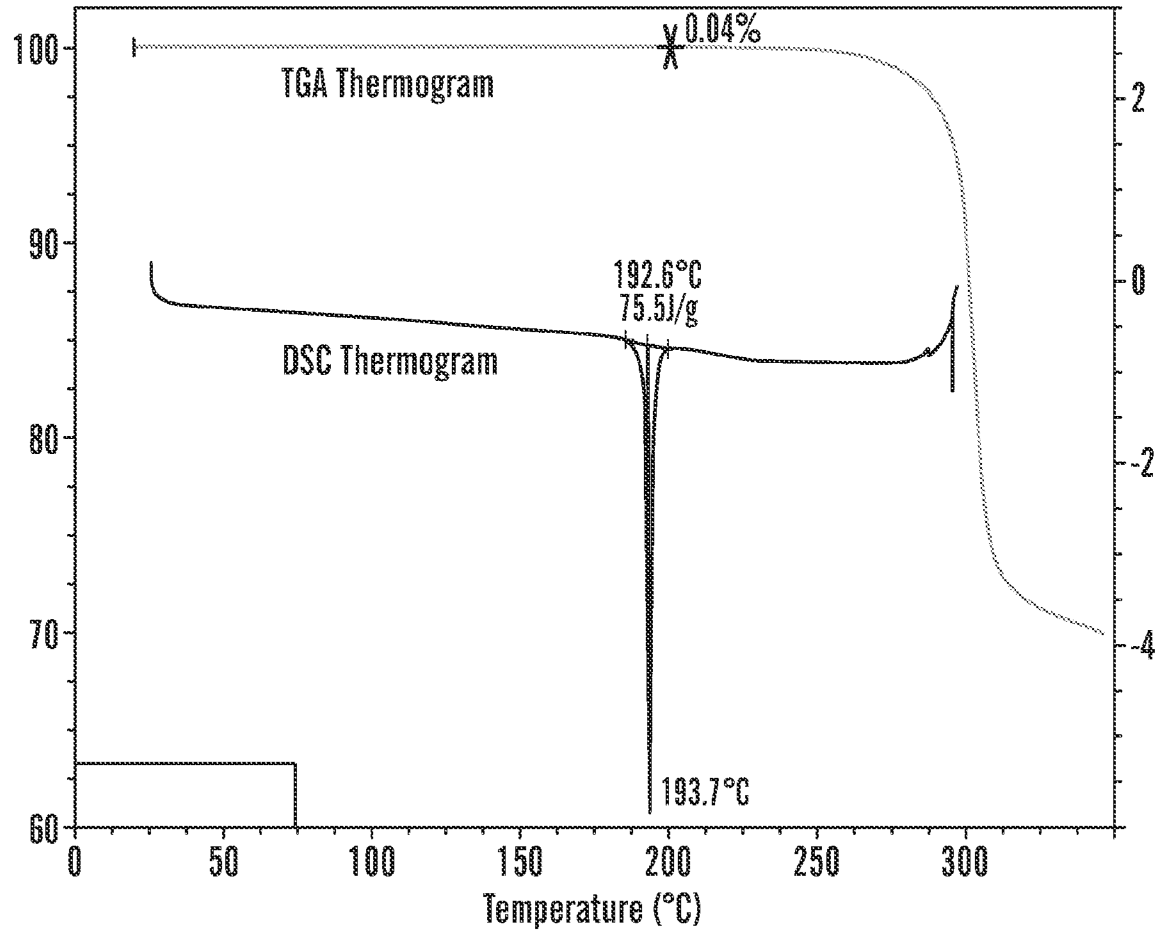

DSC analysis indicates crystalline Form A of Compound 49a exhibits a single melt event at 192.6° C. No racemate was observed by DSC analysis. Negligible weight loss (<0.1%) is observed between 25-200° C. by TGA. DSC and TGA thermograms are shown in FIG. 7.

Example 7: Multi-Kilo Scale Crystallization of Compound 49a

A multi-kilo scale crystallization procedure to produce crystalline Form A of Compound 49a has been developed.

Charged Compound 49a (1.0 eq.) and isopropyl alcohol (19 vol.) into the reactor at 25-35° C. Then heated the reaction mass to 72-77° C. stirred for homogeneous solution. Maintained the reaction mass for 1-2 hours. Filtered the reaction mass at 72-77° C. Cool the reaction mass to 55-58° C. and added Form A of Compound 49a (0.005 T w/w) as seed material. Raised the temperature to 70-75° C. and stirred for 1-2 h. Adjust the reaction mass temperature to 57-60° C. Stir for 3-4 h at 55-58° C. Cool the reaction mass to 25-30° C. Stirred for 12-15 h. Cool the reaction mass to 7.5-12.5° C. over a period of 2-3 h and stirred for 4-5 h. Filtered the solid and washed with IPA (2 vol.). Dried the material at 50-55° C. till the sample complies the chiral purity, individual impurity content and total impurities by HPLC to afford Form A of Compound 49a as an Off-white color solid. Dry sample was sent for XRPD and DSC profile. The final product was sampled for water content by Karl-Fischer titration. Results of 3 batches are shown in table 15.

TABLE 15

| Batch | Input of Compound 49a (Kg) | Input of Form A of Compound 49a (Kg) | Yield | HPLC Purity |
|---|---|---|---|---|
| 1 | 3.5 Kg | 2.96 Kg | 84.6% w/w | 100.0% |
| 2 | 2.0 Kg | 1.73 Kg | 86.5% w/w | 99.8% |
| 3 | 2.4 Kg | 2.038 Kg | 85% w/w | 99.49% |

Biological Evaluations

List of Biological Evaluation Abbreviations

- p38 Class of mitogen-activated protein kinases that are responsive to stress stimuli
- MAP Mitogen activated protein kinase
- MK2 Also known as MAPKAPK2. Refers to MAP kinase-activated protein kinase 2
- PRAK p38 regulated/activated kinase
- GST Glutathione S-transferase
- Hsp27 Heat-shock protein 27
- BSA Bovine serum albumin
- DTT Dithiothreitol
- ATP Adenosine triphosphate
- $IC_{50}$ Amount of a drug that's needed to inhibit a process by half
- $EC_{50}$ concentration of a drug which induces a response halfway between the baseline and maximum after a specified exposure time
- TNF Tumor necrosis factor
- IL Interleukin
- JNK c-Jun N-terminal kinase
- RPMI Roswell Park Memorial Institute medium. A medium for cell and tissue culture
- HWB Human whole blood
- DMEM Dulbecco's modified Eagle's medium. A vitamin and nutrient-enriched cell culture.
- FBS Fetal bovine serum
- RASF Rheumatoid arthritis synovial fibroblasts
- Tiny-TIM TNO gastro-Intestinal Model of the stomach and one-compartmental small intestine
- HKW House Keeper Wave
- TMIS Test Material Information Sheet
- BAmax Maximal bioaccessibility
- Tmax Time interval where BAmax is recorded

Example 8: Release and Bioaccessibility of Form a of Compound 49a from an Oral Dosage Form During Transit Through the Dynamic Gastrointestinal Model Tiny-TIM A study was conducted to compare the release, solubility and availability for absorption (bioaccessibility) of formulated 50 mg strength tablet (consisting of 12.5 wt % crystalline Form A of Compound 49a, 71 wt % silicified microcrystalline cellulose, 10 wt % mannitol, 5 wt % crospovidone, 0.75 wt % hydrophilic fumed silica, and 0.75 wt % magnesium stearate) under fasted and fed state conditions during transit through the dynamic, computer-controlled model of the stomach and small intestine (tiny-TIM). The findings from these experiments aid in characterization of the formulation with regard to its bioaccessibility profile under both conditions.

Figure 8:
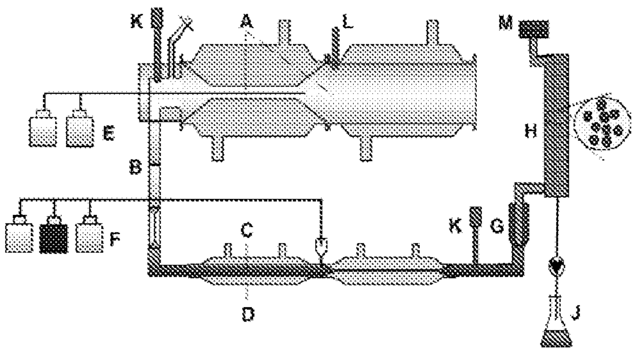
FIG. 8 shows the arrangement of the tiny-TIM system.

Test System: The study was performed in the TNO dynamic, multi-compartmental in vitro system of the stomach and small intestine (tiny-TIM). The tiny-TIM system consists of a gastric compartment and one small intestinal compartment (FIG. 8). This compartment is composed of two glass units with a flexible silicone inner wall enclosing the luminal material. The space between the inner and outer walls is filled with water. Peristaltic mixing of the chyme is the result of alternate compression and relaxation of the flexible inner wall. The compartments are connected by peristaltic valve pumps that successively open and close, allowing the chyme to transit over time through the compartments. This way, oral dosage forms/API's are exposed to locally changing and physiological relevant conditions in the stomach and of the small intestine for tiny-TIM. The tiny-TIM system mimics the intraluminal pH, enzyme activity, bile salt concentrations, peristaltic movements, and gastro-intestinal transit of the contents. The set-points for gastro-intestinal simulation are controlled and monitored by specific computer programs. Released and dissolved drug molecules are removed from the intestinal lumen by semi-permeable membrane units connected to the small intestinal compartment. This allows the assessment of the so-called bioaccessible fraction, i.e. the fraction of the drug which is available for small intestinal absorption.

For simulation of the fasted state condition, a glass of water (240 mL) was administered to the tiny-TIM system. For simulation of the fed state condition, a High Fat Meal (HFM) was used as recommended by the FDA for clinical studies. This meal contains approximately 50 energy % fat, 20 energy % protein and 30 energy % in the form of carbohydrates. The meal is composed of eggs, bacon, toast bread, potatoes, milk, butter and margarine. The meals were prepared as one batch, divided in portions of 150 g and stored at 5-18° C. Per tiny-TIM run, one portion of the meal was used.

The experiments in tiny-TIM were performed under simulation of the average physiological conditions in the gastro-intestinal tract as described for humans in the fasted and fed state. These conditions included especially the dynamics of gastric emptying and pH decline, intestinal transit times, housekeeper wave, the gastric and the intestinal pH values (Table 16), and the composition and activity of the secretion products. The digested and soluble (low-molecular) compounds were removed continuously from the intestinal compartment of the model via a special membrane system. Prior to the performance of each experiment the secretion fluids (e.g. gastric juice with enzymes, electrolytes, bile, and pancreatic juice) were freshly prepared, the pH electrodes calibrated, and semipermeable membrane (hollow fiber) units installed. The housekeeper wave (HKW) was simulated after 60 minutes (fasted state) and 180 minutes (fed state) by transferring residual material from the gastric compartment to the intestinal compartment.

TABLE 16

| Parameters simulated in the tiny-TIM, describing the average gastrointestinal physiological conditions of healthy young adults (HFM = high fat meal) | | |
|---|---|---|
| Tiny-TIM | Fed state (HFM) | Fasted state |
| Gastric compartment tiny-TIM | | |
| Intake (total) | 300 g | 270 g |
| Meal (HFM) | 150 g | — |
| Water and artificial saliva | 140 g | 240 g |
| Gastric start fluid | 10 g | 30 g |
| Gastric emptying T½ | 80 min | 20 min |
| House keeper wave | 180 min | 60 min |
| Gastric pH | 6.5 to 1.7 in 180 min | 3.0 to 1.8 in 30 min |
| Small intestinal compartment tiny-TIM | | |
| pH intestinal compartment | 6.5 | 6.5 |
| Experimental duration | 6 hours | 5 hours |

Filtration of released and dissolved/solubilized drug molecules from the intestinal lumen via a semi-permeable membrane unit (Fresenius plasmaFlux® P1dry) allowed the assessment of the so-called bio-accessible fraction, i.e. the fraction of the drug which is available for small intestinal absorption. The analysis of these samples generated a bio-accessibility profile over time. Filtrate fractions from the intestinal compartment were collected in 30 minute intervals (0-30, 30-60, 60-90, 90-120, 120-150, 150-180, 180-210, 210-240, 240-270, 270-300, 300-330, and 330-360 min). The collected volume per time period was measured and sub-samples were taken, instantly diluted in 50% Acetonitrile in Milli-q water and stored at 2-10° C., protected from light, until analysis.

Lumen samples from the intestinal compartment were collected to determine the crystalline Form A of Compound 49a concentrations. These samples were collected every 30 minutes (30, 60, 90, 120, 150, 180, 210, 240, 270, 300, 330[1] and 360[1] min). Lumen samples from the intestinal compartment were collected to determine the crystalline Form A of Compound 49a concentrations. These samples were collected every 30 minutes (30, 60, 90, 120, 150, 180, 210, 240, 270, 300, 330, and 360 min).

Upon completion of the experiments the residues of the stomach and the intestinal compartment were collected separately. Any remains of the dosage form were also be collected separately. Each compartment was rinsed twice with 50% Acetonitrile in Milli-q water. This rinse was pooled with the residue sample of the same compartment, the volume measured and stored at 2-10° C., protected from light, until analysis.

The absolute amount of the API recovered in a sample is calculated by multiplying the analyzed concentration in the sample with the collected volume (equation 1).

$$A(mg)=C_{sample}(\mu g/ml)\cdot 10^{-3}\cdot V_{sample}(ml) \quad (1)$$

The recovery of the API is determined by the sum of all amounts recovered in the filtrate fractions of the jejunum and the ileum, in the ileum effluent and in the residues and rinse fractions of the gastric-, duodenum-, jejunum- and ileum compartment and the drug product. The total recovery is expressed as % of amount added (equation 2).

$$\text{Recovery }(\%) = \frac{\sum A_{filtrate}(\text{mg}) + \sum A_{effluent}(\text{mg}) + \sum A_{residues}(\text{mg})}{A_{added}(\text{mg})}\cdot 100\% \quad (2)$$

The bioaccessibility (% of intake) is calculated by expressing the amount of API recovered from the filtrate as a percentage of the intake (equation 3).

$$\text{Bioaccessibility (\% of dose)} = \frac{\sum A_{filtrate}(\text{mg})}{A_{added}(\text{mg})}\cdot 100\% \quad (3)$$

The results of the duplicate runs are presented as mean SD. For the SD, in Microsoft Excel the STDEVP function was used (equation 4).

$$Stdevp = \sqrt{\frac{\sum(x-\bar{x})^2}{n}} \quad (4)$$

The test product (TP, crystalline Form A of Compound 49a) was tested in duplicate at 50 mg under both fasted and fed state conditions in order to identify a possible food effect. The individual values expressed as percentage of intake (% of intake) are presented in Tables 17 and 18. For all four tiny-TIM runs that were performed in phase 2, the recoveries ranged from 97.8-103.7% of intake (Tables 17 and 18).

TABLE 17

| | | Percentage of intake | | | |
|---|---|---|---|---|---|
| | | TP#1, 50 mg fasted | | TP#1, 50 mg fed | |
| | Time (min) | run 1 | run 2 | run 1 | run 2 |
| Intestinal filtrate | 0-30 | 10.4 | 9.03 | 0.15 | 0.37 |
| | 30-60 | 15.1 | 13.9 | 8.29 | 7.04 |
| | 60-90 | 19.6 | 18.3 | 18.1 | 16.4 |
| | 90-120 | 11.7 | 11.7 | 19.6 | 19.6 |
| | 120-150 | 9.00 | 9.28 | 16.3 | 15.7 |
| | 150-180 | 6.11 | 6.16 | 11.8 | 12.6 |
| | 180-210 | 5.06 | 5.36 | 11.7 | 11.1 |
| | 210-240 | 3.04 | 3.36 | 4.98 | 5.33 |
| | 240-270 | 2.56 | 2.69 | 3.68 | 4.11 |
| | 270-300 | 1.39 | 1.73 | 2.42 | 2.70 |
| | 300-330 | | | 1.52 | 1.79 |
| | 330-360 | | | 0.89 | 1.02 |
| Total Intestinal filtrate | | 83.9 | 81.5 | 99.5 | 97.8 |
| Lumen samples total | | 1.44 | 1.50 | 1.17 | 1.21 |
| Residues | Gastric | 1.43 | 2.47 | 0.84 | 1.31 |
| | Intestinal | 12.4 | 12.4 | 2.20 | 2.76 |
| Total residues | | 13.8 | 14.9 | 3.04 | 4.07 |
| Recovery | | 99.2 | 97.8 | 103.7 | 103.1 |

TABLE 18

| Intestinal lumen concentrations | TP#1, 50 mg fasted | | TP#1, 50 mg fed | |
|---|---|---|---|---|
| (µg/mL) | run 1 | run 2 | run 1 | run 2 |
| 30 min | 124 | 115 | 24.3 | 21.6 |
| 60 min | 118 | 119 | 77.2 | 59.2 |
| 90 min | 84.0 | 119 | 54.1 | 74.6 |
| 120 min | 57.2 | 52.6 | 77.4 | 75.6 |
| 150 min | 39.3 | 34.2 | 62.9 | 65.4 |
| 180 min | 23.6 | 22.2 | 38.4 | 39.7 |
| 210 min | 13.1 | 14.0 | 21.8 | 25.4 |
| 240 min | 9.57 | 11.4 | 13.0 | 17.0 |
| 270 min | 6.34 | 7.44 | 9.56 | 10.4 |
| 300 min | 5.01 | 5.17 | 5.96 | 6.70 |
| 330 min | | | 3.70 | 4.26 |
| 350 min | | | 2.40 | 3.05 |

To correct for the differences in recovery, the results described below are expressed as percentage of recovery, unless stated otherwise.

Figure 9:
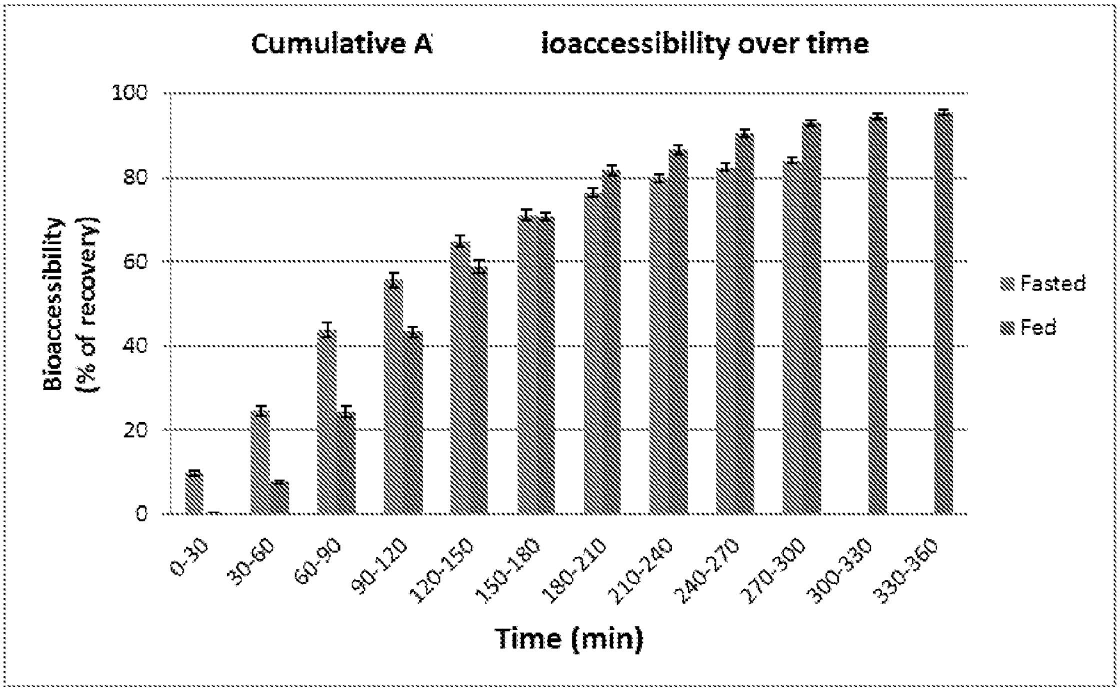
FIG. 9 shows the cumulative crystalline Form A of Compound 49a bioaccessibility over time at 50 mg dose level under fasted and fed state conditions (average±stdevp are presented).

The average small intestinal (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one bioaccessibility was 84.0±0.7% of recovery under fasted state conditions and 95.4±0.5% of recovery under fed state conditions (Table 19). The increased crystalline Form A of Compound 49a bioaccessibility under fed state conditions indicates a small positive food effect. The individual results of these experiments expressed as percentage of intake (% of intake) as well as the luminal concentrations in the intestinal compartment are presented in Table 17 and 18. The values expressed as percentage of recovery (% of recovery) for each test product can be found in FIGS. 9 and 10.

TABLE 19

Total (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one, luminal samples, residue values (% of recovery) and recovery (% of intake) of all tiny-TIM runs performed (average ± stdevp are presented)

| Phase 2 results (% of recovery) | Fasted state | Fed state |
|---|---|---|
| Bioaccessibility | 84.0 ± 0.7 | 95.4 ± 0.5 |
| Lumen samples | 1.49 ± 0.04 | 1.15 ± 0.02 |
| Total residues | 14.5 ± 0.6 | 3.44 ± 0.51 |
| Recovery (% of intake) | 98.5 ± 0.7 | 103.4 ± 0.3 |

Figure 10:
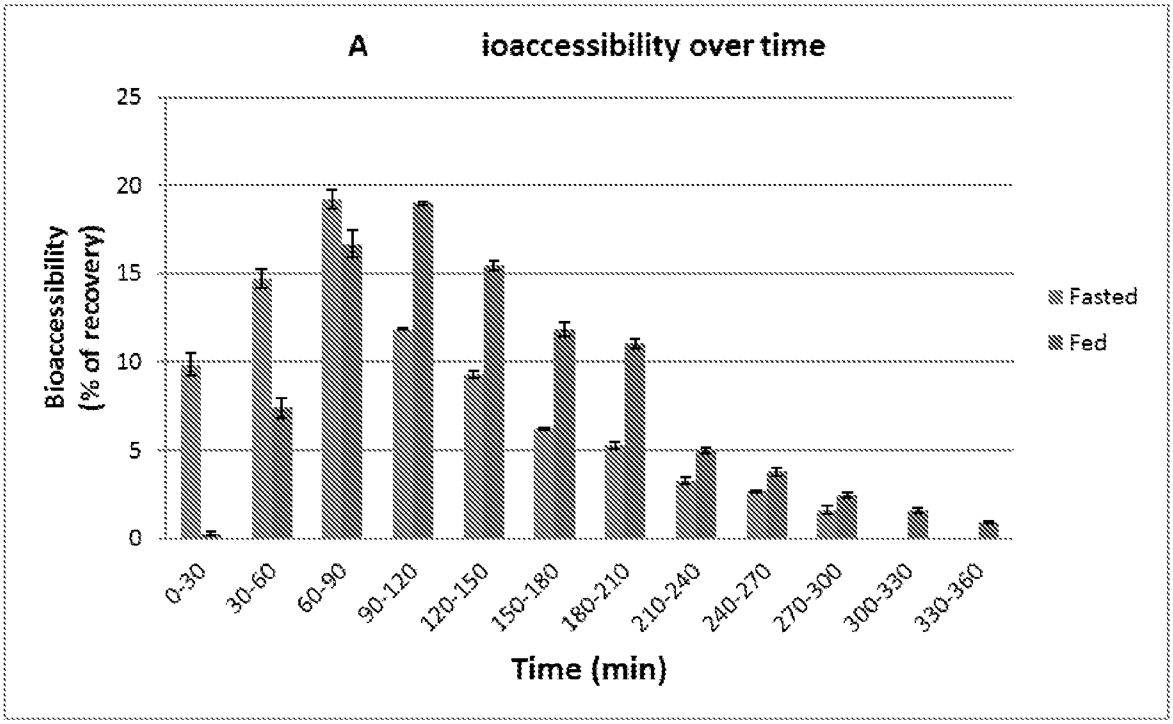
FIG. 10 shows crystalline Form A of Compound 49a bioaccessibility over time at 50 mg dose level under fasted and fed state conditions (average±stdevp are presented).

The highest levels of (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one bioaccessibility (BAmax) were observed in the sample collected between 60-90 minutes for the fasted state and in the sample collected between 90-120 minutes for fed state conditions (FIG. 10 and Table 20). The individual $BA_{max}$ values at the mean $T_{max}$ time intervals were as follows: 18.7 and 19.7% of recovery for the fasted state runs and 18.9 and 19.1% of recovery for the fed state runs. This means that although the $T_{max}$ shifted when testing under fed state conditions, the BAmax values remained similar under fasted and fed state conditions.

TABLE 20

$T_{max}$ and $BA_{max}$ values for phase 2 tiny-TIM runs (for $BA_{max}$ values, average ± stdevp are presented)

| Phase 2 $T_{max}$ and $BA_{max}$ | Fasted state | Fed state |
|---|---|---|
| $T_{max}$ (min) | 60-90 | 90-120 |
| $BA_{max}$ (% of recoveiy) | 19.2 ± 0.5 | 19.0 ± 0.1 |

Figure 11:
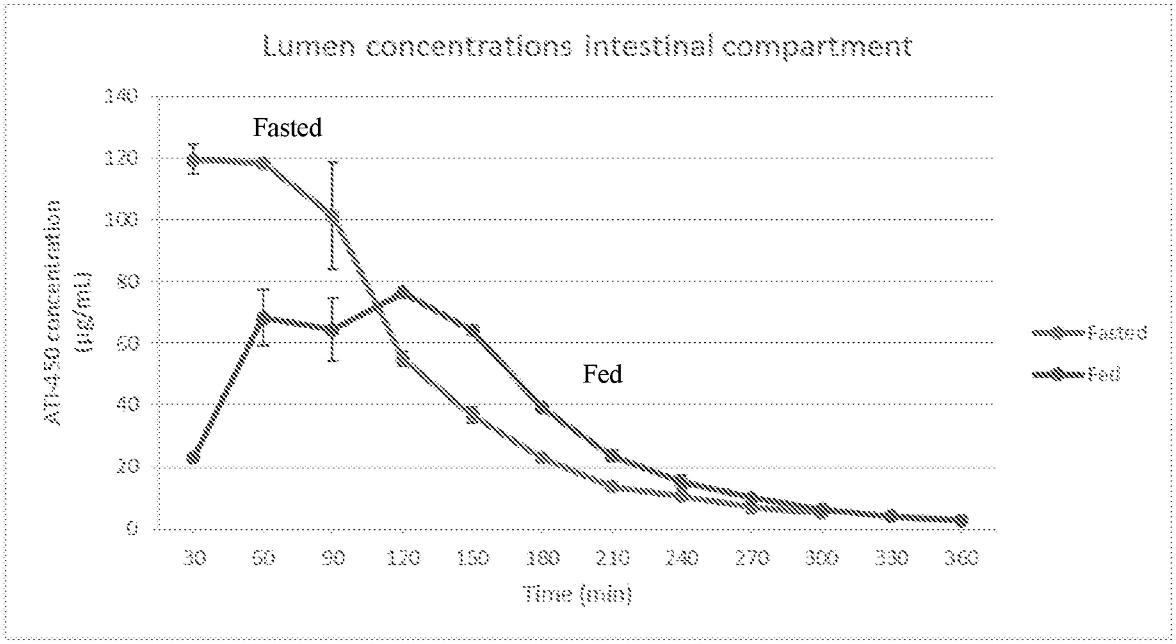
FIG. 11 shows Luminal crystalline Form A of Compound 49a concentrations in the intestinal compartment over time at 50 mg dose level under fasted and fed state conditions (average±stdevp are presented).

In order to gain insight into the intestinal concentration of (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one during the tiny-TIM experiments, luminal samples from the intestinal compartment were collected at different time points indicated above. The results of these samples, which provide a snap-shot insight into the total luminal API concentrations, are presented in FIG. 11. As expected, the fasted state total luminal concentrations where highest during the first 60 minutes of the experiments, which corresponds with the gastric emptying half-life of 20 minutes for the fasted state. For the fed state, the gastric emptying half-life was 80 minutes, thus generating a luminal concentration profile corresponding with slower gastric emptying for the fed state condition.

Example 9: P38 Inhibitory Potency and p38/MK2 Substrate Selectivity

This study evaluated the invention compound potency in inhibiting the p38 pathway. p38 activates MK2 and PRAK via phosphorylation, which both then interact with Hsp27, leading to increased inflammation and decreased ability to manage shock. The study measured the amount of the invention compound necessary to inhibit activation of MK2 and PRAK by half This is a measurement of how effective the invention compound is in helping to lower inflammatory response, which helps treat many diseases, including autoimmune conditions, lymphoma, and rheumatoid arthritis. The novel, MK2 substrate-selective inhibitory mechanism of compounds were evaluated in enzyme assays comparing inhibitor potency in blocking p38/MK2 versus p38/PRAK induced phosphorylation of an HSP-27 derived peptide substrate. The ability of compounds to inhibit activated phospho-p38α was evaluated using a p38α/MK2 and a p38u/PRAK cascade assay format. The kinase activity of p38α was determined by its ability to phosphorylate GST-MK2 or GST-PRAK. Activation of MK2 or PRAK by p38α was quantitated by measuring the phosphorylation of a fluorescently-labeled, MK2/PRAK specific peptide substrate, Hsp27 peptide (FITC-KKKALSRQLSVAA). The phosphorylation of the Hsp27 peptide was quantified using IMAP technology (Molecular Devices, Sunnyvale CA). Kinase reactions were carried out in a 384-well plate (Greiner, 781280) in 20 mM HEPES pH 7.5, 10 mM MgCl2, 0.01% Triton X-100, 0.01% BSA, 1 mM DTT, and 2% DMSO. The inhibitor concentration was varied between 0.02-30,000 nM, while the Hsp27 peptide substrate and MgATP were held constant at 1 µM and 10 µM, respectively. Activated p38α was added to a final concentration of 30 µM for reactions with nonphosphorylated 1 nM GST-MK2 in the cascade reaction. For the p38α/PRAK cascade, unactivated GST-PRAK was held constant at 10 nM while p38α was added in to a final concentration of 200 µM. Kinase reactions were incubated at room temperature and quenched after 120 minutes by the addition of IMAP Binding Solution. Under these conditions, approximately 20% of the substrate Hsp27 peptide was phosphorylated. Reactions were initiated by the addition of activated p38α except for preincubation experiments, where reactions were initiated by the addition of Hsp27 peptide and MgATP. Preincubation of p38α with inhibitor or p38α with unactivated GST-MK2 or unactivated GST-PRAK and inhibitor were performed at 2X final assay concentrations at room temperature 240 minutes prior to adding ATP and Hsp27 peptide to initiate catalysis. The p38αcompound inhibitory potency was quantitated from dose-response $IC_{50}$ values or Ki values from p38α/MK2 cascade assays while the substrate selectivity was calculated as a ratio of p38α/PRAK:p38α/MK2 $IC_{50}$ values. Compounds, described hereinabove, evaluated in this assay, are expected to provide a therapeutic benefit in the treatment of p38 MAP Kinase mediated diseases, such as autoimmune diseases and lymphoma.

Compounds were tested in accordance with the above described assay, yielding $IC_{50}$ values described below:

| Compound | Structure | p38/MK2 $IC_{50}$ (μM) | p38/PRAK $IC_{50}$ (μM) | Selectivity Ratio |
|---|---|---|---|---|
| Compound 49a | 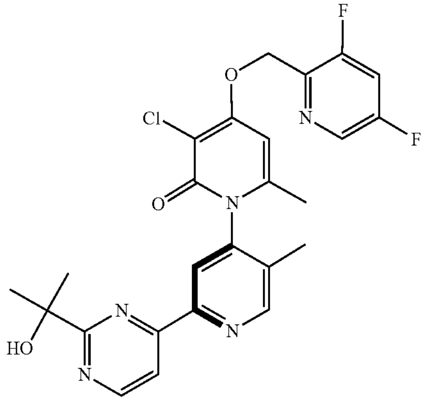 | 0.021 | 8.1 | 385x |
| Compound 49b | 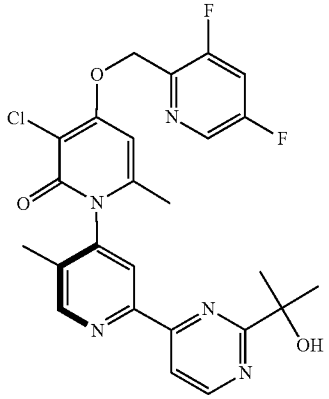 | 3.48 | 12.5 | 3.6 |

compound necessary to inhibit biosynthesis of TNFα, IL-6, and IL-1β (proinflammatory cytokines) by half. This is a reflection of the invention compound's effectiveness in helping to lower inflammation, an effect which helps treat many diseases, including autoimmune conditions, lymphoma, and rheumatoid arthritis. Evaluation of the potency and efficacy of p38 inhibitors to block cytokine production was carried out using the human U937 cell line. The U937 human pre-monocytic cell line was obtained from the American Type Culture Collection (Rockville, MD). These cells were differentiated to a monocytic/macrophage phenotype as described by Burnette (Burnette et al, (2009). SD0006: a potent, selective and orally available inhibitor of p38 MAP Kinase, Pharmacology 84(1):42-60). Differentiated U937 cells (human peripheral blood mononuclear cells (hPBMC)) were seeded into 96-well tissue culture plates (200,000 cells/well) in complete media. After 24 hours, the cells were pretreated for 60 minutes in the presence or absence of compound and then stimulated with LPS (0.1 μg/mL) for 4 hours. Culture media were then collected for determination of TNFα, IL-6 or IL-1β levels by ELISA. Cytokine concentrations were extrapolated from recombinant protein standard curves using a four-parameter logistic model and solving for $IC_{50}$ after iterating to the best least-squares fit. Compounds, described hereinabove, evaluated in

Example 10: Cytokine Regulation in Human Monocytes

The p38 pathway has been shown to be critical for the biosynthesis of a number of proinflammatory cytokines including TNFα, IL-1β and IL-6. Therefore, inhibition of the p38 MAP Kinase pathway will lower the inflammatory response by decreasing biosynthesis of proinflammatory cytokines. This study shows the amount of the invention this assay, are expected to provide a therapeutic benefit in the treatment of p38 MAP Kinase mediated diseases, such as lymphoma or inflammation.

Compounds were tested in accordance with the above described assay, yielding $IC_{50}$ values described below:

| Compound | Structure | hPBMC TNFα $IC_{50}$ (μM) | hPBMC IL-1β $IC_{50}$ (μM) | hPBMC IL-6 $IC_{50}$ (μM) |
|---|---|---|---|---|
| Compound 49a | 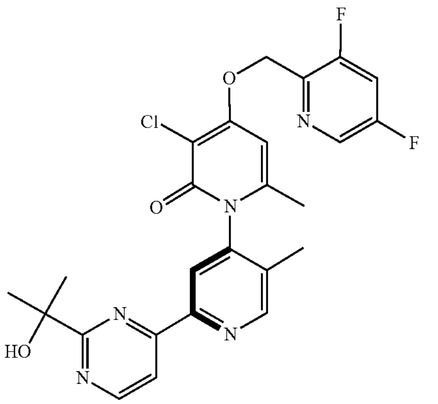 | 0.004 | 0.012 | 0.145 |
| Compound 49b | 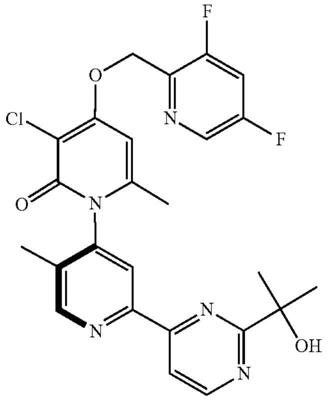 | >10,000 | >10,000 | >10,000 |

Example 11: Phosphoprotein Analysis in Human Monocytes

This study shows the effectiveness and selectivity of the invention compound in inhibiting the JNK pathway. The JNK pathway leads to increased inflammation by boosting production of inflammatory cytokines. Inhibition of this pathway will lead to less inflammation and therefore will treat many diseases, including autoimmune conditions, lymphoma, and rheumatoid arthritis. Classical p38 inhibitors block the phosphorylation of downstream substrates of p38 while elevating activity of parallel pathways such as JNK. Evaluation of the impact of different classes of p38 inhibitors on p38 and JNK pathway regulation was carried out using phospho-HSP27 and phosphor-JNK for the two pathways, respectively. Evaluation of the potency and efficacy of p38 inhibitors to impact phosphoprotein levels was carried out using the human U937 cell line. The U937 human pre-monocytic cell line was obtained from the American Type Culture Collection (Rockville, MD). These cells were differentiated to a monocytic/macrophage phenotype as described by Burnette (Burnette et al, (2009). SD0006: a potent, selective and orally available inhibitor of p38 MAP Kinase, Pharmacology 84(1):42-60). Suspension cells (approximately 0.5 million per milliliter in T75 $cm^2$ tissue culture flasks) were grown in RPMI containing 10% fetal bovine serum (FBS) plus antibiotics. On day one, phorbol 12-myristate 13-acetate (PMA, 20 ng/mL) was added to the culture flask and the cells were incubated overnight at 37° C./5% $CO_2$. The cells were washed on day two by centrifuging and resuspending them in fresh media without PMA. Adherent cells were harvested on day three by scraping, centrifuging and resuspending them in fresh media at a density of 1 million per milliliter. The PMA-differentiated U937 cells were then distributed into each well of a 96-well flat bottom tissue culture plate (100 mL/well) and the 100,000 cells/well were allowed to recover, incubated, overnight. On the day of the assay fresh media (50 mL/well) was added to the plates followed by the addition of compound (25 mL/well, concentration response) for 1 hour. The cells were stimulated with LPS (100 ng/mL) in a final assay volume of 100 mL. After 30 minutes, complete lysis buffer (50 mL/well MSD Tris lysis buffer, supplemented with protease inhibitors and phosphatase inhibitors) was added and the plate was placed on a shaker at 4° C. for 30 minutes before being stored frozen at −20° C. The cellular lysate (25 mL/well) was thawed and transferred from the assay plate to Meso Scale detection plates for determination of phospho-Hsp27/total Hsp27 or phospho-JNK/total JNK.

Compounds were tested in accordance with the above described assay, yielding $IC_{50}$ and $EC_{50}$ values described below:

| Compound | Structure | pHSP27/Total HSP27 $IC_{50}$ (nM) | pJNK/Total JNK $EC_{50}$ (nM) | Selectivity Ratio |
|---|---|---|---|---|
| Compound 49a | 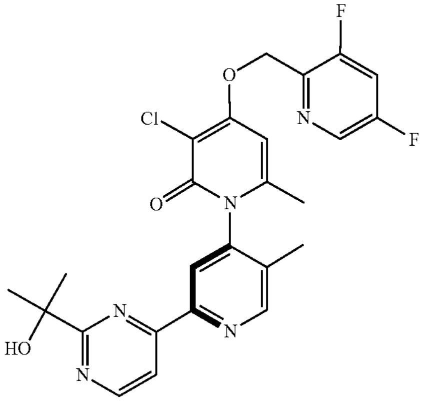 | 1.15x | 117x | 102x |
| Compound 49b | 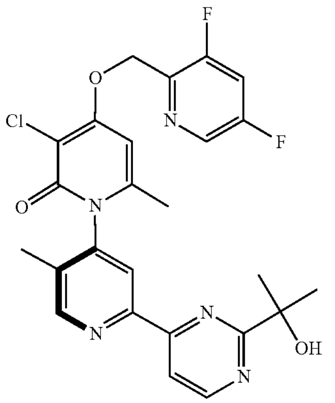 | | | |

Example 12: Endotoxin-induced cytokine production from human whole blood: Human whole blood (HWB; 25-45 mL) was collected from an NSAID-free donor into vacutainer collection tubes containing sodium heparin (10 mL, 158 USP units), pooled and rocked gently before being distributed into each well of a 96-well round bottom tissue culture plate (180 mL/well). Compounds (10 mL/well, concentration response) were added and mixed gently for 15-20 seconds using a disposable 96 polypropylene pin tool before the plates were incubated at 37° C./5% $CO_2$ for 1 hour. The HWB was stimulated with LPS (100 ng/mL) in a final assay volume of 200 mL. After 3 hours, the plates were spun at 240×g for 5 minutes to pellet the red cells. The plasma was carefully transferred to another 96-well round bottom plate and diluted 2-fold with assay media (DMEM containing 1000 fetal bovine serum (FBS) plus antibiotics). Finally, the diluted plasma (25 mL/well) was transferred to Meso Scale detection plates for determination of IL-1, IL-6 or TNFα.

Compounds were tested in accordance with the above described assay, yielding $IC_{50}$ and $EC_{50}$ values described below:

| Compound | Structure | HWB TNFα $IC_{50}$ (μM) | HWB IL-1β $IC_{50}$ (μM) | HWB IL-6 $IC_{50}$ (μM) |
|---|---|---|---|---|
| Compound 49a | 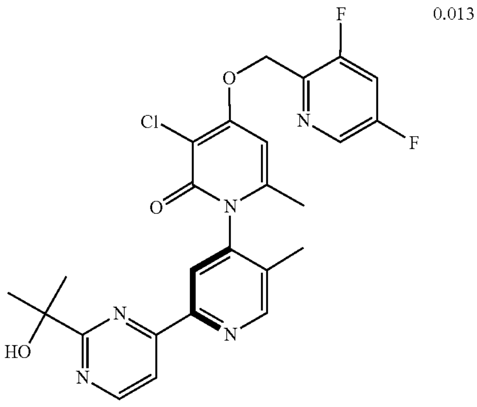 | 0.013 | 0.006 | 0.035 |
| Compound 49b | 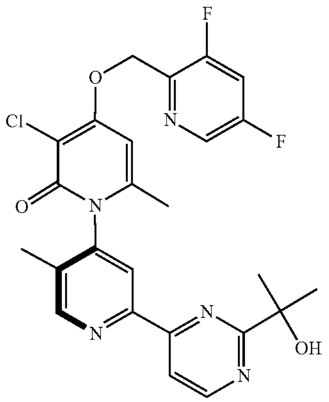 | | | |

Example 13: Determination of IL-1-Induced IL-6 Production in A549 Cells

Adherent A549 cells (approximately 5 million per T75 $cm^2$ tissue culture flask) were grown in F-12K media containing 10% fetal bovine serum (FBS) plus antibiotics. The cells were trypsinized, washed and resuspended at 0.3 million per milliliter. A549 cells were then distributed into each well of a 96-well flat bottom tissue culture plate (100 mL/well) and the 30,000 cells/well were allowed to recover, incubated, overnight. On the day of the assay fresh media (50 mL/well) was added to the plates followed by the addition of compound (25 mL/well, concentration response) for 1 hour. The cells were stimulated with LPS (100 ng/mL) in a final assay volume of 100 mL. After 3 hours, cultured media (25 mL/well) was transferred from the assay plate to a Meso Scale custom coated detection plate for determination of IL-6 levels. The detection plate was incubated at 4° C. overnight followed by the addition of a sulfo-tagged antibody cocktail (25 mL/well) for 1 hour at room temperature, with vigorous shaking. Read buffer (150 mL/well, MSD 4× read buffer diluted 4-fold with $dH_2O$) was added and the plate was read using the Meso Scale Sector Imager 6000. Upon electrical stimulation of the detection plate, co-reactants in the read buffer enhance an electrochemical reaction resulting in the release of energy in the form of light. This signal was captured by an internal CCD camera and quantitated. Viability of A549 cells was determined using an MTT assay. After the 3 hour incubation of cells with LPS and collection of the cultured media, the assay plates were inverted and gently tapped to remove any remaining liquid. MTT (1 mg/mL solution prepared in assay media) was added (100 mL/well) and the plates were returned to the 37° C./5% $CO_2$ incubator for 3 hours. The plates were again inverted to remove any liquid and allowed to dry overnight. Isopropanol (100 mL/well) was added to solubilize the resulting formazan crystals and the plate was read at 570 nm/650 nm using a Molecular Devices SpectraMax spectrophotometer.

Example 14: IL-1β Induced Prostaglandin Production in Rheumatoid Arthritis Synovial Fibroblasts (RASF)

Rheumatoid arthritis synovial fibroblasts (RASF) are derived from the inflamed synovium of a female RA patient who was undergoing total knee replacement. Synovial tissue was teased away from adjacent cartilage and dispersed into single cells with collagenase. Cells were expanded and banked. RASF cells were further cultured as described by Burnette supra. RASF cells were seeded into 96-well tissue culture plates ($5\times10^4$ cells/well) in complete growth medium. After 24 hours, the medium was replaced with fresh growth medium containing 1% FBS. Cells were treated with serial concentrations (30,000-0.01 nM) of compound or dimethyl-sulfoxide (DMSO) vehicle control for 1 hour then stimulated with 1 ng/mL IL-1β (R&D Systems, Minneapolis, MN) for 18-20 hours at 37° C. and conditioned media collected. $PGE_2$ levels the in cultured media were quantitated by ELISA (Cayman Chemical, Ann Arbor, MI). Compounds, described hereinabove, evaluated in this assay, are expected to provide a therapeutic benefit in the treatment of p38 MAP Kinase mediated diseases, such as lymphoma or rheumatoid arthritis.

Example 15: Substrate Selectivity in HUVEC Cells

When a compound was identified from the biochemical characterization step with selective inhibition of p38/MK2, it was next placed into a cell-based assay to verify enzyme to cell translatability. These assays utilize human umbilical vein endothelial cells (HUVEC) to demonstrate inhibition of Hsp27 phosphorylation (a biomarker of p38/MK2 activation) while sparing production of tissue factor (TF), which was linked to another downstream substrate of p38, MSK. In a 96-well format, adherent HUVEC (at 5 passages or less) were treated for 1 hour with serially-diluted compounds, including a non-selective p38 inhibitor as a reference, or vehicle for controls. For Hsp27 phosphorylation, cells were then stimulated with 500 μg/mL IL-1β for 0.5 hours, media was removed, cells were lysed, and phospho-Hsp27 in the lysate was quantitated by enzyme-linked immunosorbent assay (ELISA)(Life Technologies, Carlsbad, CA). The procedure for TF release was a similar ELISA-based assay (American Diagnostica, Stanford, CT), except that IL-1β stimulation proceeds for 5 hours. The ratio of TF inhibition $IC_{50}$:HSP27 phosphorylation inhibition $IC_{50}$ was defined as the substrate selectivity index in these cells. Compounds, described hereinabove, evaluated in this assay, are expected to provide a therapeutic benefit in the treatment of p38 MAP Kinase mediated diseases, such as lymphoma and autoinflammatory disease.

Example 16: Canine B Cell Growth Regulation $p^{38}$ MAP Kinase inhibitors have been shown to uniquely inhibit canine B cell proliferation and survival. This selective effect on canine B cells may be exploited in therapeutic treatment for canine B cell lymphoma, a fatal disease that impacts >40,000 companion animals in the United States. Quantitation of impact of p38 inhibitors on B cell growth is a cellular indicator of efficacy in B cell lymphoma. Compounds, described hereinabove, evaluated in this assay, are expected to provide a therapeutic benefit in the treatment of p38 MAP Kinase mediated diseases, such as lymphoma. These assays utilize beagle dog spleens obtained with protocols approved by the Saint Louis University Animal Care and Use Committee in collaboration with Seventh Wave Laboratories. Leukocytes were isolated from splenocytes by centrifugation through Histopaque 1077. To evaluate effect on proliferation, leukocytes were then cultured for 48 hours in 96-well plates in the presence of vehicle or test compounds. Cells were stimulated with LPS for TLR4 stimulation, *Staphylococcus aureus* B cell mitogen, or concanavalin-A T cell mitogen, then proliferation was quantitated with a BRDU incorporation ELISA (Roche, Mannheim, Germany). For apoptosis experiments, leukocytes were plated on 96-well polypropylene U bottom plates and treated with p38 MAP Kinase inhibitors or staurosporine (as a positive control) for up to 24 hours in the absence or presence of actinomycin D or cycloheximide (if needed to increase apoptosis rate). Apoptosis was determined using Caspase-Glo 3/7 luminescent assay (Promega, Madison, WI). In both assays, values generated after incubation with increasing concentrations of the inhibitors were compared to a negative control without inhibitors.

Example 17: LPS Induced TNFα Production in Rats

Rats were fasted eighteen hours prior to oral dosing, and allowed free access to water throughout the experiment. Each treatment group consists of five animals. Compounds were prepared as a suspension in a vehicle consisting of 0.5% methylcellulose, (Sigma Aldrich, St. Louis, MO), 0.025% Tween 20 (Sigma Aldrich). The compound or vehicle was administered by oral gavage in a volume of 1 mL. Two vehicle groups were used per experiment to control for intra-experiment variability. LPS (*E. coli* serotype 0111: B4, Sigma Aldrich) was administered four hours after compound intravenous injection at a dose of 1 mg/kg in 0.5 mL sterile saline (Baxter Healthcare, Deerfield, IL). Blood was collected in serum separator tubes via cardiac puncture ninety minutes after LPS injection, a time point corresponding to maximal TNFα and IL-1β production. After clotting, serum was withdrawn and stored at −20° C. and IL-1β and TNFαlevels quantitated by ELISA (Burnette supra). Compounds, described hereinabove, evaluated in this assay, are expected to provide a therapeutic benefit in the treatment of p38 MAP Kinase mediated diseases, such as lymphoma or inflammation.

Embodiments of the Disclosure

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention provides also the following non-limiting embodiments.

Embodiment 1 is a crystalline form of Compound 49a:

Compound 49a

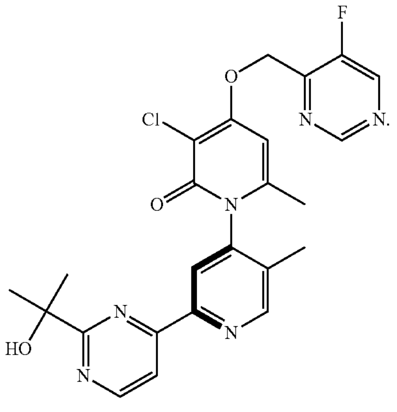

(P)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one Embodiment 2 is the crystalline form of Embodiment 1, wherein Compound 49a is a freebase.

Embodiment 3 is the crystalline form of any one of Embodiments 1 and 2, wherein the crystalline form of Compound 49a is Form A.

Embodiment 4 is the crystalline form of Embodiment 3, wherein Form A is characterized by an XRPD pattern having a peak expressed in degrees 2θ (+0.2) at about 9.78.

Embodiment 5 is the crystalline form of Embodiment 3, wherein Form A is characterized by an XRPD pattern having peaks expressed in degrees 2θ (+0.2) at about 9.78 and about 15.51.

Embodiment 6 is the crystalline form of Embodiment 3, wherein Form A is characterized by an XRPD pattern having peaks expressed in degrees 2θ (+0.2) at about 9.78, about 15.51, about 19.6, and about 25.92.

Embodiment 7 is the crystalline form of Embodiment 3, wherein Form A is characterized by an XRPD pattern having peaks expressed in degrees 2θ at about 9.78, about 15.34, about 15.51, about 19.6, about 20.57, about 21.01, about 25.92, about 29.05, and about 29.48.

Embodiment 8 is the crystalline form of Embodiment 3, wherein Form A is characterized by a DSC plot comprising an initial endothermic melting event with an onset temperature of about 188° C., followed by an exothermic recrystallization event at about 196° C., with a final sharp endothermic melting event at about 254° C.

Embodiment 9 is the crystalline form of any one of Embodiments 1-8, wherein the crystalline form further comprises not more than about 20 mol % of Compound 49a's corresponding M isomer.

Embodiment 10 is the crystalline form of any one of Embodiments 1-8, wherein the crystalline form further comprises not more than about 0.25 mol % of Compound 49a's corresponding M isomer.

Embodiment 11 is the crystalline form of any one of Embodiments 1-8, wherein the crystalline form is substantially free of Compound 49a's corresponding Misomer.

Embodiment 12 is the crystalline form of any one of Embodiments 1-11, wherein Compound 49a has a chemical purity of about 95% or greater.

Embodiment 13 is the crystalline form of any one of Embodiments 1-12, wherein the crystalline form of Compound 49a contains not more than about 20 mol % of other solid forms.

Embodiment 14 is the crystalline form of any one of Embodiments 1-12, wherein the crystalline form of Compound 49a contains not more than about 0.25 mol % of other solid forms.

Embodiment 15 is the crystalline form of any one of Embodiments 1-12, wherein the crystalline form of Compound 49a is substantially free of other solid forms.

Embodiment 16 is a pharmaceutical composition comprising a crystalline form of Compound 49a:

Compound 49a

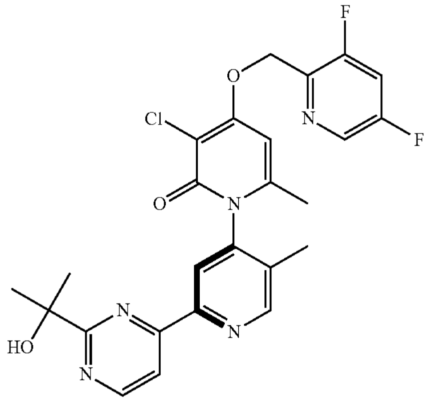

(P)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one and a pharmaceutically acceptable excipient.

Embodiment 17 is a pharmaceutical composition comprising comprising Compound 49a, or a pharmaceutically acceptable salt thereof, or a freebase thereof, and Compound 49b, or a pharmaceutically acceptable salt thereof, or a freebase thereof:

Compound 49a

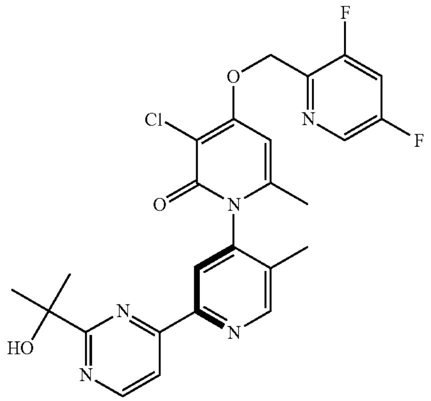

(P)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one -continued Compound 49b

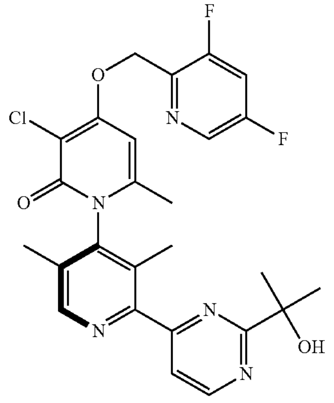

(M)-3-chloro-4-((3,5-difluoropyridin-2-yl)methoxy)-2′-(2-(2-hydroxypropan-2-yl)pyrimidin-4-yl)-5′,6-dimethyl-2H-[1,4′-bipyridin]-2-one wherein the molar ratio of Compound 49a, or a pharmaceutically acceptable salt thereof, or a freebase thereof, to Compound 49b, or a pharmaceutically acceptable salt thereof, or a freebase thereof, is about 4:1;

and a pharmaceutically acceptable excipient.

Embodiment 18 is the pharmaceutical composition of any one of Embodiments 16 and 17, wherein Compound 49a is a freebase.

Embodiment 19 is the pharmaceutical composition of any one of Embodiments 16-18, wherein the crystalline form of Compound 49a is Form A.

Embodiment 20 is the pharmaceutical composition of Embodiment 19, wherein Form A is characterized by an XRPD pattern having a peak expressed in degrees 2θ (+0.2) at about 9.78.

Embodiment 21 is the pharmaceutical composition of Embodiment 19, wherein Form A is characterized by an XRPD pattern having peaks expressed in degrees 2θ (+0.2) at about 9.78 and about 15.51.

Embodiment 22 is the pharmaceutical composition of Embodiment 19, wherein Form A is characterized by an XRPD pattern having peaks expressed in degrees 2θ (+0.2) at about 9.78, about 15.51, about 19.6, and about 25.92.

Embodiment 23 is the pharmaceutical composition of Embodiment 19, wherein Form A is characterized by an XRPD pattern having peaks expressed in degrees 2θ at about 9.78, about 15.34, about 15.51, about 19.6, about 20.57, about 21.01, about 25.92, about 29.05, and about 29.48.

Embodiment 24 is the pharmaceutical composition of Embodiment 19, wherein Form A is characterized by a DSC plot comprising an initial endothermic melting event with an onset temperature of about 188° C., followed by an exothermic recrystallization event at about 196° C., with a final sharp endothermic melting event at about 254° C.

Embodiment 25 is the pharmaceutical composition of any one of Embodiments 16-24, wherein the pharmaceutical composition further comprises not more than about 20 mol % of Compound 49a's corresponding M isomer.

Embodiment 26 is the pharmaceutical composition of any one of Embodiments 16-24, wherein the pharmaceutical composition further comprises not more than about 0.25 mol % of Compound 49a's corresponding M isomer.

Embodiment 27 is the pharmaceutical composition of any one of Embodiments 16-24, wherein the pharmaceutical composition is substantially free of Compound 49a's corresponding M isomer.

Embodiment 28 is the pharmaceutical composition of any one of Embodiments 16-27, wherein Compound 49a has a chemical purity of about 95% or greater.

Embodiment 29 is the pharmaceutical composition of any one of Embodiments 16-28, wherein the crystalline form of Compound 49a contains not more than about 20 mol % of other solid forms.

Embodiment 30 is the pharmaceutical composition of any one of Embodiments 16-28, wherein the crystalline form of Compound 49a contains not more than about 0.25 mol % of other solid forms.

Embodiment 31 is the pharmaceutical composition of any one of Embodiments 16-28, wherein the crystalline form of Compound 49a is substantially free of other solid forms.

Embodiment 32 is the pharmaceutical composition of any one of Embodiments 16-31, wherein the therapeutically effective amount is about 10 mg to about 300 mg.

Embodiment 33 is the pharmaceutical composition of Embodiment 32, wherein the therapeutically effective amount is about 50 mg.

Embodiment 34 is the pharmaceutical composition of any one of Embodiments 16-31, wherein the pharmaceutical composition is an oral pharmaceutical composition.

Embodiment 35 is a tablet comprising the pharmaceutical composition of any one of Embodiments 1-32.

What is claimed is:

1. A crystalline form of (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Compound 49a) of the following structure:

Compound 49a

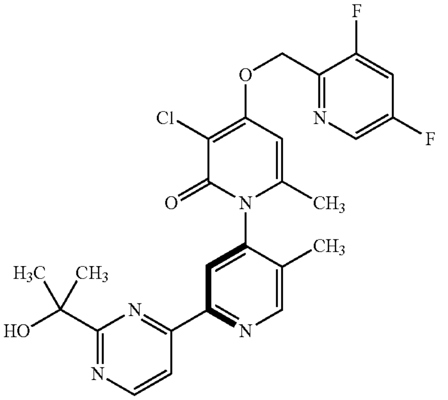

wherein the crystalline form of (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Compound 49a) is Form A; and wherein Form A is characterized by an X-ray powder diffraction (XRPD) pattern comprising a characteristic peak at an angle expressed in degrees 2-theta (°2θ) of 9.78°±0.2°.

2. The crystalline Form A of claim 1, wherein the crystalline Form A is further characterized by an X-ray powder diffraction (XRPD) pattern comprising a characteristic peak at an angle expressed in degrees 2-theta (°2θ) of 15.51°±0.2°.

3. The crystalline Form A of claim 1, wherein the crystalline Form A is further characterized by an X-ray powder diffraction (XRPD) pattern comprising characteristic peaks at angles expressed in degrees 2-theta (°2θ) of 15.51°±0.2°, 19.60°±0.2°, and 25.92°±0.2°.

4. The crystalline Form A of claim 1, wherein the crystalline Form A is further characterized by an X-ray powder diffraction (XRPD) pattern comprising characteristic peaks at angles expressed in degrees 2-theta (°2θ) of 15.34°±0.2°, 15.51°±0.2°, 19.60°±0.2°, 20.57°±0.2°, 21.01°±0.2°, 25.92°±0.2°, 29.05°±0.2°, and 29.48°±0.2°.

5. The crystalline Form A of claim 1, wherein the crystalline Form A is further characterized by a Fourier transform infrared (FTIR) spectrum comprising characteristic peaks ($cm^{-1}$) at 3486, 3072, 2982, 1656, 1605, 1592, 1571, 1546, 1525, 1476, 1457, 1429, 1385, 1380, 1350, 1296, 1237, 1214, 1184, 1130, 1103, 1051, 1044, 1005, 978, 964, 860, 840, 810, 793, 781, 755, 741, 703, and 669.

6. The crystalline Form A of claim 1, wherein the crystalline Form A is further characterized by a differential scanning calorimetry (DSC) thermogram comprising an initial endothermic melting event with an onset temperature of 188° C., followed by an exothermic recrystallization event at 196° C., with a final sharp exothermic melting event at 254° C.

7. The crystalline Form A of claim 1, wherein the crystalline Form A is further characterized by a differential scanning calorimetry (DSC) thermogram comprising a single melting event at 192.6° C.

8. A pharmaceutical composition comprising a pharmaceutically acceptable excipient and a therapeutically effective amount of the crystalline Form A of claim 1.

9. The pharmaceutical composition of claim 8, wherein the therapeutically effective amount is in the range of from 10 mg to 300 mg.

10. The pharmaceutical composition of claim 9, wherein the therapeutically effective amount is 50 mg.

11. The pharmaceutical composition of claim 8, wherein the pharmaceutical composition is an oral pharmaceutical composition.

12. The pharmaceutical composition of claim 8, wherein the pharmaceutical composition is formulated as a tablet.

* * * * *